United States Patent
Torii et al.

(10) Patent No.: US 9,790,497 B2
(45) Date of Patent: Oct. 17, 2017

(54) MORPHOLINO OLIGONUCLEOTIDE MANUFACTURING METHOD

(71) Applicant: AJINOMOTO CO., INC., Tokyo (JP)

(72) Inventors: Takayoshi Torii, Yokkaichi (JP); Daisuke Takahashi, Yokkaichi (JP); Satoshi Katayama, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/946,991

(22) Filed: Nov. 20, 2015

(65) Prior Publication Data

US 2016/0076033 A1    Mar. 17, 2016

Related U.S. Application Data

(63) Continuation of application No. PCT/JP2014/063750, filed on May 23, 2014.

(30) Foreign Application Priority Data

May 24, 2013 (JP) ................................. 2013-110358

(51) Int. Cl.
| | |
|---|---|
| *C07D 413/04* | (2006.01) |
| *C07D 487/04* | (2006.01) |
| *C12N 15/113* | (2010.01) |
| *C07D 519/00* | (2006.01) |
| *C12N 15/11* | (2006.01) |
| *C07H 21/00* | (2006.01) |

(52) U.S. Cl.
CPC .......... *C12N 15/113* (2013.01); *C07D 413/04* (2013.01); *C07D 487/04* (2013.01); *C07D 519/00* (2013.01); *C12N 15/111* (2013.01); *C07H 21/00* (2013.01); *C12N 2310/11* (2013.01); *C12N 2310/3233* (2013.01); *C12N 2330/30* (2013.01); *Y02P 20/55* (2015.11)

(58) Field of Classification Search
CPC ............................ C07D 413/04; C07D 487/04
See application file for complete search history.

(56) References Cited

U.S. PATENT DOCUMENTS

| | | |
|---|---|---|
| 5,185,444 A | 2/1993 | Summerton et al. |
| 5,506,337 A | 4/1996 | Summerton et al. |
| 5,521,063 A | 5/1996 | Summerton et al. |
| 5,698,685 A | 12/1997 | Summerton et al. |
| 9,029,528 B2 | 5/2015 | Hirai et al. |
| 9,161,948 B2 | 10/2015 | Hanson |
| 9,278,987 B2 | 3/2016 | Hanson et al. |
| 2007/0135333 A1 | 6/2007 | Geller et al. |
| 2008/0194463 A1 | 8/2008 | Weller et al. |
| 2009/0131624 A1 | 5/2009 | Reeves et al. |
| 2009/0131632 A1 | 5/2009 | Fox et al. |
| 2010/0234280 A1 | 9/2010 | Geller et al. |
| 2010/0234281 A1 | 9/2010 | Weller et al. |
| 2012/0289457 A1 | 11/2012 | Hanson |
| 2012/0296074 A1 | 11/2012 | Hirai et al. |
| 2014/0213737 A1 | 7/2014 | Weller et al. |
| 2014/0330006 A1 | 11/2014 | Hanson et al. |
| 2016/0237426 A1 | 8/2016 | Hanson |

FOREIGN PATENT DOCUMENTS

| | | |
|---|---|---|
| JP | 1 172384 A | 7/1989 |
| JP | 2010-275254 A | 12/2010 |
| WO | WO 91/09033 A1 | 6/1991 |
| WO | WO 2008/008113 A1 | 1/2008 |
| WO | WO 2009/064471 A1 | 5/2009 |
| WO | WO 2012/150960 A1 | 11/2012 |
| WO | WO 2012/157723 A1 | 11/2012 |
| WO | WO 2013/074834 A1 | 5/2013 |

OTHER PUBLICATIONS

International Search Report issued Jun. 24, 2014 in PCT/JP2014/063750 (with English Translation).
James Summerton et al.,"Morpholino Antisense Oligomers: Design, Preparation, and Properties", Antisense and Nucleic Acid Drug Development, vol. 7, 1997, pp. 187-195 and cover page.
Taro Harakawa et al., "Development of an Efficient Method for Phosphorodiamidate Bond Formation by Using Inorganic Salts", Bioorg. Med. Chem. Lett., vol. 22, 2012, pp. 1445-1447.

*Primary Examiner* — Rebecca Anderson
(74) *Attorney, Agent, or Firm* — Oblon, McClelland, Maier & Neustadt, L.L.P.

(57) ABSTRACT

Using a morpholino nucleotide wherein 5'-hydroxy group or a hydroxy group present on the substituent of the 5'-hydroxy group is protected by a protecting group having an alkyl group having not less than 10 and not more than 300 carbon atoms and/or an alkenyl group having not less than 10 and not more than 300 carbon atoms as a starting material, a method capable of efficiently producing the morpholino oligonucleotide in a high yield by a liquid phase synthesis can be provided.

8 Claims, No Drawings

MORPHOLINO OLIGONUCLEOTIDE MANUFACTURING METHOD

CROSS REFERENCES TO RELATED APPLICATIONS

This application is a continuation of International Patent Application No. PCT/JP2014/063750, filed on May 23, 2014, and claims priority to Japanese Patent Application No. 2013-110358, filed on May 24, 2013, all of which are incorporated herein by reference in their entireties.

BACKGROUND OF THE INVENTION

Field of the Invention

The present invention relates to a production method of morpholino oligonucleotide, and morpholino nucleotide used as a starting material of the production method.

Discussion of the Background

Morpholino oligonucleotide is a compound attracting attention for its use as an antisense oligonucleotide, since it shows high affinity for DNA and RNA, resistance to various nucleases, stability in vivo and low toxicity (see non-patent document 1).

As a production method of morpholino oligonucleotide, a solid phase synthesis and a liquid phase synthesis have been reported (see non-patent document 2, patent documents 1-5).

The solid phase synthesis is advantageous from the aspect of speed since it enables automatic synthesis. On the contrary, it is not suitable for industrial large scale synthesis since scaling-up is limited due to facility restriction, and low reactivity requires use of an excess monomer to be the reagent in a nucleotide elongation reaction. Also, it is associated with defects in that confirmation of the progress status of the reaction in an intermediate stage, analysis of intermediate structure and the like are difficult.

On the other hand, the liquid phase synthesis requires complicated treatments such as column purification and the like, and a large-scale and rapid synthesis of about 20mer chain length morpholino oligonucleotide, which is utilizable as an antisense pharmaceutical product, has been difficult.

In recent years, a synthetic method using hydrophobic group-linked nucleoside, pseudo solid phase-protected nucleoside and the like has been reported as an attempt to solve the respective defects of the liquid phase method and the solid phase method (see patent documents 6, 7). However, synthesis of morpholino oligonucleotide different in the reaction pathway and the reaction itself from those of oligonucleotide synthesis is not described or suggested.

DOCUMENT LIST

Patent Document patent document 1: WO 91/09033
patent document 2: WO 2008/008113
patent document 3: US 2009/0131632 A1
patent document 4: WO 2009/064471
patent document 5: WO 2012/043730
patent document 6: JP-A-2010-275254
patent document 7: WO 2012/157723

Non-Patent Document non-patent document 1: Summerton, J. et al., Antisense and Nucleic Acid Drug Development, 1997, Vol. 7, p. 187.

non-patent document 2: Harakawa et al., Bioorganic & Medicinal Chemistry Letters, 2012, Vol. 22, p. 1445-1447

SUMMARY OF THE INVENTION

Problems to be Solved by the Invention

The problem of the present invention is to provide a method of producing a morpholino oligonucleotide efficiently and in a high yield by a liquid phase method, and a novel morpholino nucleotide to be a starting material of the method.

Means of Solving the Problems

The present inventors have found that the above-mentioned problem can be solved by protecting the 5'-hydroxy group side with a particular protecting group in liquid phase synthesis of a morpholino oligonucleotide.

That is, using a morpholino nucleotide having the 5'-hydroxy group side protected by the protecting group as a starting material of morpholino oligonucleotide liquid phase synthesis, condensation reaction itself can be performed in a liquid phase, the reactivity is remarkably improved as compared to the solid phase method, monomer equivalents to be used can be remarkably reduced and, after the reaction, morpholino oligonucleotide can be conveniently isolated and purified by a crystallization or extraction operation. Consequently, a morpholino oligonucleotide having an about 20mer chain length and utilizable for pharmaceutical products can be synthesized efficiently in a high yield by a liquid phase method.

On the other hand, in the course of study of liquid phase synthesis of morpholino oligonucleotide by the present inventors, a problem was found that when an activated morpholino nucleoside monomer to be used for a condensation reaction remains in a trace amount in the subsequent cycle of condensation reaction, double addition is induced, and the quality of the obtained morpholino oligonucleotide is degraded. In this regard, they have found that the problem can be solved by treating the activated morpholino nucleoside monomer remaining after the condensation reaction with a quenching agent.

That is, the present invention includes the following.

[1] A morpholino nucleotide represented by the formula (I):

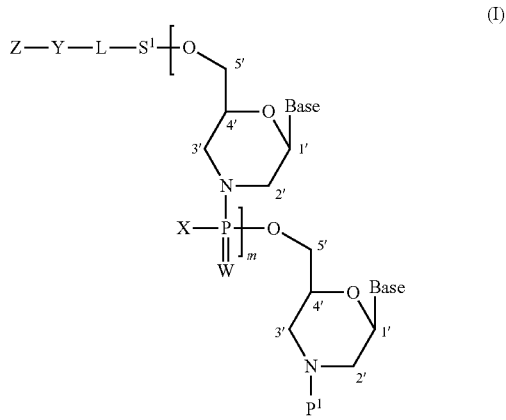

[wherein
m is any integer of not less than 0,
Base in the number of m+1 are each independently an optionally protected nucleic acid base,
$P^1$ is a hydrogen atom, or a temporary protecting group removable under acidic conditions,
X in the number of m are each independently a $C_{1-6}$ alkoxy group, a di-$C_{1-6}$ alkylamino group, or a piperazino group wherein a nitrogen atom at the 4-position is protected by a protecting group and further optionally substituted,
W in the number of m are each independently an oxygen atom or a sulfur atom,
$S^1$ is a single bond, or a group represented by *O—$S^2$** (wherein * indicates the bonding position to L, ** indicates the bonding position to a 5'-hydroxy group, and $S^2$ is a spacer having a main chain containing 1 to 20 atoms),
L is a single bond, or a group represented by the formula (a1):

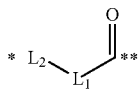

[wherein * indicates the bonding position to Y;
** indicates the bonding position to $S^1$;
$L_1$ is an optionally substituted divalent $C_{1-22}$ hydrocarbon group; and
$L_2$ is C(=O) or a group represented by *N($R^3$)—$R^1$—N($R^2$)C(=O) (wherein  indicates the bonding position to $L^1$, * indicates the bonding position to Y, $R^1$ is an optionally substituted $C_{1-22}$ alkylene group, $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond)],
Y is a single bond, an oxygen atom or NR (wherein R is a hydrogen atom, an alkyl group or an aralkyl group), and
Z is a group represented by the formula (a2):

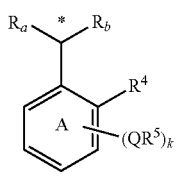

[wherein * indicates the bonding position to Y;
$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;
Q in the number of k are each independently a single bond, or —O—, —S—, —OC(=O)—, —NHC(=O)— or —NH—;
$R^5$ in the number of k are each independently an organic group having an alkyl group having not less than 10 and not more than 300 carbon atoms and/or an alkenyl group having not less than 10 and not more than 300 carbon atoms;
k is an integer of 1 to 4;
ring A optionally further has, in addition to $QR^5$ in the number of k, a substituent selected from the group consisting of a halogen atom, a $C_{1-6}$ alkyl group optionally substituted by a halogen atom(s), and a $C_{1-6}$ alkoxy group optionally substituted by a halogen atom(s);
$R_a$ is a hydrogen atom;
$R_b$ is a hydrogen atom, or a group represented by the formula (a3):

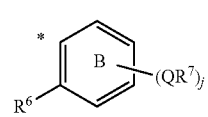

(wherein * indicates a bonding position;
j is an integer of 0 to 4;
Q in the number of j are as defined above;
$R^7$ in the number of j are each independently an organic group having an alkyl group having not less than 10 and not more than 300 carbon atoms and/or an alkenyl group having not less than 10 and not more than 300 carbon atoms;
$R^6$ is a hydrogen atom, or optionally a single bond or —O— in combination with $R^4$ to form a fluorenyl group or a xanthenyl group together with ring A; and
ring B optionally further has, in addition to $QR^7$ in the number of j, a substituent selected from the group consisting of a halogen atom, a $C_{1-6}$ alkyl group optionally substituted by a halogen atom(s), and a $C_{1-6}$ alkoxy group optionally substituted by a halogen atom(s)), or
$R_a$ and $R_b$ are joined to form an oxygen atom]].
[2] The morpholino nucleotide of [1], wherein m is 0.
[3] The morpholino nucleotide of [1] or [2], wherein L in the formula (I) is a succinyl group, and
$R^5$ and/or $R^7$ are/is an alkyl group having 10-40 carbon atoms.
[4] The morpholino nucleotide of [1] or [2], wherein L in the formula (I) is a succinyl group, and
$R_a$ and $R_b$ are both hydrogen atoms, and $R^5$ is an alkyl group having 10-40 carbon atoms.
[5] The morpholino nucleotide of [1] or [2], wherein L in the formula (I) is a succinyl group, and
$R^5$ and/or $R^7$ are/is an alkyl group having 12-30 carbon atoms.
[6] The morpholino nucleotide of [1] or [2], wherein, in the formula (I), L is a succinyl group, and
Z—Y— is a group selected from the group consisting of a 3,4,5-tri(octadecyloxy)benzyloxy group,
a 3,5-di(docosyloxy)benzyloxy group,
a 3,5-bis[3',4',5'-tri(octadecyloxy)benzyloxy]benzyloxy group,
a 3,4,5-tris[3',4',5'-tri(octadecyloxy)benzyloxy]benzyloxy group,
a 3,4,5-tri(octadecyloxy)benzylamino group,
a 2,4-di(docosyloxy)benzylamino group,
a 3,5-di(docosyloxy)benzylamino group,
a di(4-docosyloxyphenyl)methylamino group,
a 4-methoxy-2-[3',4',5'-tri(octadecyloxy)benzyloxy]benzylamino group,
a 4-methoxy-2-[3',4',5'-tri(octadecyloxy)cyclohexylmethyloxy]benzylamino group,
a 2,4-di(dodecyloxy)benzylamino group,
a phenyl(2,3,4-tri(octadecyloxy)phenyl)methylamino group,
a di[4-(12-docosyloxydodecyloxy)phenyl]methylamino group,
a 3,5-bis[3',4',5'-tri(octadecyloxy)benzyloxy]benzylamino group, and a 3,4,5-tris[3',4',5'-tri(octadecyloxy)benzyloxy]benzylamino group.

[7] The morpholino nucleotide of [1] or [2], wherein Z—Y-L- is selected from the group consisting of
a 2-{2,4-di(2',3'-dihydrophytyloxy)benzylaminocarbonyl}ethylcarbonyl group;
a 3,5-di(2',3'-dihydrophytyloxy)benzylsuccinyl group;
a 4-(2',3'-dihydrophytyloxy)benzylsuccinyl group;
a 2-{1-[(2-chloro-5-(2',3'-dihydrophytyloxy)phenyl)]benzylaminocarbonyl}ethylcarbonyl group;
a 3,4,5-tri(2',3'-dihydrophytyloxy)benzylsuccinyl group;
a 2-{3,4,5-tri(2',3'-dihydrophytyloxy)benzylaminocarbonyl}ethylcarbonyl group;
a 2-{4-(2',3'-dihydrophytyloxy)benzylaminocarbonyl}ethylcarbonyl group;
a 2-{2-[3',4',5'-tri(2'',3''-dihydrophytyloxy)benzyloxy]-4-methoxybenzylaminocarbonyl}ethylcarbonyl group;
a 2-{4-(2',3'-dihydrophytyloxy)-2-methoxybenzylaminocarbonyl}ethylcarbonyl group;
a 4-(2',3'-dihydrophytyloxy)-2-methylbenzylsuccinyl group;
a 2-{4-(2',3'-dihydrophytyloxy)-2-methylbenzylaminocarbonyl}ethylcarbonyl group;
a 4-[2,2,4,8,10,10-hexamethyl-5-dodecanoylamino]benzylsuccinyl group;
a 2-{4-[2,2,4,8,10,10-hexamethyl-5-dodecanoylamino]benzylaminocarbonyl}ethylcarbonyl group;
a 4-(3,7,11-trimethyldodecyloxy)benzylsuccinyl group;
a 2-{4-(3,7,11-trimethyldodecyloxy)benzylaminocarbonyl}ethylcarbonyl group;
a 2-{3,5-di(2',3'-dihydrophytyloxy)benzylaminocarbonyl}ethylcarbonyl group;
a 2-{1-[2,3,4-tri(2',3'-dihydrophytyloxy)phenyl]benzylaminocarbonyl}ethylcarbonyl group;
a 2-{1-[4-(2',3'-dihydrophytyloxy)phenyl]-4'-(2',3'-dihydrophytyloxy)benzylaminocarbonyl}ethylcarbonyl group;
a 3,4,5-tris[3,4,5-tri(2',3'-dihydrophytyloxy)benzyl]benzylsuccinyl group; and
a 2-{3,4,5-tris[3,4,5-tri(2',3'-dihydrophytyloxy)benzyl]benzylaminocarbonyl}ethylcarbonyl group.

[8] The morpholino nucleotide of any one of [1]-[7], wherein $P^1$ is a trityl group, a monomethoxytrityl group, or a dimethoxytrityl group.

[9] A method of producing n+p-mer morpholino oligonucleotide, comprising (1) a step of condensing a p-mer morpholino oligonucleotide (p is any integer of one or more) wherein a 5'-hydroxy group is activated (thio)phosphated or activated (thio)phosphoramidated, and a morpholine ring nitrogen atom is protected by a temporary protecting group removable under acidic conditions, with an n-mer morpholino oligonucleotide (n is an integer of one or more) wherein a 5'-hydroxy group or, when the 5'-hydroxy group has a substituent having a hydroxy group, the hydroxy group present on the substituent is protected by a protecting group having an alkyl group having not less than 10 and not more than 300 carbon atoms and/or an alkenyl group having not less than 10 and not more than 300 carbon atoms, and the morpholine ring nitrogen atom is not protected, by a (thio)phosphoramidate bond or (thio)phosphorodiamidate bond via the morpholine ring nitrogen atom.

[10] The production method of [9], wherein p is 1.

[11] The production method of [9] or [10], comprising treating the reaction mixture with a quenching agent after completion of the reaction.

[12] The production method of any one of [9]-[11], further comprising the following step (1'):
(1') a step of removing the temporary protecting group of the morpholine ring nitrogen atom by reacting, before the condensation step (1), the n-mer morpholino oligonucleotide wherein the 5'-hydroxy group or, when the 5'-hydroxy group has a substituent having a hydroxy group, the hydroxy group present on the substituent is protected by a protecting group having an alkyl group having not less than 10 and not more than 300 carbon atoms and/or an alkenyl group having not less than 10 and not more than 300 carbon atoms, and the morpholine ring nitrogen atom is protected by a temporary protecting group removable under acidic conditions, with an acid in a non-polar solvent.

[13] The production method of [12], wherein the temporary protecting group is removed in the presence of a cation scavenger.

[14] The production method of [12] or [13], further comprising a step of neutralizing with an organic base in step (1'), after removing the temporary protecting group of the morpholine ring nitrogen atom.

[15] The production method of any one of [9]-[14], wherein the protecting group having an alkyl group having not less than 10 and not more than 300 carbon atoms and/or an alkenyl group having not less than 10 and not more than 300 carbon atoms is a group represented by the following formula (II):

[L is a single bond, or a group represented by the formula (a1):

[wherein * indicates the bonding position to Y;
** indicates the bonding position to $S^1$;
$L_1$ is an optionally substituted divalent $C_{1-22}$ hydrocarbon group; and
$L_2$ is C(=O) or a group represented by *N($R^3$)—$R^1$—N($R^2$)C(=O) (wherein  indicates the bonding position to $L^1$, * indicates the bonding position to Y, $R^1$ is an optionally substituted $C_{1-22}$ alkylene group, $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond)],
Y is a single bond, an oxygen atom or NR (wherein R is a hydrogen atom, an alkyl group or an aralkyl group), and
Z is a group represented by the formula (a2):

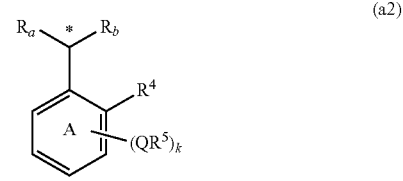

[wherein * indicates the bonding position to Y;
$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;
Q in the number of k are each independently a single bond, or —O—, —S—, —OC(=O)—, —NHC(=O)— or —NH—;

$R^5$ in the number of k are each independently an organic group having an alkyl group having not less than 10 and not more than 300 carbon atoms and/or an alkenyl group having not less than 10 and not more than 300 carbon atoms;
k is an integer of 1 to 4;
ring A optionally further has, in addition to $QR^5$ in the number of k, a substituent selected from the group consisting of a halogen atom, a $C_{1-6}$ alkyl group optionally substituted by a halogen atom(s), and a $C_{1-6}$ alkoxy group optionally substituted by a halogen atom(s);
$R_a$ is a hydrogen atom;
$R_b$ is a hydrogen atom, or a group represented by the formula (a3):

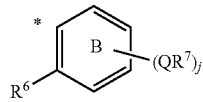

(wherein * indicates a bonding position;
j is an integer of 0 to 4;
Q in the number of j are as defined above;
$R^7$ in the number of j are each independently an organic group having an alkyl group having not less than 10 and not more than 300 carbon atoms and/or an alkenyl group having not less than 10 and not more than 300 carbon atoms;
$R^6$ is a hydrogen atom, or optionally a single bond or —O— in combination with $R^4$ to form a fluorenyl group or a xanthenyl group together with ring A; and
ring B optionally further has, in addition to $QR^7$ in the number of j, a substituent selected from the group consisting of a halogen atom, a $C_{1-6}$ alkyl group optionally substituted by a halogen atom(s), and a $C_{1-6}$ alkoxy group optionally substituted by a halogen atom(s)), or
$R_a$ and $R_b$ are joined to form an oxygen atom].
[16] The production method of [15], further comprising the following step (2):
(2) a step of obtaining morpholino oligonucleotide by adding a polar solvent to the reaction mixture obtained in step (1') and/or (1) and collecting precipitates thereof by solid-liquid separation.
[17] The production method of any one of [12]-[16], wherein the non-polar solvent is selected from the group consisting of a halogenated solvent, an aromatic solvent, an ester solvent, an aliphatic solvent, a non-polar ether solvent, and a combination of these.
[18] The production method of [16] or [17], wherein the polar solvent is an alcohol solvent or a nitrile solvent.
[19] The production method of any one of [9]-[18], further comprising the following step (3):
(3) a step of removing all the protecting groups of the obtained n+p-mer morpholino oligonucleotide.
[20] The production method of any one of [9]-[19], wherein the temporary protecting group removable under acidic conditions is a trityl group, a dimethoxytrityl group, or a monomethoxytrityl group.

Effect of the Invention

According to the present invention, since an advantage of a liquid phase method that monomer equivalent of a starting material of a condensation reaction can be reduced by improving the reactivity by protecting the 5'-hydroxy group side of morpholino nucleotide with a particular protecting group, and an advantage of a solid phase method that morpholino oligonucleotide can be conveniently isolated and purified by a crystallization, washing or extraction operation in each step of an elongation reaction can be combined, an industrial large-scale production of a morpholino oligonucleotide having about 20mer chain length and useful as a pharmaceutical product can be efficiently performed in a high yield.

In addition, it was found that degradation of the quality of the object morpholino oligonucleotide can be prevented by treating activated morpholino nucleoside monomer remaining after condensation reaction with a quenching agent. By combining same with the above-mentioned method, an efficient production method of high quality morpholino oligonucleotide in a large scale can be provided.

DETAILED DESCRIPTION OF THE PREFERRED EMBODIMENTS

The present invention relates to a novel morpholino nucleotide wherein the 5'-hydroxy group side is protected by a particular protecting group, and a morpholine ring nitrogen atom is optionally protected by a temporary protecting group removable under acidic conditions.

Another embodiment of the present invention is a method of producing n+p-mer morpholino oligonucleotide, comprising a step of condensing a p-mer morpholino oligonucleotide (p is any integer of one or more) wherein a 5'-hydroxy group is activated (thio)phosphated or activated (thio)phosphoramidated, and a morpholine ring nitrogen atom is protected by a temporary protecting group removable under acidic conditions, with an n-mer morpholino oligonucleotide (n is an integer of one or more) wherein a 5'-hydroxy group or a hydroxy group present on a substituent of the 5'-hydroxy group is protected by a protecting group having an alkyl group having not less than 10 and not more than 300 carbon atoms and/or an alkenyl group having not less than 10 and not more than 300 carbon atoms, and the morpholine ring nitrogen atom is not protected, by a (thio)phosphoramidate bond or (thio)phosphorodiamidate bond via the morpholine ring nitrogen atom.

Explanations are given below.
[Explanation of Terms]
Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the specification are hereby incorporated by reference so as to describe and disclose constructed products and methodology described in, for example, publications usable in relation to the described invention.

In the present specification, the "morpholino nucleoside" to be a constitutional unit of morpholino oligonucleotide is a compound represented by the following formula (1).

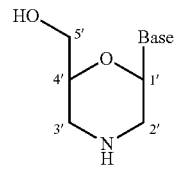

(wherein Base is an optionally protected nucleic acid base).

Morpholino nucleoside (1) can be prepared by a method known per se (e.g., the method described in WO 91/09033A1), or a method analogous thereto. Specifically, as shown in the following scheme, the corresponding ribonucleoside (2) is subjected to oxidative ring opening with sodium periodate etc. to give the corresponding 2',3'-dialdehyde (3), the dialdehyde (3) is subjected to ring closure with ammonia to give 2',3'-dihydroxymorpholino nucleoside (4), and dihydroxymorpholino nucleoside (4) is reduced with a reducing agent (e.g., sodium cyanoborohydride, sodium triacetoxyborohydride and the like), whereby morpholino nucleoside (1) can be obtained.

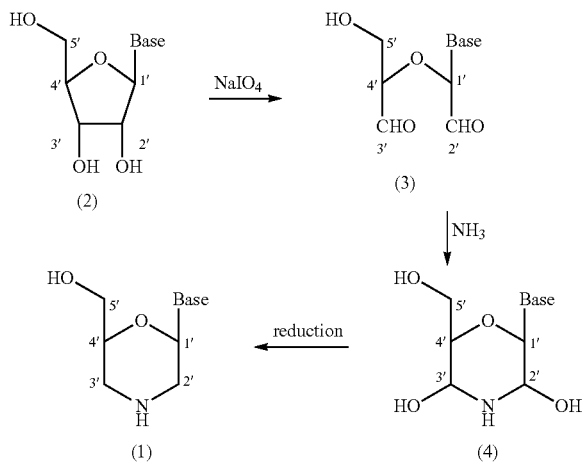

In the present specification, the position numbers (1', 2' and the like) of morpholino nucleoside correspond to the position numbers of carbon atoms of the ribose of the starting material ribonucleoside (2).

In the present specification, morpholino oligonucleotide means a compound wherein two or more morpholino nucleosides are polymerized by (thio)phosphoramidate bonding or (thio)phosphorodiamidate bonding via a 5'-hydroxy group and the nitrogen atom of a morpholine ring. For example, as m'+1-mer morpholino oligonucleotide, a compound represented by the following formula (5) can be mentioned.

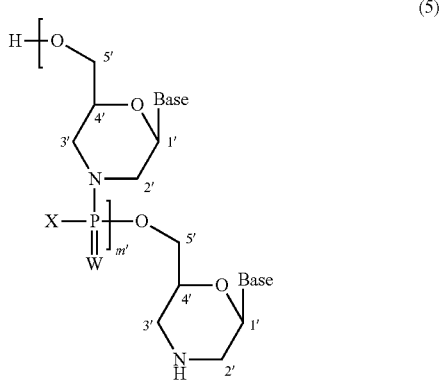

(wherein
m' is any integer of one or more,
Base in the number of m'+1 are each independently an optionally protected nucleic acid base,
X in the number of m' are each independently a $C_{1-6}$ alkoxy group, a di-$C_{1-6}$ alkylamino group, or a piperazino group wherein a nitrogen atom at the 4-position is protected by a protecting group, and further optionally substituted, and the like, and
W in the number of m' are each independently an oxygen atom or a sulfur atom).

In the present specification, the "piperazino group wherein a 4-position nitrogen atom is protected by a protecting group, and further optionally substituted" means that the 4-position nitrogen atom of the piperazino group is protected by a protecting group, and a piperazino group protected by a protecting group sustainable under the deprotection conditions of the morpholine ring nitrogen atom of morpholino nucleotide is preferable. As the "protecting group of the 4-position nitrogen atom of the piperazino group", an acyl group is preferable and, for example, an acyl group having a fluoro group in the carbon chain such as monofluoroacetyl group, difluoroacetyl group, trifluoroacetyl group, 2-fluoropropionyl group, 2,2-difluoropropionyl group, 3,3,3-trifluoropropionyl group, 2,3,3,3-tetrafluoropropionyl group, pentafluoropropionyl group and the like is more preferable (see WO 2008/008113). In the piperazino group, a hydrogen atom bonded to the carbon atom of the piperazino group may be substituted, and examples of the substituent include an alkyl group (preferably having 1-3 carbon atoms) such as methyl group and the like, and the like.

In the present specification, morpholino nucleoside at the terminal on the side having a free hydroxy group at the 5'-position of morpholino oligonucleotide (upper left side of the above-mentioned formula (5)) is referred to as the "5'-terminus", and morpholino nucleoside at the terminal on the opposite side (lower right side of the above-mentioned formula (5)) is referred to as the "3'-terminus", according to the usual practice in the nucleic acid chemistry.

In the present specification, the "nucleic acid base" is not particularly limited as long as it can be used for the synthesis of nucleic acid and includes, for example, a pyrimidine base such as cytosyl group, uracil group, thyminyl group and the like, and a purine base such as adenyl group, guanyl group and the like. The "optionally protected nucleic acid base" means, for example, that an amino group may be protected in an adenyl group, a guanyl group or a cytosyl group, which is a nucleic acid base having an amino group, and a nucleic acid base wherein the amino group therein is protected by a protecting group sustainable under the deprotection conditions of the morpholine ring nitrogen atom of the morpholino nucleotide is preferable. The "amino-protecting group" is not particularly limited, and examples thereof include the protecting groups described in Greene's PROTECTIVE GROUPS IN ORGANIC SYNTHESIS, 4th edition, Wiley-Interscience, 2006 and the like. Specific examples of the "amino-protecting group" include a pivaloyl group, a pivaloyloxymethyl group, a trifluoroacetyl group, a phenoxyacetyl group, a 4-isopropylphenoxyacetyl group, a 4-tert-butylphenoxyacetyl group, an acetyl group, a benzoyl group, an isobutyryl group, a dimethylformamidinyl group, a 9-fluorenylmethyloxycarbonyl group and the like. Among them, a phenoxyacetyl group, a 4-isopropylphenoxyacetyl group, an acetyl group, a benzoyl group, an isobutyryl group and a dimethylformamidinyl group are preferable. In addition, the carbonyl group of the nucleic acid base is optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methylsulfonyl)ethanol, 2-(phenylsulfonyl)ethanol, 2-cyanoethanol, 2-(trimethylsilyl)ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride and the like. In some cases, the carbonyl-protecting group does not need to be particularly introduced. Moreover, in addition to the above-mentioned groups, a modified nucleic acid base (e.g., a 8-bromoadenyl group, a 8-bromoguanyl group, a 5-bromocytosyl group, a 5-iodocytosyl group, a 5-bromouracil group, a 5-iodouracil group, a 5-fluorouracil group, a 5-methylcytosyl group, a 8-oxoguanyl group, a hypoxanthinyl group etc.), which is a nucleic acid base substituted by any 1 to 3 substituents (e.g., a halogen atom, an alkyl group, an aralkyl group, an alkoxy group, an acyl group, an alkoxyalkyl group, a hydroxy group, an amino group, monoalkylamino, dialkylamino, carboxy, cyano, nitro etc.) at any position(s), are also encompassed in the "nucleic acid base".

In the present specification, the "halogen atom" means a fluorine atom, a chlorine atom, a bromine atom or iodine atom.

In the present specification, examples of the "alkyl (group)" include a linear or branched chain alkyl group having one or more carbon atoms. When the carbon number is not particularly limited, it is preferably a $C_{1-10}$ alkyl group, more preferably a $C_{1-6}$ alkyl group. When the carbon number is not particularly limited, for example, methyl, ethyl, propyl, isopropyl, butyl, isobutyl, sec-butyl, tert-butyl, pentyl, hexyl and the like are preferable, and methyl and ethyl are particularly preferable.

In the present specification, the "aralkyl (group)" means a $C_{7-20}$ aralkyl group, preferably a $C_{7-16}$ aralkyl group ($C_{6-10}$ aryl-$C_{1-6}$ alkyl group). Specific preferable examples include benzyl, 1-phenylethyl, 2-phenylethyl, 1-phenylpropyl, naphthylmethyl, 1-naphthylethyl, 1-naphthylpropyl and the like, and benzyl is particularly preferable.

In the present specification, examples of the "alkoxy (group)" include an alkoxy group having one or more carbon atoms. When the carbon number is not particularly limited, it is preferably a $C_{1-10}$ alkoxy group, more preferably a $C_{1-6}$ alkoxy group. When the carbon number is not particularly limited, methoxy, ethoxy, propoxy, isopropoxy, butoxy, isobutoxy, sec-butoxy, tert-butoxy, pentyloxy, hexyloxy and the like are preferable, and methoxy and ethoxy are particularly preferable.

In the present specification, examples of the "acyl (group)" include a linear or branched chain $C_{1-6}$ alkanoyl group, a $C_{7-13}$ aroyl group and the like. Specific examples thereof include formyl, acetyl, n-propionyl, isopropionyl, n-butyryl, isobutyryl, pivaloyl, valeryl, hexanoyl, benzoyl, naphthoyl, levulinoyl and the like, each of which is optionally substituted.

In the present specification, examples of the "alkenyl (group)" include a linear or branched chain $C_{2-6}$ alkenyl group and the like. Examples thereof include vinyl, 1-propenyl, allyl, isopropenyl, butenyl, isobutenyl and the like. Among them, a $C_2$-$C_4$ alkenyl group is preferable.

In the present specification, preferable examples of the "alkynyl (group)" include a $C_{2-6}$ alkynyl group and the like. Examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Among them, a $C_2$-$C_4$ alkynyl group is preferable.

In the present specification, the "cycloalkyl (group)" means a cyclic alkyl group, and examples thereof include cyclopropyl, cyclobutyl, cyclopentyl, cyclohexyl, cycloheptyl, cyclooctyl and the like. Among them, a $C_3$-$C_6$ cycloalkyl group such as cyclopropyl, cyclobutyl, cyclopentyl, cyclohexyl and the like is preferable, and cyclohexyl is particularly preferable.

In the present specification, the "aryl (group)" means a monocyclic aromatic or polycyclic (fused) aromatic hydrocarbon group. Specific examples thereof include a $C_{6-14}$ aryl group such as phenyl, 1-naphthyl, 2-naphthyl, biphenylyl, 2-anthryl and the like, and the like. Among them, a $C_{6-10}$ aryl group is more preferably and phenyl is particularly preferable.

In the present specification, examples of the "hydrocarbon group" include an aliphatic hydrocarbon group, an aromatic-aliphatic hydrocarbon group, a monocyclic saturated hydrocarbon group, an aromatic hydrocarbon group and the like, and specific examples thereof include monovalent groups such as an alkyl group, an alkenyl group, an alkynyl group, a cycloalkyl group, an aryl group, an aralkyl group and the like and a divalent group induced therefrom.

In the present specification, the "organic group having a hydrocarbon group" means a group having the aforementioned "hydrocarbon group", and the moiety other than the "hydrocarbon group" of the "organic group having a hydrocarbon group" can be determined freely. For example, the organic group optionally has, as a linker, a moiety such as —O—, —S—, —COO—, —OCONH—, —CONH— and the like.

In the present specification, the "substituent" of the "optionally substituted" encompasses the aforementioned halogen atom, alkyl group, aralkyl group, alkoxy group, acyl group, alkenyl group, alkynyl group, cycloalkyl group, aryl group, as well as hydroxy group, nitro group, cyano group, guanidyl group, carboxy group, alkoxycarbonyl group (the alkoxy moiety is the same as that in the aforementioned alkoxy group), sulfo group, phospho group, alkylthio group (the alkyl moiety is the same as that in the aforementioned alkyl group), alkylsulfinyl group (the alkyl moiety is the same as that in the aforementioned alkyl group), alkylsulfonyl group (the alkyl moiety is the same as that in the aforementioned alkyl group), amino group, monoalkylamino group (the alkyl moiety is the same as that in the aforementioned alkyl group), dialkylamino group (the alkyl moiety is the same as that in the aforementioned alkyl group), oxo group and the like.

[Morpholino Nucleotide Wherein 5'-hydroxy Group or Hydroxy Group Present on the Substituent of the 5'-hydroxy Group is Protected by a Particular Protecting Group, and Morpholine Ring Nitrogen Atom is Optionally Protected by a Temporary Protecting Group Removable Under Acidic Conditions]

Using the morpholino nucleotide wherein 5'-hydroxy group or hydroxy group present on the substituent of the 5'-hydroxy group is protected by a particular protecting group used in the present invention, a production method of a morpholino oligonucleotide suitable for liquid phase synthesis can be provided.

Since high efficiency and high yield can be achieved in the production method of the object morpholino oligonucleotide, a morpholino nucleotide wherein 5'-hydroxy group or hydroxy group present on the substituent of the 5'-hydroxy group is protected by a protecting group having an alkyl group having not less than 10 and not more than 300 carbon atoms and/or an alkenyl group having not less than 10 and not more than 300 carbon atoms is preferable.

"When the 5'-hydroxy group has a substituent" means that the hydrogen atom of the 5'-hydroxy group is substituted by a substituent having a hydroxy group. The "substituent" of the "substituent having a hydroxy group" is not particularly limited as long as the main chain is constituted of 1 to 20 atoms. Here, the "main chain" means a shortest atom chain linking the oxygen atom of the 5'-hydroxy group and the oxygen atom of the hydroxy group on the substituent, and the atom chain is optionally further substituted. The atom constituting the main chain is selected from carbon atom, oxygen atom, nitrogen atom, sulfur atom, phosphorus atom and the like. Specific examples of the "substituent having a hydroxy group" include organic groups having a hydrocarbon group such as alkyl group, aralkyl group, acyl group, alkenyl group, alkynyl group, cycloalkyl group, aryl group, alkoxycarbonyl group and the like, wherein the hydrogen atom on the hydrocarbon group is substituted by a hydroxy group and the like. In addition, for example, the substituent of the following 5'-hydroxy group disclosed in WO 2008/008113 and the like can be mentioned.

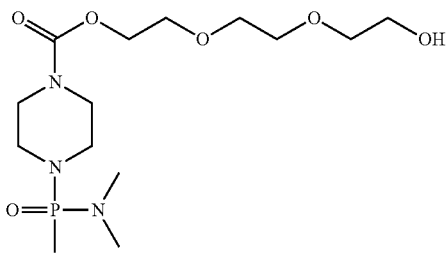 [SMILES: CN(C)P(C)(=O)N1CCN(C(=O)OCCOCCOCCO)CC1]

Examples of the "alkyl group having not less than 10 and not more than 300 carbon atoms and/or alkenyl group having not less than 10 and not more than 300 carbon atoms" include monovalent groups and divalent groups induced therefrom. Among them, alkyl group having 10-40 carbon atoms is preferable, and alkyl group having 10-30 carbon atoms is particularly preferable. The alkyl group and the alkenyl group of the "alkyl group having not less than 10 and not more than 300 carbon atoms and/or alkenyl group having not less than 10 and not more than 300 carbon atoms" include linear or branched chain alkyl group, and linear or branched chain alkenyl group. In the production method of the present invention, linear alkyl group and linear alkenyl group are preferable, and linear alkyl group is particularly preferable. Specific preferable examples of the "alkyl group having not less than 10 and not more than 300 carbon atoms and/or alkenyl group having not less than 10 and not more than 300 carbon atoms" include monovalent aliphatic hydrocarbon group such as decyl group, dodecyl group, tridecyl group, myristyl group, cetyl group, stearyl group, oleyl group, linolyl group, arachyl group, behenyl group, isostearyl group and the like, and divalent groups induced therefrom.

As the morpholino oligonucleotide wherein a 5'-hydroxy group or a hydroxy group present on a substituent of the 5'-hydroxy group is protected by a protecting group having an alkyl group having not less than 10 and not more than 300 carbon atoms and/or an alkenyl group having not less than 10 and not more than 300 carbon atoms, and the morpholine ring nitrogen atom is optionally protected by a temporary protecting group removable under acidic conditions, a morpholino nucleotide wherein the 5'-hydroxy group or the hydroxy group present on the substituent of the 5'-hydroxy group is protected by a protecting group represented by the formula (II): Z—Y—L- is preferable. Specifically, a novel compound represented by the following formula (I) (hereinafter sometimes to be referred to as the compound of the present invention) can be mentioned.

The formula (I):

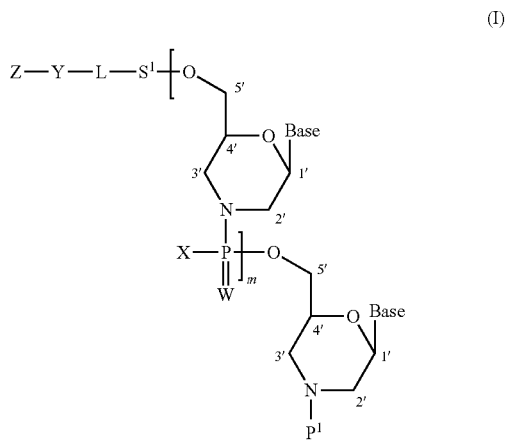

[wherein
m is any integer of not less than 0,
Base in the number of m+1 are each independently an optionally protected nucleic acid base,
$P^1$ is a hydrogen atom, or a temporary protecting group removable under acidic conditions,
X in the number of m are each independently a $C_{1-6}$ alkoxy group, a di-$C_{1-6}$ alkylamino group, or a piperazino group wherein a nitrogen atom at the 4-position is protected by a protecting group and further optionally substituted,
W in the number of m are each independently an oxygen atom or a sulfur atom,
$S^1$ is a single bond, or a group represented by *O—$S^2$** (wherein * indicates the bonding position to L, ** indicates the bonding position to 5'-hydroxy group, and $S^2$ is a spacer having a main chain containing 1 to 20 atoms), and
L is a single bond, or a group represented by the formula (a1):

[wherein * indicates the bonding position to Y;
** indicates the bonding position to $S^1$;
$L_1$ is an optionally substituted divalent $C_{1-22}$ hydrocarbon group; and
$L_2$ is C(=O) or a group represented by *N($R^3$)—$R^1$—N($R^2$)C(=O) (wherein  indicates the bonding position to $L^1$, * indicates the bonding position to Y, $R^1$ is an optionally substituted $C_{1-22}$ alkylene group, $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond)],
Y is a single bond, an oxygen atom or NR (wherein R is a hydrogen atom, an alkyl group or an aralkyl group), and Z is a group represented by the formula (a2):

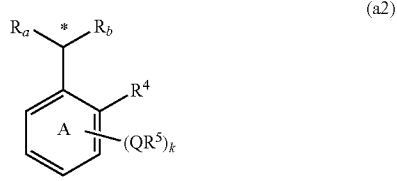

[wherein * indicates the bonding position to Y;
R⁴ is a hydrogen atom, or when R_b is a group represented by the following formula (a3), R⁴ is optionally a single bond or —O— in combination with R⁶ to form a fluorenyl group or a xanthenyl group together with ring B;
Q in the number of k are each independently a single bond, or —O—, —S—, —OC(=O)—, —NHC(=O)— or —NH—;
R⁵ in the number of k are each independently an organic group having an alkyl group having not less than 10 and not more than 300 carbon atoms and/or an alkenyl group having not less than 10 and not more than 300 carbon atoms;
k is an integer of 1 to 4;
ring A optionally further has, in addition to QR⁵ in the number of k, a substituent selected from the group consisting of a halogen atom, a $C_{1-6}$ alkyl group optionally substituted by a halogen atom(s), and a $C_{1-6}$ alkoxy group optionally substituted by a halogen atom(s);
R_a is a hydrogen atom;
R_b is a hydrogen atom, or a group represented by the formula (a3):

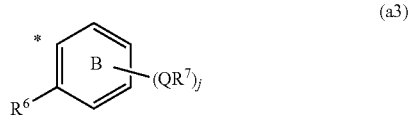

(wherein * indicates a bonding position;
j is an integer of 0 to 4;
Q in the number of j are as defined above;
R⁷ in the number of j are each independently an organic group having an alkyl group having not less than 10 and not more than 300 carbon atoms and/or an alkenyl group having not less than 10 and not more than 300 carbon atoms;
R⁶ is a hydrogen atom, or optionally a single bond or —O— in combination with R⁴ to form a fluorenyl group or a xanthenyl group together with ring A; and
ring B optionally further has, in addition to QR⁷ in the number of j, a substituent selected from the group consisting of a halogen atom, a $C_{1-6}$ alkyl group optionally substituted by a halogen atom(s), and a $C_{1-6}$ alkoxy group optionally substituted by a halogen atom(s)), or
R_a and R_b are optionally joined to form an oxygen atom.]]

In the below-mentioned production method of the morpholino oligonucleotide of the present invention, the 5'-hydroxy group is activated (thio)phosphated or activated (thio)phosphoramidated, and the morpholine ring nitrogen atom is bonded to p-mer morpholino oligonucleotide (p is any integer of one or more) protected by a temporary protecting group removable under acidic conditions, whereby the compound of the present invention can form m+1+p-mer morpholino oligonucleotide (p is any integer of one or more).

When m is 0, the compound of the present invention is understood to be a "morpholino nucleoside", which is a starting compound of the 5'-terminal in the synthesis of the morpholino oligonucleotide of the present invention. In addition, the compound of the present invention also encompasses one wherein the morpholine ring nitrogen atom on the 3'-terminus side is unprotected (P¹ is a hydrogen atom) in a broad sense.

In the above-mentioned formula (I), m is any integer of not less than 0, preferably, 0. While the upper limit of m is not particularly limited, it is preferably 49 or less, more preferably 29 or less, further preferably 19 or less.

Base in the number of m+1 in the above-mentioned formula (I) are each independently an optionally protected nucleic acid base. The "optionally protected nucleic acid base" means, for example, that an amino group may be protected in an adenyl group, a guanyl group or a cytosyl group, which is a nucleic acid base having an amino group, or imide group is optionally protected in a thyminyl group, an uracil group having a cyclic imide group, and a nucleic acid base wherein the amino group therein is protected by a protecting group sustainable under the deprotection conditions of the morpholine ring nitrogen atom is preferable. The protecting group of the "amino-protecting group" and the "imido-protecting group" is not particularly limited and, for example, any protecting groups described in Greene's PROTECTIVE GROUPS IN ORGANIC SYNTHESIS, 4th ed., JOHN WILLY&SONS (2006) and the like can be mentioned. Specific examples of such "amino-protecting group" and "imide-protecting group" include a pivaloyl group, a pivaloyloxymethyl group, a trifluoroacetyl group, a phenoxyacetyl group, a 4-isopropylphenoxyacetyl group, a 4-tert-butylphenoxyacetyl group, an acetyl group, a benzoyl group, an isobutyryl group, a dimethylformamidinyl group, a 9-fluorenylmethyloxycarbonyl group and the like. Among them, a phenoxyacetyl group, a 4-isopropylphenoxyacetyl group, an acetyl group, a benzoyl group, an isobutyryl group and a dimethylformamidinyl group are preferable. In addition, the carbonyl group of the nucleic acid base is optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methylsulfonyl)ethanol, 2-(phenylsulfonyl)ethanol, 2-cyanoethanol, 2-(trimethylsilyl)ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride and the like. In some cases, the carbonyl-protecting group does not particularly need to be introduced.

The temporary protecting group P¹ that can be used as the protecting group of the morpholine ring nitrogen atom at the 3'-terminus of the present invention is not particularly limited as long as it can be deprotected under acidic conditions and can be used as a hydroxy-protecting group. Examples thereof include a trityl group, 9-(9-phenyl)xanthenyl group, a 9-phenylthioxanthenyl group, di($C_{1-6}$ alkoxy)trityl groups such as a 1,1-bis(4-methoxyphenyl)-1-phenylmethyl group, a dimethoxytrityl group and the like, mono($C_{1-18}$ alkoxy) trityl groups such as 1-(4-methoxyphenyl)-1,1-diphenylmethyl group, monomethoxytrityl group and the like, and the like can be mentioned. Among these, a trityl group, a monomethoxytrityl group and a dimethoxytrityl group are preferable, and a dimethoxytrityl group is more preferable, in view of easiness of deprotection and easy availability.

Among these, a trityl group, a monomethoxytrityl group and a dimethoxytrityl group are preferable, and a trityl group and a dimethoxytrityl group are more preferable, in view of easiness of deprotection and easy availability.

In the above-mentioned formula (I), X in the number of m are each independently a $C_{1-6}$ alkoxy group, a di-$C_{1-6}$ alkylamino group, or a piperazino group wherein a nitrogen atom at the 4-position is protected by a protecting group and further optionally substituted, preferably a di-$C_{1-6}$ alkylamino group.

As the $C_{1-6}$ alkoxy group, a methoxy group or an ethoxy group is preferable, and a methoxy group is more preferable.

As the di-$C_{1-6}$ alkylamino group, a dimethylamino group, a diethylamino group, an N-ethyl-N-methylamino group and the like are preferable, and a dimethylamino group is preferable.

As the protecting group of the 4-position nitrogen atom of the piperazino group, an acyl group is preferable and, for example, an acyl group having a fluoro group in the carbon chain, such as a monofluoroacetyl group, a difluoroacetyl group, a trifluoroacetyl group, a 2-fluoropropionyl group, a 2,2-difluoropropionyl group, a 3,3,3-trifluoropropionyl group, a 2,3,3,3-tetrafluoropropionyl group, a pentafluoropropionyl group and the like, is more preferable. While the protecting group is generally deprotected after completion of the elongation reaction, the amino group of the piperazino group may be further modified, after deprotection, by a modifying group according to the method described in WO 2008/008113. Examples of the modifying group include a halogen atom, an alkyl group, an aralkyl group, an alkoxy group, an acyl group, an alkenyl group, an alkynyl group, a cycloalkyl group, an aryl group, a hydroxy group, a nitro group, a cyano group, a guanidyl group, a carboxy group, an alkoxycarbonyl group, a sulfo group, a phospho group, an alkylthio group, an alkylsulfinyl group, an alkylsulfonyl group and the like. As the modifying group of the piperazino group, an optionally substituted acyl group is preferable, and an acyl group (e.g., 6-guanidinohexanoyl group) optionally substituted by a guanidyl group is more preferable. In the piperazino group, the hydrogen atom bonded to the carbon atom of the piperazino group may be substituted, and examples of the substituent include an alkyl group (preferably having 1-3 carbon atoms) such as a methyl group and the like, and the like.

W in the number of m is each independently an oxygen atom or a sulfur atom, preferably an oxygen atom.

$S^1$ in the above-mentioned formula (I) is a single bond, or a group represented by *O—$S^2$** (wherein * indicates the bonding position to L, ** indicates the bonding position to 5'-hydroxy group, and $S^2$ is a spacer having a main chain containing 1 to 20 atoms), preferably a single bond.

The "spacer having a main chain having an atomic number of 1 to 20" for $S^2$ is, for example, a divalent group formed by removing a hydroxy group from the aforementioned "substituent having a hydroxy group" when the 5'-hydroxy group has a substituent.

A preferable embodiment of the linker L represented by the above-mentioned formula (a1) is a group wherein, in the formula (a1),
$L_1$ is an ethylene group or $CH_2$—O-1,4-phenylene-O—$CH_2$; and
$L_2$ is C(=O), or a group represented by *N($R^3$)—$R^1$—N($R^2$)C(=O) (wherein  indicates the bonding position to $L_1$, * indicates the bonding position to Y, $R^1$ is a $C_{1-6}$ alkylene group, and $R^2$ and $R^3$ are each independently a hydrogen atom or an optionally substituted $C_{1-6}$ alkyl group, or $R^2$ and $R^3$ are optionally joined to form an optionally substituted $C_{1-6}$ alkylene bond).

Another preferable embodiment of the linker L represented by the above-mentioned formula (a1) is a group wherein, in the formula (a1),
$L_1$ is an ethylene group; and
$L_2$ is C(=O).

Another preferable embodiment of the linker L represented by the above-mentioned formula (a1) is a group wherein, in the formula (a1),
$L_1$ is an ethylene group; and
the moiety of N($R^3$)—$R^1$—N($R^2$) for $L_2$ is a piperazinylene group.

Another preferable embodiment of the linker L represented by the above-mentioned formula (a1) is a group wherein, in the formula (a1),
$L_1$ is an ethylene group; and
$L_2$ is a group represented by *N($R^3$)—$R^1$—N($R^2$) C(=O) (wherein  indicates the bonding position to $L^1$, * indicates the bonding position to Y, $R^1$ is a pentylene group or a hexylene group, and $R^2$ and $R^3$ are each independently a hydrogen atom or a methyl group).

A particularly preferable example of the above-mentioned linker L is a single bond or a succinyl group since it is easily available and economical.

Y in the above-mentioned formula (I) is a single bond, an oxygen atom, or NR (wherein R is a hydrogen atom, an alkyl group or an aralkyl group).

In the present specification, the "alkyl group" for R is a $C_{1-30}$ alkyl group, preferably a $C_{1-10}$ alkyl group, more preferably a $C_{1-6}$ alkyl group. Specific preferable examples thereof include methyl, ethyl, propyl, isopropyl, butyl, isobutyl, sec-butyl, tert-butyl and the like, and methyl and ethyl are particularly preferable.

In the present specification, the "aralkyl group" for R is a $C_{7-30}$ aralkyl group, preferably a $C_{7-20}$ aralkyl group, more preferably a $C_{7-16}$ aralkyl group ($C_{6-10}$ aryl-$C_{1-5}$ alkyl group). Specific preferable examples thereof include benzyl, 1-phenylethyl, 2-phenylethyl, 1-phenylpropyl, α-naphthylmethyl, 1-(α-naphthyl)ethyl, 2-(α-naphthyl)ethyl, 1-(α-naphthyl)propyl, β-naphthylmethyl, 1-(β-naphthyl)ethyl, 2-(β-naphthyl)ethyl, 1-(β-naphthyl)propyl and the like, and benzyl is particularly preferable.

R is preferably a hydrogen atom, a $C_{1-6}$ alkyl group or a $C_{7-16}$ aralkyl group, more preferably a hydrogen atom, methyl, ethyl or benzyl, particularly preferably a hydrogen atom.

Y is preferably a single bond, an oxygen atom or NH.

A preferable embodiment of Z is a group represented by the formula (a2).

The preferable embodiment for Z in the above-mentioned formula (I), that is, a group represented by the formula (a2) for Z in the above-mentioned formula (I) is a particular benzyl group (in the formula (a2), both $R_a$ and $R_b$ are hydrogen atoms, and $R^4$ is a hydrogen atom); a particular benzoyl group (in the formula (a2) wherein $R_a$ and $R_b$ are joined to form an oxygen atom, and $R^4$ is a hydrogen atom); a particular diphenylmethyl group (in the formula (a2), $R_a$ is a hydrogen atom, $R^4$ is a hydrogen atom, k is 1 to 3, and $R_b$ is a group represented by the formula (a3) (wherein $R^6$ is a hydrogen atom, and j is 0 or 1)); a particular fluorenyl group (in the formula (a2), $R_a$ is a hydrogen atom, k is 1, $R_b$ is a group represented by the formula (a3) (wherein j is 0)), and $R^6$ is a single bond together with $R^4$ to form a fluorene ring together with ring A); a particular xanthenyl group (in the formula (a2), $R_a$ is a hydrogen atom, k is 1, $R_b$ is a group represented by the formula (a3) (wherein j is 0), and $R^6$ is —O— together with $R^4$ to form a xanthine ring together with ring A).

In the $QR^5$ group in the number of k in the above-mentioned formula (a2), and the $QR^7$ group in the number of j in the formula (a3), Q is a single bond, or —O—, —S—, —OC(=O)—, —NHC(=O)— or —NH—, preferably —O—. The $QR^5$ group in the number of k, and $QR^7$ group in the number of j may be the same or different.

In the above-mentioned formula (a2), the "$R_a$ and $R_b$ are joined to form an oxygen atom" means that $R_a$ and $R_b$ are joined to form a carbonyl group (C(=O)).

The "organic group having an alkyl group having not less than 10 and not more than 300 carbon atoms and/or an alkenyl group having not less than 10 and not more than 300 carbon atoms" for $R^5$ or $R^7$ is a monovalent organic group having an alkyl group having not less than 10 and not more than 300 carbon atoms and/or an alkenyl group having not less than 10 and not more than 300 carbon atoms in the molecule structure thereof.

The carbon number of the "alkyl group having not less than 10 and not more than 300 carbon atoms and/or alkenyl group having not less than 10 and not more than 300 carbon atoms" of the "organic group having an alkyl group having not less than 10 and not more than 300 carbon atoms and/or an alkenyl group having not less than 10 and not more than 300 carbon atoms" is preferably 14-40, more preferably 14-30.

The moiety of the "alkyl group having not less than 10 and not more than 300 carbon atoms and/or alkenyl group having not less than 10 and not more than 300 carbon atoms" of the "organic group having an alkyl group having not less than 10 and not more than 300 carbon atoms and/or an alkenyl group having not less than 10 and not more than 300 carbon atoms" is not particularly limited, and it may be present at the terminus (monovalent group), or the other site (e.g., divalent group).

As the "alkyl group having not less than 10 and not more than 300 carbon atoms and/or alkenyl group having not less than 10 and not more than 300 carbon atoms", a monovalent group and a divalent group induced therefrom can be mentioned. Among them, an alkyl group having 14-40 carbon atoms is preferable, and an alkyl group having 14-30 carbon atoms is particularly preferable. Specific examples of the "alkyl group having not less than 10 and not more than 300 carbon atoms and/or alkenyl group having not less than 10 and not more than 300 carbon atoms" include monovalent linear aliphatic hydrocarbon groups such as a decyl group, a dodecyl group, a tridecyl group, a myristyl group, a cetyl group, a stearyl group, an oleyl group, a linolyl group, an arachyl group, a behenyl group and the like, monovalent branched chain aliphatic hydrocarbon groups such as a 3,7,11,15-tetramethylhexadecyl group, a 3,7,11-trimethyldodecyl group, a 2,2,4,8,10,10-hexamethyl-5-dodecanoyl group and the like, and divalent groups induced therefrom.

In the "organic group having an alkyl group having not less than 10 and not more than 300 carbon atoms and/or an alkenyl group having not less than 10 and not more than 300 carbon atoms", the moiety other than the "alkyl group having not less than 10 and not more than 300 carbon atoms and/or alkenyl group having not less than 10 and not more than 300 carbon atoms" can be determined freely. For example, it optionally has a moiety such as —O—, —S—, —COO—, —OCONH—, and —CONH—, and a hydrocarbon group (monovalent group or divalent group) and the like as a linker. Examples of the "hydrocarbon group" include an aliphatic hydrocarbon group, an aromatic aliphatic hydrocarbon group, a monocyclic saturated hydrocarbon group, an aromatic hydrocarbon group and the like. Specifically, for example, monovalent groups such as an alkyl group, an alkenyl group, an alkynyl group, a cycloalkyl group, an aryl group, an aralkyl group and the like, and divalent groups derived therefrom are used. As "alkyl group", "alkenyl group", "alkynyl group", "cycloalkyl group", "aryl group", or "aralkyl group" as the moiety other than "aliphatic hydrocarbon group", those similar to the aforementioned groups can be mentioned. The "hydrocarbon group" is optionally substituted by a substituent selected from a halogen atom (chlorine atom, bromine atom, fluorine atom, iodine atom), a $C_{1-6}$ alkyl group optionally substituted by one or more halogen atoms, an oxo group and the like.

The "organic group having an alkyl group having not less than 10 and not more than 300 carbon atoms and/or an alkenyl group having not less than 10 and not more than 300 carbon atoms" indicated as "$R^5$ (group)" and/or "$R^7$ (group)" constituting Z in the above-mentioned formula (I) may contain plural "alkyl groups having not less than 10 and not more than 300 carbon atoms and/or alkenyl groups having not less than 10 and not more than 300 carbon atoms" due to branching and the like. When a plurality of "alkyl group having not less than 10 and not more than 300 carbon atoms and/or alkenyl group having not less than 10 and not more than 300 carbon atoms" is present in the "organic group having an alkyl group having not less than 10 and not more than 300 carbon atoms and/or an alkenyl group having not less than 10 and not more than 300 carbon atoms", they may be the same or different.

The lower limit of the total carbon number of the "organic group having an alkyl group having not less than 10 and not more than 300 carbon atoms and/or an alkenyl group having not less than 10 and not more than 300 carbon atoms" for "$R^5$ (group)" and/or "$R^7$ (group)" constituting Z in the above-mentioned formula (II) is preferably 10 or more, more preferably 12 or more, further preferably 14 or more, still more preferably 18 or more, and particularly preferably 30 or more. On the other hand, the upper limit of the total carbon number of the "organic group having a an alkyl group having not less than 10 and not more than 300 carbon atoms and/or an alkenyl group having not less than 10 and not more than 300 carbon atoms" for "$R^5$(group)" and/or "$R^7$(group)" is preferably 200 or less, more preferably 150 or less, further preferably 120 or less, still more preferably 100 or less, especially preferably 80 or less, and particularly preferably 60 or less.

When the carbon number is higher, the crystallinity or solubility of the compound of the present invention in a polar solvent is fine even when the morpholino oligonucleotide has a long chain.

A preferable embodiment of Z represented by the above-mentioned formula (a2) is a group represented by the formula (a2), wherein, in the formula (a2),
$R_a$ and $R_b$ are both hydrogen atoms;
$R^4$ is a hydrogen atom,
Q in the number of k is —O—,
$R^5$ in the number of k are each independently an organic group having an alkyl group having not less than 10 and not more than 300 carbon atoms and/or an alkenyl group having not less than 10 and not more than 300 carbon atoms (e.g., $C_{10-40}$ alkyl group); and
k is an integer of 1-3.

Another preferable embodiment of Z represented by the above-mentioned formula (a2) is a group wherein, in the formula (a2), k is an integer of 1-3;
$R_a$ and $R_b$ are both hydrogen atoms;
$R^4$ is a hydrogen atom,
Q in the number of k is —O—,
$R^5$ in the number of k are each independently a benzyl group having 1-3 alkyl groups having not less than 10 and not more than 300 carbon atoms and/or alkenyl groups having not less than 10 and not more than 300 carbon atoms, or a cyclohexyl group having 1-3 alkyl groups having not less than 10 and not more than 300 carbon atoms and/or alkenyl groups having not less than 10 and not more than 300 carbon atoms; and
ring A optionally further has, in addition to $QR^5$ in the number of k, substituent(s) selected from the group consisting of a halogen atom, a $C_{1-6}$ alkyl group optionally substituted by a halogen atom, and a $C_{1-6}$ alkoxy group optionally substituted by a halogen atom.

Another preferable embodiment of Z represented by the above-mentioned formula (a2) is a group wherein, in the formula (a2),
$R_a$ is a hydrogen atom; and
$R_b$ is a group represented by the above-mentioned formula (a3) (wherein * indicates a bonding position; j is an integer of 0 to 3; Q in the number of j is —O—; $R^7$ in the number of j are each independently a $C_{10-40}$ alkyl group; and $R^4$ and $R^6$ are both hydrogen atoms.

A still another preferable embodiment of Z represented by the above-mentioned formula (a2) is a group wherein, in the formula (a2),
$R_a$ is a hydrogen atom;
$R_b$ is a group represented by the above-mentioned formula (a3) (wherein * indicates a bonding position; j is an integer of 0 to 3; Q in the number of j is —O—; $R^7$ in the number of j are each independently a $C_{10-40}$ alkyl group;
$R^6$ is joined with $R^4$ of ring A to form a single bond or —O—, and therefore, ring A and ring B form a fluorenyl group or a xanthenyl group in combination.

Another preferable embodiment of Z represented by the above-mentioned formula (a2) is a group wherein, in the formula (a2),
$R_a$ and $R_b$ are joined to form an oxygen atom;
$R^4$ is a hydrogen atom,
Q in the number of k is —O—,
$R^5$ in the number of k are each independently an organic group having an alkyl group having not less than 10 and not more than 300 carbon atoms and/or an alkenyl group having not less than 10 and not more than 300 carbon atoms (e.g., $C_{10-40}$ alkyl group); and
k is an integer of 1-3.

Another preferable embodiment of Z represented by the above-mentioned formula (a2) is a group wherein, in the formula (a2),
k is an integer of 1-3;
$R_a$ and $R_b$ are joined to form an oxygen atom;
$R^4$ is a hydrogen atom;
Q in the number of k is —O—,
$R^5$ in the number of k are each independently a benzyl group having 1-3 alkyl groups having not less than 10 and not more than 300 carbon atoms and/or alkenyl groups having not less than 10 and not more than 300 carbon atoms, or a cyclohexyl group having 1-3 alkyl groups having not less than 10 and not more than 300 carbon atoms and/or alkenyl groups having not less than 10 and not more than 300 carbon atoms; and ring A optionally further has, in addition to $QR^5$ in the number of k, substituent(s) selected from the group consisting of a halogen atom, a $C_{1-6}$ alkyl group optionally substituted by a halogen atom(s), and a $C_{1-6}$ alkoxy group optionally substituted by a halogen atom(s).

As the protecting group represented by the formula (II): Z—Y-L-, a group not easily cleaved under acidic conditions under which the protecting group $P^1$ of the morpholine ring nitrogen atom at the 3'-terminus can be removed, and cleaved under basic conditions is preferable.

Representative examples of the protecting group include a group wherein, for example,
L is a group represented by the above-mentioned formula (a1) (preferably a succinyl group etc.), and
Z—Y is the following group:
a 3,4,5-tri(octadecyloxy)benzyloxy group,
a 3,5-di(docosyloxy)benzyloxy group,
a 3,5-bis[3',4',5'-tri(octadecyloxy)benzyloxy]benzyloxy group,
a 3,4,5-tris[3',4',5'-tri(octadecyloxy)benzyloxy]benzyloxy group,
a 3,4,5-tri(octadecyloxy)benzylamino group,
a 2,4-di(docosyloxy)benzylamino group,
a 3,5-di(docosyloxy)benzylamino group,
a di(4-docosyloxyphenyl)methylamino group,
a 4-methoxy-2-[3',4',5'-tri(octadecyloxy)benzyloxy]benzylamino group,
a 4-methoxy-2-[3',4',5'-tri(octadecyloxy)cyclohexylmethyloxy]benzylamino group,
a 2,4-di(dodecyloxy)benzylamino group,
a phenyl(2,3,4-tri(octadecyloxy)phenyl)methylamino group,
a di[4-(12-docosyloxydodecyloxy)phenyl]methylamino group,
a 3,5-bis[3',4',5'-tri(octadecyloxy)benzyloxy]benzylamino group, or
a 3,4,5-tris[3',4',5'-tri(octadecyloxy)benzyloxy]benzylamino group.

As another embodiment of the protecting group Z—Y-L-, the following benzylsuccinyl groups and diphenylmethylsuccinyl groups can be mentioned.
a 2-{2,4-di(2',3'-dihydrophytyloxy)benzylaminocarbonyl}ethylcarbonyl group;
a 3,5-di(2',3'-dihydrophytyloxy)benzylsuccinyl group;
a 4-(2',3'-dihydrophytyloxy)benzylsuccinyl group;
a 2-{1-[(2-chloro-5-(2',3'-dihydrophytyloxy)phenyl)]benzylaminocarbonyl}ethylcarbonyl group;
a 3,4,5-tri(2',3'-dihydrophytyloxy)benzylsuccinyl group;
a 2-{3,4,5-tri(2',3'-dihydrophytyloxy)benzylaminocarbonyl}ethylcarbonyl group;
a 2-{4-(2',3'-dihydrophytyloxy)benzylaminocarbonyl}ethylcarbonyl group;
a 2-{2-[3',4',5'-tri(2",3"-dihydrophytyloxy)benzyloxy]-4-methoxybenzylaminocarbonyl}ethylcarbonyl group;
a 2-{4-(2',3'-dihydrophytyloxy)-2-methoxybenzylaminocarbonyl}ethylcarbonyl group;
a 4-(2',3'-dihydrophytyloxy)-2-methylbenzylsuccinyl group;
a 2-{4-(2',3'-dihydrophytyloxy)-2-methylbenzylaminocarbonyl}ethylcarbonyl group;
a 4-[2,2,4,8,10,10-hexamethyl-5-dodecanoylamino]benzylsuccinyl group;
a 2-{4-[2,2,4,8,10,10-hexamethyl-5-dodecanoylamino]benzylaminocarbonyl}ethylcarbonyl group;
a 4-(3,7,11-trimethyldodecyloxy)benzylsuccinyl group;
a 2-{4-(3,7,11-trimethyldodecyloxy)benzylaminocarbonyl}ethylcarbonyl group;
a 2-{3,5-di(2',3'-dihydrophytyloxy)benzylaminocarbonyl}ethylcarbonyl group;
a 2-{1-[2,3,4-tri(2',3'-dihydrophytyloxy)phenyl]benzylaminocarbonyl}ethylcarbonyl group;

a 2-{1-[4-(2',3'-dihydrophytyloxy)phenyl]-4'-(2',3'-dihydrophytyloxy)benzylaminocarbonyl}ethylcarbonyl group;

a 3,4,5-tris[3,4,5-tri(2',3'-dihydrophytyloxy)benzyl]benzylsuccinyl group; and a 2-{3,4,5-tris[3,4,5-tri(2',3'-dihydrophytyloxy)benzyl]benzylaminocarbonyl}ethylcarbonyl group.

Another embodiment of the protecting group represented by the formula (II): Z—Y-L- is a group wherein
L and Y are each a single bond,
Z shows the formula (a2),
$R_a$ and $R_b$ are joined to form an oxygen atom;
$R^4$ is a hydrogen atom,
Q in the number of k is —O—,
$R^5$ in the number of k are each independently an organic group having an alkyl group having not less than 10 and not more than 300 carbon atoms and/or an alkenyl group having not less than 10 and not more than 300 carbon atoms (e.g., $C_{10-40}$ alkyl group); and
k is an integer of 1-3.

Another embodiment of the protecting group represented by the formula (II): Z—Y-L- is a group wherein
L shows the formula (a1),
$L_2$ is *N($R^3$)—$R^1$—N($R^2$)C(=O) (wherein  indicates the bonding position to $L^1$, * indicates the bonding position to Y, $R^1$ is an optionally substituted $C_{1-22}$ alkylene group, $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond),
Y is a single bond,
Z shows the formula (a2),
$R_a$ and $R_b$ are joined to form an oxygen atom;
$R^4$ is a hydrogen atom,
Q in the number of k is —O—,
$R^5$ in the number of k are each independently an organic group having an alkyl group having not less than 10 and not more than 300 carbon atoms and/or an alkenyl group having not less than 10 and not more than 300 carbon atoms (e.g., $C_{10-40}$ alkyl group); and
k is an integer of 1-3.

A preferable embodiment of the compound of the present invention represented by the formula (I) is a compound of the formula (I), wherein
m is 0,
Base is a cytosyl group, a uracil group, a thyminyl group, an adenyl group, or a guanyl group, each of which is optionally protected;
$P^1$ is a trityl group, a di($C_{1-6}$ alkoxy)trityl group or a mono($C_{1-6}$ alkoxy)trityl group;
$S^1$ is a single bond; and
Z—Y-L is the combination of each group shown as a preferable embodiment in the aforementioned formula (I).

Another preferable embodiment of the compound of the present invention represented by the formula (I) is a compound of the formula (I), wherein
m is 0,
Base is a cytosyl group, a uracil group, a thyminyl group, an adenyl group, or a guanyl group, each of which is optionally protected;
$P^1$ is a trityl group, a dimethoxytrityl group or a monomethoxytrityl group;
$S^1$ is a single bond; and
Z—Y-L is the combination of each group shown as a preferable embodiment in the aforementioned formula (I).

A still another preferable embodiment of the compound of the present invention represented by the formula (I) is a compound of the formula (I), wherein m is 0,
Base is a cytosyl group, a uracil group, a thyminyl group, an adenyl group, or a guanyl group, each of which is optionally protected;
$P^1$ is a trityl group;
$S^1$ is a single bond; and
Z—Y-L is the combination of each group shown as a preferable embodiment in the aforementioned formula (I).

[Production Method of the Compound of the Present Invention]

A production method of the compound of the present invention represented by the formula (I) wherein m is 0, and $S^1$ is a single bond (hereinafter to be referred to as "the formula (Ia)") is not particularly limited, and it can be produced by a method known per se (Richard T. Pon et al., Nucleic Acids Research 2004, 32, 623-631) or a method analogous thereto.

A general production method of a compound of the above-mentioned formula (Ia) wherein L is a succinyl group is shown below.

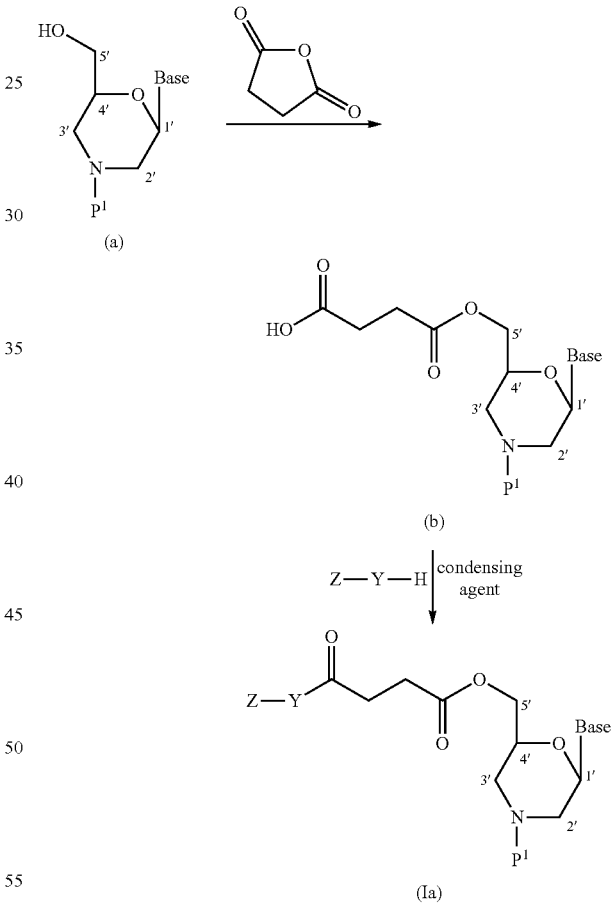

(wherein each symbol is as defined above.)

Morpholino nucleoside (a) wherein the 3'-terminus morpholine ring nitrogen atom is protected by a protecting group $P^1$ is reacted with succinic anhydride in the presence of a base to give compound (b) wherein succinic acid is introduced into the 5'-hydroxy group. Compound (b) is subjected to a dehydration condensation with a precursor (Z—Y—H) (alcohol or amine) of the protecting group in the presence of a condensing agent, whereby a compound represented by the formula (Ia) can be obtained.

The conversion step of the above-mentioned morpholino nucleoside (a) to compound (b) is advantageously performed in a solvent inert to the reaction. While such solvent is not particularly limited as long as the reaction proceeds, halogenated hydrocarbon solvents such as dichloromethane, 1,2-dichloroethane, chloroform, carbon tetrachloride and the like, aromatic hydrocarbon solvents such as benzene, toluene, xylene and the like, aliphatic hydrocarbon solvents such as pentane, hexane, heptane, octane and the like, ether solvents such as diethyl ether, tetrahydrofuran, cyclopentyl methyl ether and the like, and mixed solvents thereof are preferable. Of these, dichloromethane and chloroform are particularly preferable.

While the base is not particularly limited, for example, an organic base mentioned below can be used, with preference given to N,N-dimethylaminopyridine, triethylamine and the like.

The above-mentioned dehydration condensation step is advantageously performed in a solvent inert to the reaction. While such solvent is not particularly limited as long as the reaction proceeds, halogenated hydrocarbon solvents such as dichloromethane, 1,2-dichloroethane, chloroform, carbon tetrachloride and the like, aromatic hydrocarbon solvents such as benzene, toluene, xylene and the like, or aliphatic hydrocarbon solvents such as pentane, hexane, heptane, octane and the like, and mixed solvents thereof are preferable. Of these, dichloromethane and chloroform are particularly preferable.

Examples of the condensing agent used for the condensation reaction of compound (b) with Z—Y—H include dicyclohexylcarbodiimide (DCC), diisopropylcarbodiimide (DIC), N-ethyl-N'-(3-dimethylaminopropyl)carbodiimide and hydrochloride thereof (EDC HCl), (benzotriazol-1-yloxy)tripyrrolidinophosphonium hexafluorophosphate (PyBop), O-(benzotriazol-1-yl)-N,N,N',N'-tetramethyluronium tetrafluoroborate (TBTU), 1-[bis(dimethylamino)methylene]-5-chloro-1H-benzotriazolium-3-oxide hexafluorophosphate (HCTU), O-benzotriazole-N,N,N',N'-tetramethyluronium hexafluorophosphate (HBTU) and the like. Of these, HBTU, HCTU, N-ethyl-N'-(3-dimethylaminopropyl)carbodiimide and hydrochloride thereof (EDC HCl) are preferable.

The amount of the condensing agent to be used is 1 to 10 mol, preferably 1 to 5 mol, per 1 mol of compound (b). The amount of Z—Y—H to be used is 1 to 10 mol, preferably 1 to 5 mol, per 1 mol of compound (b). While the reaction temperature is not particularly limited as long as the reaction proceeds, it is preferably −10° C. to 50° C., more preferably 0° C. to 30° C. The reaction time is 30 min to 70 hr.

A compound of the above-mentioned formula (Ia) wherein L is other than a succinyl group can also be produced by performing a reaction similar to the above-mentioned production method except that a corresponding acid anhydride, a corresponding dicarboxylic acid halide, an activated ester of corresponding dicarboxylic acid and the like is used instead of succinic anhydride.

A compound wherein $S^1$ is *O—$S^{2}$** (wherein each symbol is as defined above) can be produced by introducing the aforementioned "substituent having a hydroxy group" into the 5'-hydroxy group of the morpholino nucleoside (a) by a known method (e.g., the method described in WO 2008/008113) and thereafter following the above-mentioned method.

A compound wherein Y is a single bond can be produced by reacting an activated derivative (halide, acid halide, activated carboxy group etc.) of Z—Y—H with morpholino nucleoside (a) by a method known per se, or reacting Z—Y—H with morpholino nucleoside (a) in the presence of a condensing agent. The condensation reaction of Z—Y—H and morpholino nucleoside (a) can be performed in the same manner as in the condensation reaction of Z—Y—H and compound (b).

A compound of the above-mentioned formula (I) wherein m is one or more can be produced by repeating the 5'-terminus elongation process according to the following production method of the present invention and using a compound represented by the formula (Ia) as a starting material.

While the production method of precursor (Z—Y—H) (alcohol, amine or carboxylic acid) of the aforementioned protecting group is not particularly limited, it can be produced from a starting compound according to a method known per se (e.g., Bull. Chem. Soc. Jpn. 2001, 74, 733-738, JP-A-2000-44493, WO 2006/104166, WO 2007/034812, WO 2007/122847, WO 2010/113939, JP-A-2010-275254, WO 2012/157723 etc.) or a method analogous thereto.

A compound to be used as a starting compound, for example, a halide corresponding to $R^5$ and $R^7$ constituting Z in the formula (I) and the like is a commercially available product, or can be produced according to a method known per se or a method analogous thereto.

The precursor (Z—Y—H) of the protecting group can be produced by a method known per se or a method analogous thereto, as mentioned above. When a starting compound has a substituent (e.g., hydroxy group, amino group, carboxy group) that influences the reaction, the starting compound is generally protected in advance by a suitable protecting group according to a known method and then subjected to the reaction. Such protecting group can be removed after the reaction by a known method such as an acid treatment, an alkali treatment, a catalytic reduction and the like.

While the production method of morpholino nucleoside (a) wherein the 3'-terminus morpholine ring nitrogen atom is protected by protecting group $P^1$ is not particularly limited, it can be produced from morpholino nucleoside (1) by a method known per se (e.g., see WO 91/09033A1) or a method analogous thereto.

For example, when $P^1$ is a trityl group, morpholino nucleoside (1) is reacted with trityl chloride in the presence of a base such as triethylamine and the like, whereby compound (a) can be obtained.

Compound (a) wherein $P^1$ is a hydrogen atom can be obtained by subjecting compound (a) wherein $P^1$ is a temporary protecting group to the below-mentioned deprotection step (1').

[Production Method of the Present Invention]

The production method of the morpholino oligonucleotide of the present invention (hereinafter to be also referred to as the "production method of the present invention") is explained. Specifically, a production method from appropriately protected n-mer morpholino oligonucleotide to appropriately protected n+p-mer morpholino oligonucleotide is explained. For example, when n=1, n-mer morpholino oligonucleotide is to be understood as "morpholino nucleoside", and when p=1, p-mer morpholino oligonucleotide is to be understood as "morpholino nucleoside" and n+p-mer morpholino oligonucleotide is to be understood as "dinucleotide".

The production method of the present invention preferably comprises the following step (1).

(1) A step of obtaining n+p-mer morpholino oligonucleotide, comprising condensing a p-mer morpholino oligonucleotide (p is any integer of one or more) wherein a 5'-hydroxy group is activated (thio)phosphated or activated (thio)phosphoramidated, and a morpholine ring nitrogen atom is protected by a temporary protecting group removable under acidic conditions (hereinafter sometimes to be simply referred to as "activated morpholino nucleotide"), with an n-mer morpholino oligonucleotide (n is an integer of one or more) wherein a 5'-hydroxy group or, when the 5'-hydroxy group has a substituent having a hydroxy group, the hydroxy group present on the substituent is protected by a protecting group having an alkyl group having not less than 10 and not more than 300 carbon atoms and/or an alkenyl group having not less than 10 and not more than 300 carbon atoms, and the morpholine ring nitrogen atom is not protected, by a (thio)phosphoramidate bond or (thio)phosphorodiamidate bond via the morpholine ring nitrogen atom.

While the upper limit of n is not particularly limited, it is preferably not more than 50, more preferably not more than 30, further preferably not more than 20.

While the upper limit of p is not particularly limited, it is preferably not more than 50, more preferably not more than 30, further preferably not more than 20, still further preferably not more than 5, particularly preferably not more than 3.

The production method of the present invention preferably further contains the following step (1'), whereby n-mer morpholino oligonucleotide wherein the 5'-hydroxy group or the hydroxy group present on the substituent of the 5'-hydroxy group used in step (1) is protected by a protecting group having an alkyl group having not less than 10 and not more than 300 carbon atoms and/or an alkenyl group having not less than 10 and not more than 300 carbon atoms, and the morpholine ring nitrogen atom is not protected is prepared.

(1') A step of removing the temporary protecting group of the morpholine ring nitrogen atom by reacting, before the condensation step (1), the n-mer morpholino oligonucleotide wherein the 5'-hydroxy group or the hydroxy group present on the substituent of the 5'-hydroxy group is protected by a protecting group having an alkyl group having not less than 10 and not more than 300 carbon atoms and/or an alkenyl group having not less than 10 and not more than 300 carbon atoms, and the morpholine ring nitrogen atom is protected by a temporary protecting group removable under acidic conditions, with an acid in a non-polar solvent.

Preferably, step (1') further includes a step of removing the temporary protecting group of the morpholine ring nitrogen atom and thereafter neutralizing same with an organic base. Consequently, steps (1') and (1) can be continuously performed in a liquid and morpholino oligonucleotide containing elongated morpholino nucleotide can be continuously obtained.

Since the 5'-hydroxy group or the hydroxy group present on the substituent of the 5'-hydroxy group of the n-mer morpholino oligonucleotide is protected by a protecting group having an alkyl group having not less than 10 and not more than 300 carbon atoms and/or an alkenyl group having not less than 10 and not more than 300 carbon atoms, the liposolubility of the obtained n+p-mer morpholino oligonucleotide is improved and, for example, by comprising the following step (2), the n+p-mer morpholino oligonucleotide can be purified conveniently and effectively by removing excess starting materials and by-products:

(2) a step of adding a polar solvent to the reaction mixture obtained in step (1') or (1) to precipitate n+p-mer oligonucleotide, and obtaining same by solid-liquid separation.

Step (2) may be performed, as shown in the following (A)-(C), with both the reaction mixtures of steps (1') and (1), or only one of the reaction mixtures of steps (1') and (1).

(A) step (1')→step (2)→step (1)→step (2)
(B) step (1')→step (1)→step (2)
(C) step (1')→step (2)→step (1)

A protecting group having an alkyl group having not less than 10 and not more than 300 carbon atoms and/or an alkenyl group having not less than 10 and not more than 300 carbon atoms is preferably the formula (II) Z—Y—L— (wherein each symbol is as described above), in which case the above-mentioned step (2) can be more efficiently performed.

When the amount of the by-product generated can be controlled by the management of equivalent of the starting materials and controlling the reaction, it is preferable to repeat steps (1') and (1) as a basic unit, which includes step (2).

Since the generation of by-product can be strictly managed and controlled and highly pure morpholino oligonucleotide can be obtained, it is preferable to repeat any of the above-mentioned (A)-(C) containing step (1') to step (2) as a basic unit.

Morpholino oligonucleotide can be isolated and produced by further including step (3) in the production method of the present invention:

(3) A step of removing all the protecting groups of the obtained n+p-mer morpholino oligonucleotide.

Each step is explained in detail in the following.

1. Explanation of "n-Mer Morpholino Oligonucleotide"

First, n-mer morpholino oligonucleotide used as a starting material of steps (1') and (1) is explained.

The n-mer morpholino oligonucleotide used in step (1') is, for example, n-mer morpholino oligonucleotide wherein the 5'-hydroxy group or the hydroxy group present on the substituent of the 5'-hydroxy group is protected by a protecting group having an alkyl group having not less than 10 and not more than 300 carbon atoms and/or an alkenyl group having not less than 10 and not more than 300 carbon atoms, and the morpholine ring nitrogen atom is protected by a temporary protecting group removable under acidic conditions, as shown by, for example, the following formula (i), and the n-mer morpholino oligonucleotide used in step (1) is, for example, n-mer morpholino oligonucleotide wherein the 5'-hydroxy group or the hydroxy group present on the substituent of the 5'-hydroxy group is protected by a protecting group having an alkyl group having not less than 10 and not more than 300 carbon atoms and/or an alkenyl group having not less than 10 and not more than 300 carbon atoms, and the morpholine ring nitrogen atom is not protected, as shown by, for example, the following formula (ii).

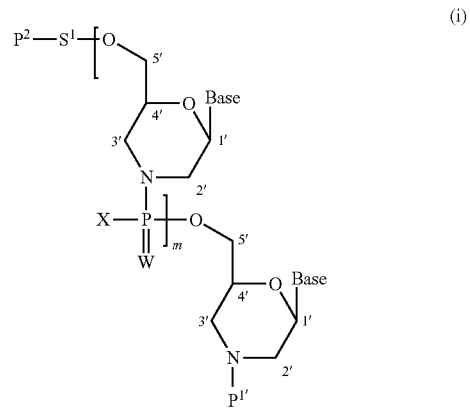

-continued (ii)

[Chemical structure showing morpholino oligonucleotide with P²—S¹—O at 5' position, Base, N, X—P(=W)—O at 5', m subscript, Base, N—H at 2']

(wherein m is any integer of not less than 0 which corresponds to n−1,
$P^{1'}$ is a temporary protecting group removable under acidic conditions,
$P^2$ is a protecting group having an alkyl group having not less than 10 and not more than 300 carbon atoms and/or an alkenyl group having not less than 10 and not more than 300 carbon atoms, and
other symbols are the same as respective definitions in the formula (I).)

Each symbol in the formulas (i) and (ii) is explained below.

While the upper limit of m is not particularly limited, it is generally not more than 99, preferably not more than 74, more preferably not more than 49, further preferably not more than 29.

The temporary protecting group removable under acidic conditions for $P^{1'}$ in the formula (i) is not particularly limited as long as it can be deprotected under acidic conditions and can be used as a hydroxy-protecting group. Examples thereof include a trityl group, a 9-(9-phenyl)xanthenyl group, a 9-phenylthioxanthenyl group, di($C_{1-5}$ alkoxy)trityl groups such as a 1,1-bis(4-methoxyphenyl)-1-phenylmethyl group, a dimethoxytrityl group and the like, mono($C_{1-18}$ alkoxy)trityl groups such as 1-(4-methoxyphenyl)-1,1-diphenylmethyl group, monomethoxytrityl group and the like, and the like can be mentioned. Among these, a trityl group, a monomethoxytrityl group and a dimethoxytrityl group are preferable, and a trityl group and a dimethoxytrityl group is more preferable, in view of easiness of deprotection and easy availability.

The "protecting group having an alkyl group having not less than 10 and not more than 300 carbon atoms and/or an alkenyl group having not less than 10 and not more than 300 carbon atoms" for $P^2$ in the formulas (i) and (ii) is not particularly limited as long as it is a group stable under acidic conditions under which the protecting group of the 3'-terminus morpholine ring nitrogen atom can be removed and can dissolve n-mer morpholino oligonucleotide in a non-polar solvent as a reaction solvent to allow for the progress of the reactions in steps (1') and (1). A group represented by the following formula (II) is preferable.

Z—Y—L-                                                     (II)

[wherein each symbol is as defined above].

When a protecting group having an alkyl group having not less than 10 and not more than 300 carbon atoms and/or an alkenyl group having not less than 10 and not more than 300 carbon atoms, more preferably, a group represented by the formula (II), is used as a hydroxy-protecting group of the 5'-hydroxy group or the hydroxyl group present on the substituent of the 5'-hydroxy group, the liposolubility and solubility of n-mer morpholino oligonucleotide and n+p-mer morpholino oligonucleotide in a solvent (particularly, non-polar solvent) can be improved, steps (1') and (1) can be performed smoothly and, as in the below-mentioned step (2), n-mer morpholino oligonucleotide or n+p-mer morpholino oligonucleotide can be isolated and purified conveniently.

Preferable embodiments of L, Y and Z in the formula (II) are the same as those of L, Y and Z in a group represented by the formula (I).

2. Explanation of "p-Mer Morpholino Oligonucleotide"

First, p-mer morpholino oligonucleotide used as a starting material of step (1) is explained.

The "p-mer morpholino oligonucleotide (p is any integer of one or more) wherein a 5'-hydroxy group is activated (thio)phosphated or activated (thio)phosphoramidated, and a morpholine ring nitrogen atom is protected by a temporary protecting group removable under acidic conditions" used in step (1) is not particularly limited as long as the structural requirements are met.

The "5'-hydroxy group is activated (thio)phosphated or activated (thio)phosphoramidated" means that 5'-hydroxy group of the morpholino oligonucleotide is, for example, modified by a group represented by the following formula (c):

(c)

X—P(=W)(L¹)—*

(wherein
* indicates the bonding position to the 5'-terminus hydroxyl group of morpholino oligonucleotide,
$L^1$ is a leaving group,
X is a $C_{1-6}$ alkoxy group, a di-$C_{1-6}$ alkylamino group, or a piperazino group wherein the 4-position nitrogen atom is protected by a protecting group, and optionally further substituted, and
W is an oxygen atom or a sulfur atom).

The "activated phosphated" means the above-mentioned formula wherein X is a $C_{1-6}$ alkoxy group, and W is an oxygen atom.

The "activated thiophosphated" means the above-mentioned formula wherein X is a $C_{1-6}$ alkoxy group, and W is a sulfur atom.

The "activated phosphoramidated" means the above-mentioned formula wherein X is a di-$C_{1-6}$ alkylamino group or a piperazino group wherein the 4-position nitrogen atom is protected by a protecting group, and optionally further substituted, and W is an oxygen atom.

The "activated (thio)phosphoramidated" means the above-mentioned formula wherein X is a di-$C_{1-6}$ alkylamino group or a piperazino group wherein the 4-position nitrogen atom is protected by a protecting group, and optionally further substituted, and W is a sulfur atom.

Examples of the leaving group for $L^1$ include a halogen atom, a methanesulfonyloxy group, a p-toluenesulfonyloxy group and the like, and a chlorine atom is preferable.

The definitions, examples and preferable embodiments of X and W are as explained for the above-mentioned formula (I).

The definitions, examples and preferable embodiments of the "temporary protecting group removable under acidic conditions" are as explained for the above-mentioned formula (I).

As a preferable p-mer morpholino oligonucleotide used in step (1), a compound represented by the formula (iii) can be mentioned.

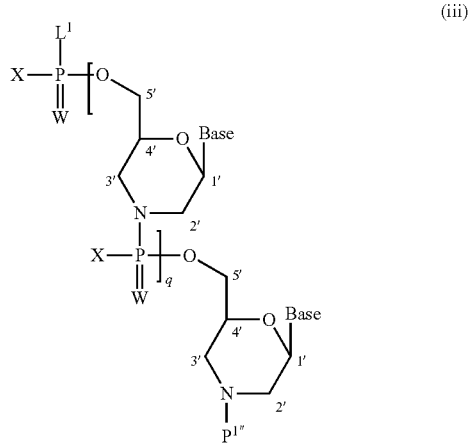

(iii)

(wherein
q is any integer of not less than 0 which corresponds to p-1, $P^{1'''}$ is a temporary protecting group removable under acidic conditions, and other symbols are the same as respective definitions in the formula (I) and the formula (c)).

q in the formula (iii) is preferably 0. While the upper limit of q is not particularly limited, it is generally not more than 99, preferably not more than 74, more preferably not more than 49, further preferably not more than 29.

The temporary protecting group removable under acidic conditions for $P^{1'''}$ in the formula (iii) is not particularly limited as long as it can be deprotected under acidic conditions and can be used as a hydroxy-protecting group. Examples thereof include a trityl group, a 9-(9-phenyl)xanthenyl group, a 9-phenylthioxanthenyl group, di($C_{1-6}$ alkoxy)trityl groups such as a 1,1-bis(4-methoxyphenyl)-1-phenylmethyl group, dimethoxytrityl and the like, mono($C_{1-18}$ alkoxy)trityl groups such as 1-(4-methoxyphenyl)-1,1-diphenylmethyl group, monomethoxytrityl group and the like, and the like can be mentioned. Among these, a trityl group, a monomethoxytrityl group and a dimethoxytrityl group are preferable, and a trityl group and a dimethoxytrityl group are more preferable, in view of easiness of deprotection and easy availability.

Preferable embodiments of other symbols in the formula (iii) are as explained for the above-mentioned formulas (I) and (c).

The p-mer morpholino oligonucleotide of the present invention can be prepared by a method known per se (e.g., the method described in WO 91/09033A1), or a method analogous thereto. For example, a compound wherein $L^1$ is a chlorine atom can be produced by reacting a compound of the following formula (iii') which is a compound represented by the formula (iii), wherein the 5'-hydroxy group is not activated, with, for example, dichloro(thio)phosphate or dichloro(thio)phosphoramidate represented by the formula (d): $Cl_2P(=W)(X)$ (wherein W and X are as defined above).

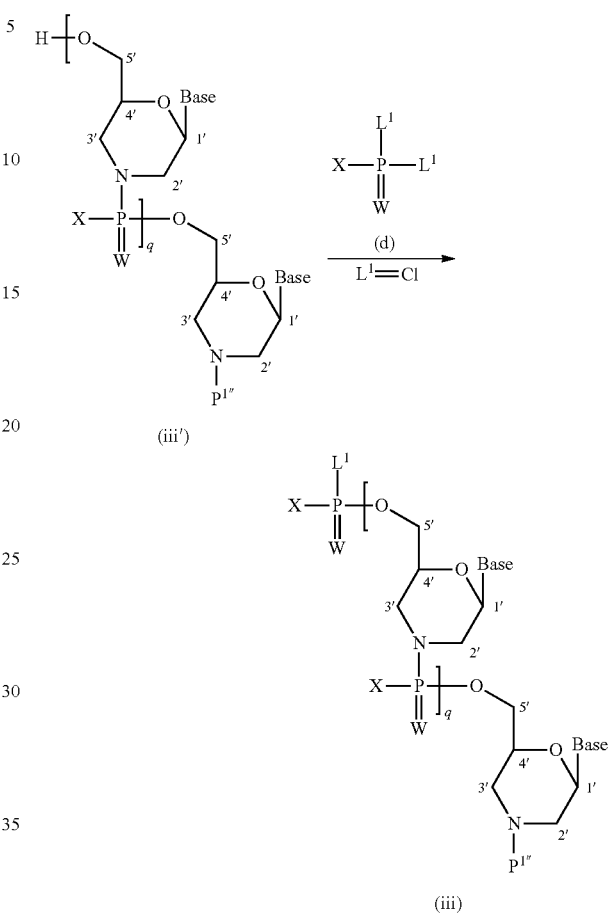

(iii')

(iii)

As dichloro(thio)phosphate or dichloro(thio)phosphoramidate represented by the formula (d), a commercially available product can be used, or can be produced by a known method (e.g., the methods described in WO 91/09033, WO 2008/008113 etc.) or a method analogous thereto.

A compound of the formula (iii') can be prepared by a known method, for example, WO91/09033 and the like.

3. Explanation of Steps (1')-(3)

While steps (1')-(3) are explained below by reference to the formulas (i), (ii), (iii) and the like for convenience, they are not limited thereby.

Step (1') (Deprotection Step)

This step is a step of removing the temporary protecting group of the morpholine ring nitrogen atom by reacting, before the condensation step (1), n-mer morpholino oligonucleotide (i) wherein the 5'-hydroxy group or the hydroxy group present on the substituent of the 5'-hydroxy group is protected by a protecting group having an alkyl group having not less than 10 and not more than 300 carbon atoms and/or an alkenyl group having not less than 10 and not more than 300 carbon atoms, and the morpholine ring nitrogen atom is protected by a temporary protecting group removable under acidic conditions, with an acid in a non-polar solvent to give n-mer morpholino oligonucleotide (ii) wherein the 5'-hydroxy group or the hydroxy group present on the substituent of the 5'-hydroxy group is protected by a protecting group having an alkyl group having not less than 10 and not more than 300 carbon atoms and/or an alkenyl group having not less than 10 and not more than 300 carbon atoms, and morpholine ring nitrogen atom is not protected.

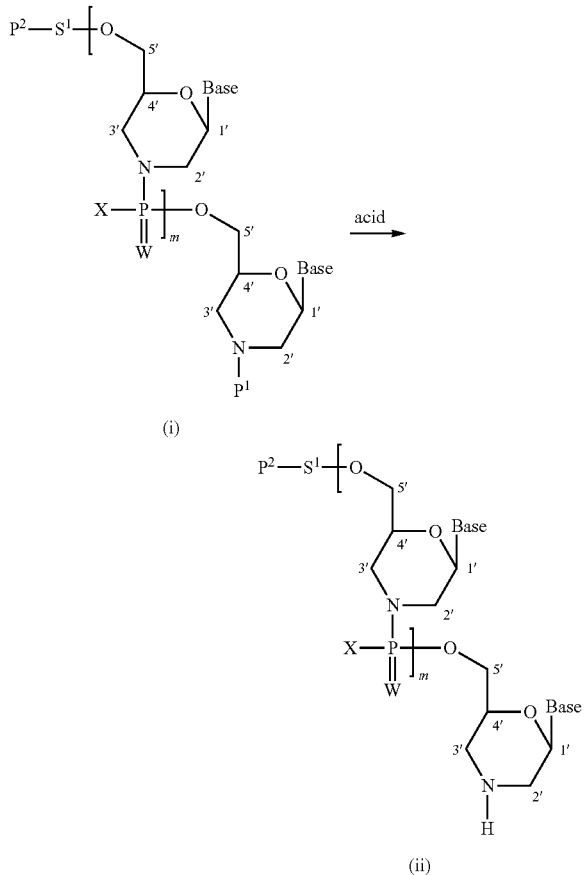

(wherein each symbol is as defined above).

This step is performed in a solvent that does not influence the reaction. Since a higher solubility of the solvent is expected to afford superior reactivity, a non-polar solvent showing high solubility of n-mer morpholino oligonucleotide (i) of the present invention is preferably selected. Specifically, examples thereof include halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like. Among them, dichloromethane, chloroform, 1,2-dichloroethane, benzene, toluene, xylene, mesitylene, hexane, pentane, heptane, nonane, cyclohexane, ethyl acetate, isopropyl acetate, tert-butyl methyl ether, cyclopentyl methyl ether, and the like are preferable. Two or more kinds of these solvents may be used in a mixture in an appropriate ratio.

In this step, the concentration of n-mer morpholino oligonucleotide (i) in a solvent is not particularly limited as long as the oligonucleotide is dissolved, it is preferably 1 to 30 mass.

While the acid to be used in this step is not particularly limited as long as good deprotection can be achieved, trifluoroacetic acid, cyanopyridine trifluoroacetate and trifluoroethanol, trimethylamine trifluoroacetate, cyanoacetic acid, acetic acid, dichloroacetic acid, phosphoric acid, mesylic acid, tosic acid, hydrochloric acid and the like are preferably used.

Since good reaction can be achieved, trifluoroacetic acid, cyanopyridine trifluoroacetate, trimethylamine trifluoroacetate, and cyanoacetic acid are more preferable, cyanopyridine trifluoroacetate and trimethylamine trifluoroacetate are further preferable, and trimethylamine trifluoroacetate is particularly preferable. These acids may be diluted with the above-mentioned non-polar solvent. When the aforementioned acid is used, it may be combined with a particular base (e.g., triethylamine etc.) to appropriately adjust the acidity before use.

The amount of the acid to be used in this step is 1 to 100 mol, preferably 1 to 40 mol, per 1 mol of n-mer morpholino oligonucleotide (i).

In this step, a cation scavenger may be added to prevent side reactions due to cationized compound and the like of protecting group $P^1$ such as trityl cation and the like resulting from deprotection. Examples of preferable cation scavengers include pyrrole, indole, ethanol, 2,2,2-trifluoroethanol, methanol, anisole, p-cresol, triisopropylsilane, mercaptoethanol, thioanisole and the like. Among these, pyrrole, indole, ethanol, and 2,2,2-trifluoroethanol are more preferable, and ethanol and 2,2,2-trifluoroethanol are particularly preferable.

The amount of the cation scavenger to be used can be appropriately determined in consideration of an excess amount of p-mer morpholino oligonucleotide (iii) relative to n-mer morpholino oligonucleotide (ii) (number of moles of p-mer morpholino oligonucleotide (iii)-number of moles of n-mer morpholino oligonucleotide (ii)), and is preferably 1-20 equivalents, more preferably 1-10 equivalents, relative to the excess amount (moles).

While the reaction temperature in this step is not particularly limited as long as the reaction proceeds, it is preferably −10° C. to 50° C., more preferably 0° C. to 40° C. While the reaction time varies depending on the kind of n-mer morpholino oligonucleotide to be used, the kind of acid, the kind of solvent, the reaction temperature and the like, it is 5 min to 5 hr.

When an acid used as a deprotecting agent is present in the condensation step of the next step, deprotection of protecting group $P^{1''}$ of p-mer morpholino oligonucleotide (iii) is induced. Therefore, a removal treatment or a neutralization treatment is necessary. To continuously perform the deprotection step and subsequent condensation step in a solution, it is preferable to remove the temporary protecting group of the 3'-terminus morpholine ring nitrogen atom and neutralize the compound with an organic base in this step.

The organic base to be used for neutralization is not particularly limited as long as it can neutralize the above-mentioned acids, and the obtained salt can function as a condensing agent. Since the reaction proceeds smoothly, N,N-diisopropylethylamine, pyridine, 4-cyanopyridine, triethylamine is preferable, N,N-diisopropylethylamine and triethylamine are more preferable, and N,N-diisopropylethylamine is particularly preferable.

The amount of the organic base to be used in this step is 1 to 10 mol, preferably 1 to 3 mol, per 1 mol of the acid.

A particularly preferable combination of an acid and an organic base in this step is that of cyanopyridine trifluoroacetate and N,N-diisopropylethylamine or cyanoacetic acid and N,N-diisopropylethylamine.

Step (1) (Condensation Step)

In this step, a p-mer morpholino oligonucleotide (iii) wherein a 5'-hydroxy group is activated (thio)phosphated or activated (thio)phosphoramidated, and a morpholine ring nitrogen atom is protected by a temporary protecting group removable under acidic conditions is condensed with an n-mer morpholino oligonucleotide (ii) wherein a 5'-hydroxy group or a hydroxy group present on a substituent of the 5'-hydroxy group is protected by a protecting group having an alkyl group having not less than 10 and not more than 300 carbon atoms and/or an alkenyl group having not less than 10 and not more than 300 carbon atoms, and the morpholine ring nitrogen atom is not protected, by a (thio)phosphoramidate bond or (thio)phosphorodiamidate bond via the morpholine ring nitrogen atom to give n+p-mer morpholino oligonucleotide (iv).

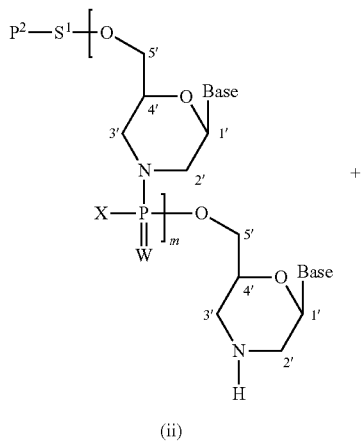

(ii)

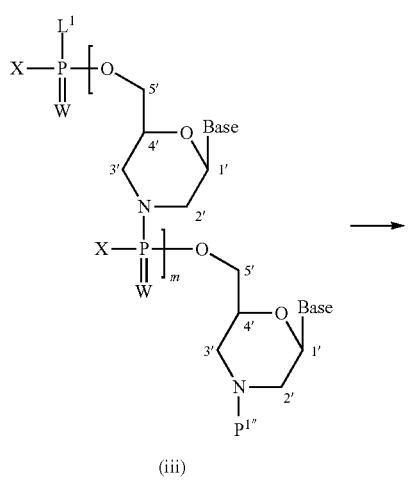

(iii)

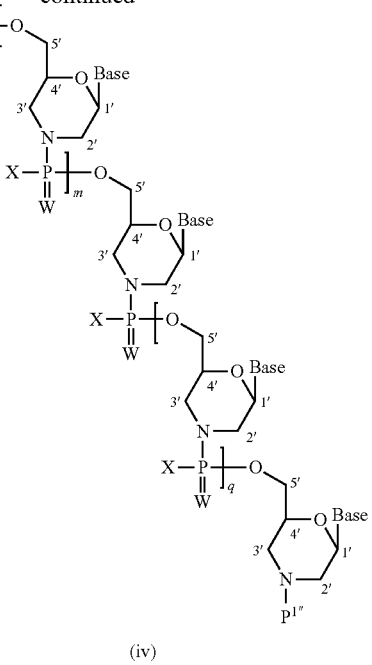

(iv)

(wherein each symbol is as defined above).

As the p-mer morpholino oligonucleotide (iii) wherein a 5'-hydroxy group is activated (thio)phosphated or activated (thio)phosphoramidated, and a morpholine ring nitrogen atom is protected by a temporary protecting group removable under acidic conditions, a morpholino nucleoside wherein p is 1 (i.e., morpholino nucleoside wherein 5'-hydroxy group is activated (thio)phosphated or activated (thio)phosphoramidated, and morpholine ring nitrogen atom is protected by temporary protecting group $P^{1''}$) is preferable.

In this step, the n-mer morpholino oligonucleotide (ii) to be used is not particularly limited, and one obtained in the aforementioned step (1') can be preferably used. In this case, a p-mer morpholino oligonucleotide (iii) only needs to be added directly to the reaction mixture after step (1'), without isolating the n-mer morpholino oligonucleotide (ii).

Alternatively, after step (1'), the reaction mixture may be subjected to the below-mentioned step (2), n-mer morpholino oligonucleotide (ii) is once isolated and dissolved in a given solvent, and thereafter, p-mer morpholino oligonucleotide (iii) may be added.

This step is performed in a solvent that does not influence the reaction. A non-polar solvent showing high solubility of n-mer morpholino oligonucleotide (ii) of the present invention is, preferably selected. Specifically, examples thereof include halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like. Among them, dichloromethane, chloroform, 1,2-dichloroethane, benzene, toluene, xylene, mesitylene, hexane, pentane, heptane, nonane, cyclohexane, ethyl acetate, isopropyl acetate, tert-butyl methyl ether, cyclopentyl methyl ether, and the like are preferable. Two or more kinds of these solvents may be used in a mixture in an appropriate ratio. In addition, a polar solvent may be mixed at an appropriately ratio as long as n-mer morpholino oligonucleotide (ii) is dissolved. Specifically, polar solvents such as nitrile solvents such as acetonitrile, propionitrile and the like; ketone solvents such as acetone, 2-butanone and the like; polar ether solvents such as 1,4-dioxane, tetrahydrofuran and the like; amide solvents such as N,N-dimethylformamide, N,N-dimethylacetamide, N-methylpyrrolidone, 1,3-dimethyl-2-imidazolinone and the like, sulfoxide solvents such as dimethyl sulfoxide and the like can be mentioned.

The amount of p-mer morpholino oligonucleotide (iii) to be used is 1-10 mol, preferably 1-5 mol, more preferably 1-2 mol, per 1 mol of n-mer morpholino oligonucleotide (ii).

While the reaction temperature is not particularly limited as long as the reaction proceeds, 0° C. to 100° C. is preferable, and 20° C. to 50° C. is more preferable. While the reaction time varies depending on the kind of n-mer morpholino oligonucleotide (ii) and p-mer morpholino oligonucleotide (iii) to be condensed, the reaction temperature and the like, it is 5 min to 24 hr.

After the completion of the condensation reaction, the reaction mixture is preferably treated with a quenching agent. Using a quenching agent, p-mer morpholino oligonucleotide (iii) remaining in the condensation reaction can be completely quenched, and induction of double addition in the condensation reaction of the next cycle by the residual activated morpholino nucleotide can be avoided, which in turn prevents degradation of the quality of the object morpholino oligonucleotide.

The double addition refers to a doubly addition of the same residue of activated morpholino nucleotide used and remained in the condensation reaction of the previous cycle, which reacts in the condensation reaction of the subsequent cycle.

As the quenching agent, any nucleophilic reagent can be used as long as it reacts with p-mer morpholino oligonucleotide (iii). Preferable examples thereof include organic amine and thiol. Of them, secondary amine is preferable, and morpholine is particularly preferable.

The amount of the quenching agent to be used can be appropriately determined in consideration of an excess amount of p-mer morpholino oligonucleotide (iii) relative to n-mer morpholino oligonucleotide (ii) (number of moles of p-mer morpholino oligonucleotide (iii)-number of moles of n-mer morpholino oligonucleotide (ii)), and is preferably 0.1-10 equivalents, more preferably 0.3-3 equivalents, relative to the excess amount (moles).

After adding a quenching agent to the reaction mixture, p-mer morpholino oligonucleotide (iii) can be completely quenched by reacting the mixture at 0° C.-100° C., preferably 20° C.-50° C., for 30 min-24 hr, preferably 30 min-5 hr.

Step (2) (Separation and Purification Step of Morpholino Oligonucleotide)

In n-mer morpholino oligonucleotide (ii) or n+p-mer morpholino oligonucleotide (iv) obtained in the above-mentioned step (1') and/or step (1), the hydroxy group at the 5'-terminus is protected by a protecting group having an alkyl group containing not less than 10 and not more than 300 carbon atoms and/or an alkenyl group having not less than 10 and not more than 300 carbon atoms, preferably, a protecting group represented by the formula (II): Z—Y-L- (wherein each symbol is as defined above). Therefore, very high liposolubility is imparted to the morpholino oligonucleotide, and the morpholino oligonucleotide can be conveniently isolated and purified by crystallization and extraction operation alone, without requiring a complicated operation such as column purification and the like.

In the following, an isolation and purification method of morpholino oligonucleotide by crystallization is explained, to which the present invention is not limited.

The isolation and purification step of morpholino oligonucleotide by crystallization is a step of adding a polar solvent to the reaction mixture obtained in step (1') or (1) to precipitate oligonucleotide, and obtaining same by solid-liquid separation.

A polar solvent may be directly added to the reaction mixture obtained in step (1') and/or step (1), or the reaction mixture obtained in step (1') and/or step (1) may be concentrated and a polar solvent may be added.

Examples of the polar solvent used to precipitate the object product, morpholino oligonucleotide, in this step include alcohol solvents such as methanol, ethanol, isopropanol and the like; nitrile solvents such as acetonitrile, propionitrile and the like; ketone solvents such as acetone, 2-butanone and the like; amide solvents such as dimethylformamide, dimethylacetamide, N-methylpiperidone and the like, sulfoxide solvents such as dimethyl sulfoxide and the like; water etc., and mixed solvent of two or more kinds thereof. A polar solvent aiming at increasing the precipitation efficiency can be used in the form of a mixed solvent of an organic solvent and water. In this case, the content of water in the polar solvent can be appropriately set to a preferable value depending on the organic solvent to be used. It is generally 1-50%(V/V), preferably 10-30%(V/V). As the polar solvent, alcohol solvent, nitrile solvent, and a mixed solvent of each of these solvents and water are preferable, methanol, acetonitrile, and a mixed solvent of each of these and water are more preferable, and acetonitrile and a mixed solvent of acetonitrile and water are particularly preferable.

The production method of morpholino oligonucleotide of the present invention can afford the object morpholino oligonucleotide with high purity and in a high yield by repeating the above-mentioned steps desired times in the order of (1')-(2)-(1)-(2), (1')-(2)-(1), or (1')-(1)-(2).

Step (3) (Deprotection, Morpholino Oligonucleotide Isolation Step)

In the production method of morpholino oligonucleotide of the present invention, deprotection is performed after step (2) according to the kind and properties of the protecting group, whereby morpholino oligonucleotide is isolated. All protecting groups of the morpholino oligonucleotide can be removed according to the deprotection method described in Greene's PROTECTIVE GROUPS IN ORGANIC SYNTHESIS, 4th ed., Wiley-Interscience (2006) and the like. To be specific, a protecting group having an alkyl group having not less than 10 and not more than 300 carbon atoms and/or an alkenyl group having not less than 10 and not more than 300 carbon atoms in the present invention, as well as phenoxyacetyl group, acetyl group and the like which are protecting groups of nucleic acid bases can all be removed by a treatment with aqueous ammonia, aqueous ammonia/ethanol solution, or a mixture of aqueous ammonia and aqueous methylamine solution. In addition, the 3'-terminus morpholine ring nitrogen atom-protecting group of the morpholino oligonucleotide can be removed by a treatment with the acid used in step (1') or an appropriately diluted solution of such acid.

The progress of the reaction in each of the above-mentioned steps can be confirmed by a method similar to conventional liquid phase organic synthesis reaction. That is, the reaction can be traced by thin layer silica gel chromatography, high performance liquid chromatography and the like.

The morpholino oligonucleotide obtained by step (2) or step (3) can also be led to a desired morpholino oligonucleotide derivative by further applying an organic synthesis reaction.

The morpholino oligonucleotide produced by the present invention can be used for various applications such as various veterinary pharmaceutical products (RNA, DNA, oligonucleic acid medicine, peptide modified morpholino oligonucleotide etc.) for human or animal, functional food, food for specified health uses, food, chemical product, polymer material for living body or industrial use, and the like.

EXAMPLES

The present invention is explained in more detail in the following by referring to Preparation Examples and Examples, which are not to be construed as limiting the scope of the present invention. The reagents, apparatuses and materials used in the present invention are commercially available unless otherwise specified. In the present specification, when indicated by abbreviation, unless particularly indicated, each indication is based on the abbreviation of the IUPAC-IUB Commission on Biochemical Nomenclature or conventional abbreviations in the art.

The abbreviations used in Reference Examples and Examples are as follows.
mo: morpholino nucleoside
moA: morpholinoadenosine
moG: morpholinoguanosine
moC: morpholinocytidine
moT: morpholinothymidine
moU: morpholinouridine
PMO: phosphorodiamidate morpholino oligonucleotide For example, indication of PMO[A-G-C] means that the left side is the 5'-terminus, the right side is the 3'-terminus, and it is a phosphorodiamidate morpholino oligonucleotide in the order of morpholinoadenosine, morpholinoguanosine, and morpholinocytidine from the 5'-terminus.
bz: benzoyl group
pac: phenoxyacetyl group
ce: 2-cyanoethyl group When a nucleic acid base of morpholino nucleoside is protected, the protecting group is indicated as superscript to the right of the abbreviation (A, G, C, T and U) of the nucleic acid base.

For example, $C^{bz}$ means that the amino group of cytosine is protected by a benzyl group, and $G^{ce/pac}$ means that the amino group of guanine is protected by a phenoxyacetyl group, and the carbonyl group is protected by a 2-cyanoethyl group.
TOB: 3,4,5-tri(octadecyloxy)benzyloxy group
suc: succinyl group
Tr, Trt: trityl group
CYTFA: cyanopyridine.trifluoroacetate
DIEA: N,N-diisopropylethylamine
TFE: 2,2,2-trifluoroethanol
TFA: trifluoroacetic acid
DMAP: 4-dimethylaminopyridine
MeCN: acetonitrile
HOBt: 1-hydroxybenzotriazole
UHPLC: ultra high performance liquid chromatography
EDC.HCl: N-ethyl-N'-(3-dimethylaminopropyl)carbodiimide hydrochloride
MMTr: monomethoxytrityl
teg: triethylene glycol

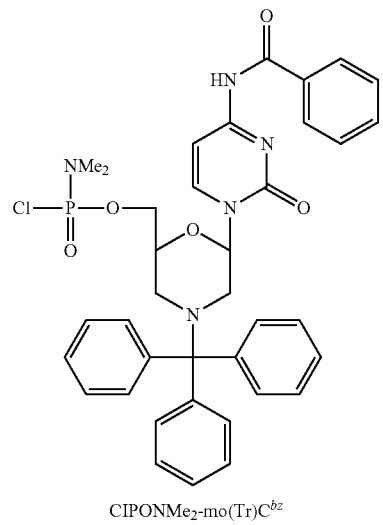

ClPONMe$_2$-mo(Tr)C$^{bz}$

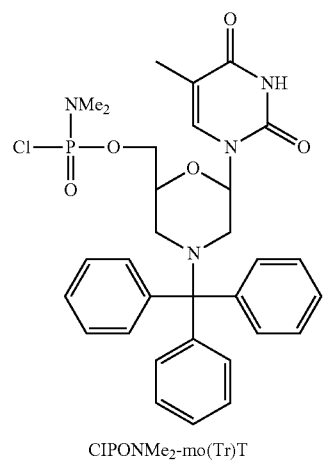

ClPONMe$_2$-mo(Tr)T

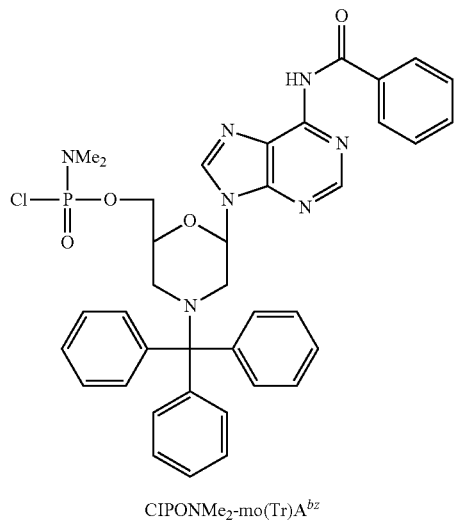

ClPONMe$_2$-mo(Tr)A$^{bz}$

-continued

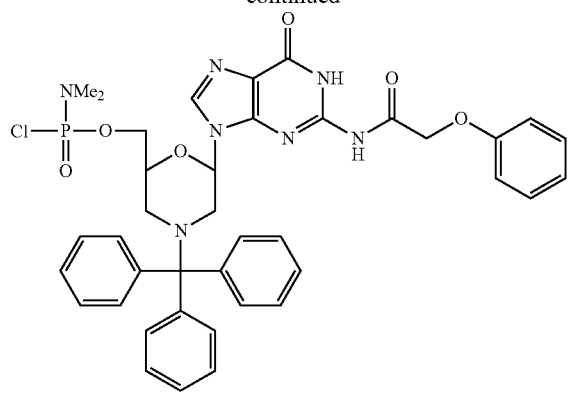

ClPONMe₂-mo(Tr)G^{pac}

-continued

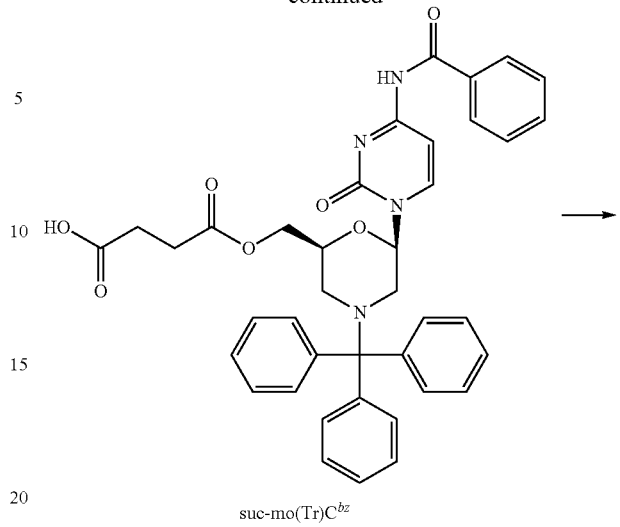

suc-mo(Tr)C^{bz}

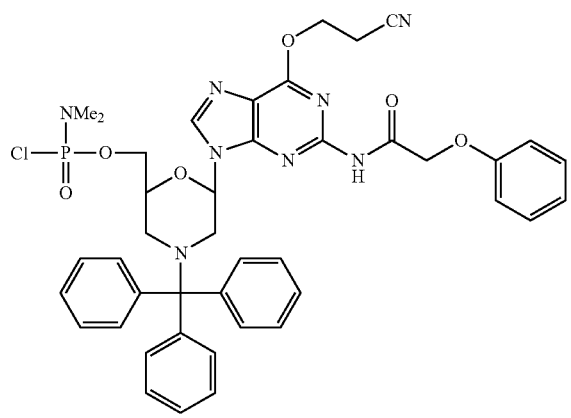

ClPONMe₂-mo(Tr)G^{ce/pac}

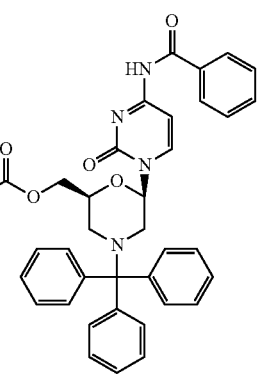

TOB-suc-mo(Tr)C^{bz}

Reference Example 1

Synthesis of TOB-suc-moC^{bz}-Tr (Introduction of Suc-moC^{bz}-Tr Intermediate into TOB Anchor)

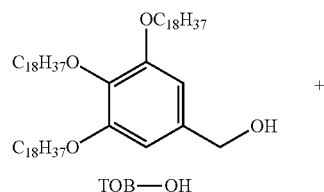

TOB—OH

+

3,4,5-tri(Octadecyloxy)benzyl alcohol (4500 mg, 4.92 mmol) was dissolved in chloroform (45 ml), and suc-moC^{bz}-Tr (3640 mg, 5.41 mmol), EDC.HCl (1141 mg, 5.95 mmol), and DMAP (33 mg, 0.055 mmol) were each added to the solution in 3 portions every 1 hr in an ice bath. The mixture was stirred at room temperature overnight, suc-moC^{bz}-Tr (503 mg, 0.74 mmol) and EDC.HCl (157 mg, 0.82 mmol) were additionally added therein and the completion of the reaction was confirmed by HPLC. The solvent was evaporated under reduced pressure, MeCN (10 ml) was added and the mixture was evaporated again under reduced pressure. To the residue was added MeCN (50 ml), and the precipitate was collected by filtration, completely dissolved in chloroform (30 ml), recrystallized from MeCN (90 ml) and dried under reduced pressure to give TOB-suc-moC^{bz}-Tr (7337 mg, yield 95%).

TOF-MS+ (m/z) 1566.8

Reference Example 2

Detritylation Reaction of TOB-suc-moC$^{bz}$-Tr

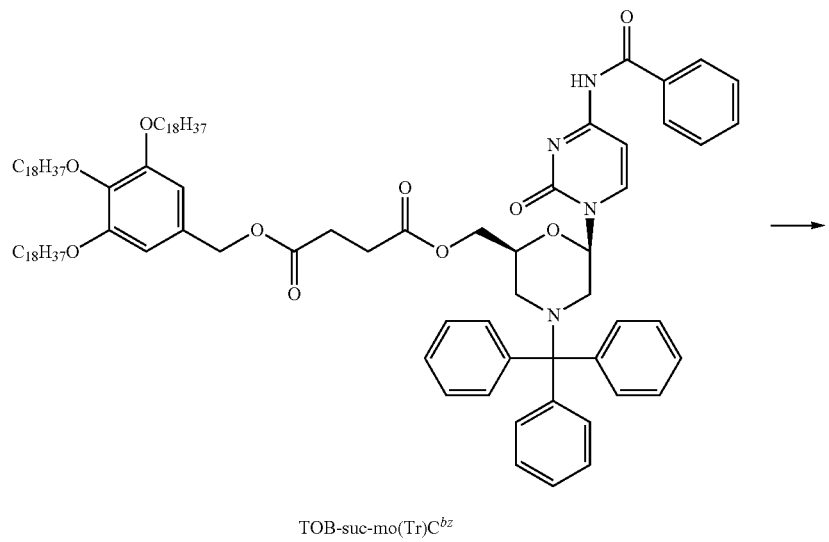

TOB-suc-mo(Tr)C$^{bz}$

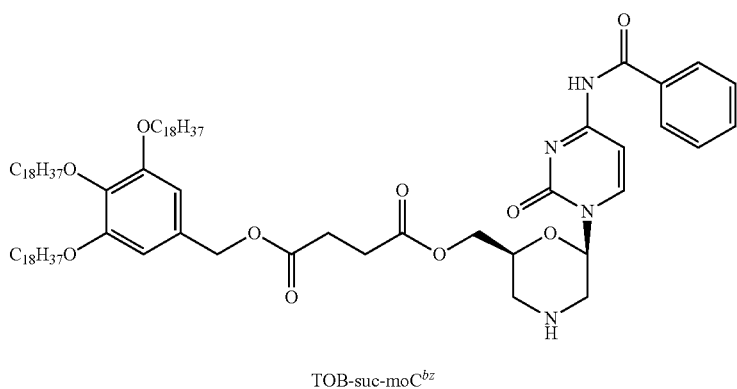

TOB-suc-moC$^{bz}$

TOB-suc-moC$^{bz}$-Tr (500 mg, 0.32 mmol) was dissolved in chloroform (5 mL), SOLUTION A* (16 ml) was slowly added dropwise over 30 min in an ice bath, and the mixture was stirred at room temperature for 1.5 hr. After completion of the reaction, a diluted solution of DIEA (137 μl)/chloroform (1 mL) was slowly added in an ice bath, MeCN (50 ml) was added, and the precipitate was collected by filtration. The obtained crystals were washed again with MeCN (10 ml), and dried under reduced pressure to give TOB-suc-moC$^{bz}$ (395 mg, yield 94%).

* composition of SOLUTION A is as described below.

EtOH/TFE/TFA/TEA/chloroform=250 μl/2.5 mL/173 μl/161 μl/22.25 ml

TOF-MS+ (m/z) 1324.9

The scheme of Examples 1 and 2 is shown below.

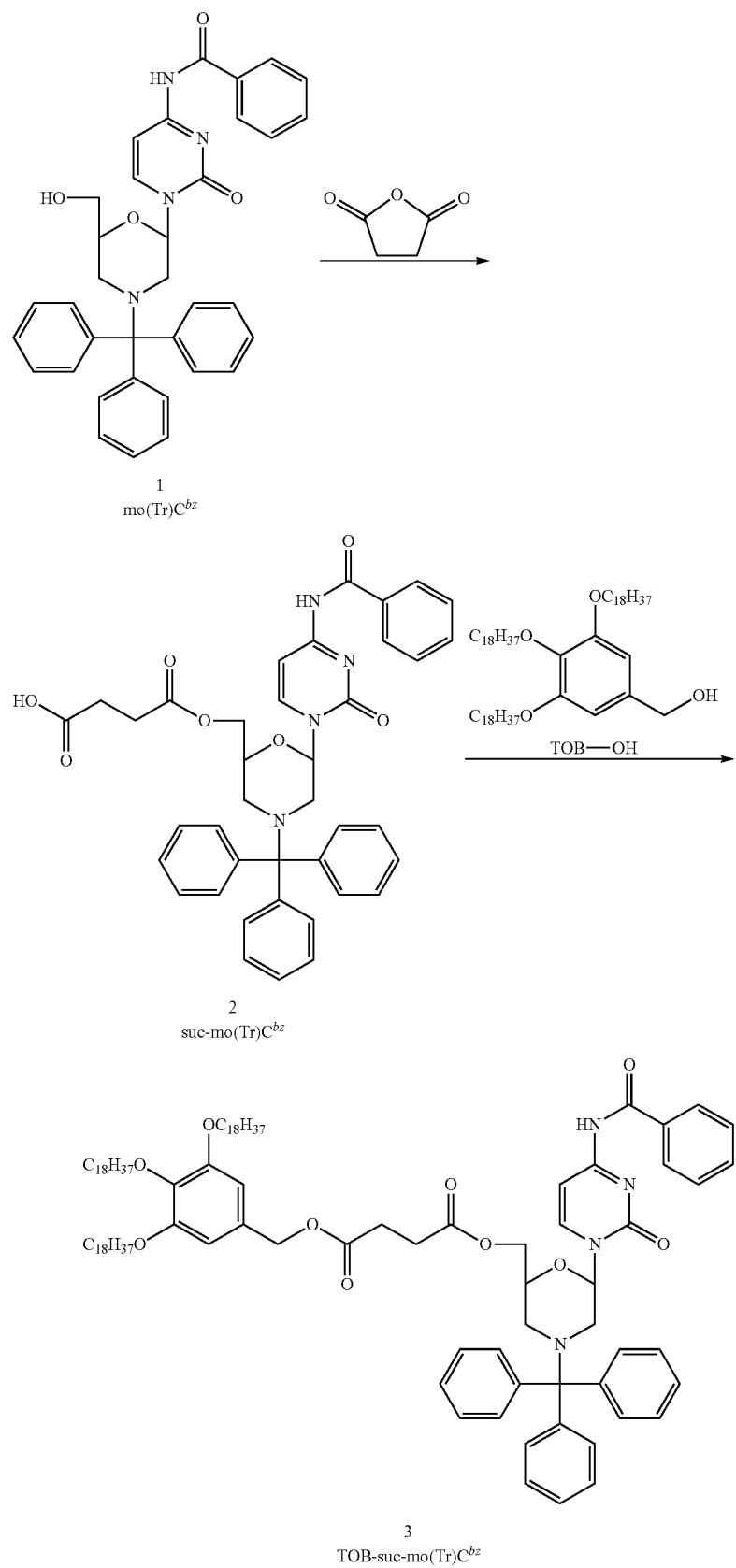

Example 1

Synthesis of Compound 2: Bonding of Succinyl Linker to Compound 1 [mo(Tr)C$^{bz}$]

Under an argon atmosphere, compound 1 [mo(Tr)C$^{bz}$] (573 mg, 1.0 mmol) and N,N-dimethylaminopyridine (183 mg, 1.5 mmol) were dissolved in dry dichloromethane (7.0 mL), succinic anhydride (150 mg, 1.5 mmol) was added, and the mixture was stirred at room temperature for 3 hr. After confirmation of the completion of the reaction by thin layer chromatography, methanol (1.0 mL) was added, and the reaction mixture was concentrated under reduced pressure. To the obtained concentrated residue were added ethyl acetate (8.0 mL) and 0.5 mol/l KH$_2$PO$_4$ aqueous solution (8.0 mL) and the mixture was partitioned by extraction. Furthermore, the aqueous layer was extracted with ethyl acetate (8.0 mL). The obtained ethyl acetate layers were combined, washed with 0.5 mol/l KH$_2$PO$_4$ aqueous solution (13.0 mL), water (13.0 mL) and saturated brine (13.0 mL), dried over magnesium sulfate, and filtered. The filtrate was concentrated to dryness to give compound 2 [suc-mo(Tr)C$^{bz}$] (680 mg, quant).

$^1$H-NMR (400 MHz, CDCl$_3$): δ 1.20 (1H, t, J=10.4 Hz), 1.49 (1H, t, J=11.2 Hz), 2.52-2.75 (4H, m), 3.14 (1H, d, J=11.5 Hz), 3.80 (1H, d, J=10.4 Hz), 3.92 (1H, d, J=11.7 Hz), 4.37-4.59 (2H, m), 6.19 (1H, d, J=7.2 Hz), 7.15-7.88 (22H, m)

Example 2

Synthesis of Compound 3: Supporting Compound 2 [suc-mo(Tr)C$^{bz}$] on TOB Anchor [3,4,5-tris(octadecyloxy)benzyl Alcohol]

Under an argon atmosphere, 3,4,5-tris(octadecyloxy)benzyl alcohol (133 mg, 0.15 mmol), N,N-dimethylaminopyridine (21 mg, 0.18 mmol), compound 2 [suc-mo(Tr)C$^{bz}$] (123 mg, 0.18 mmol) was dissolved in dry dichloromethane (2.4 mL), 1-ethyl-3-(3-dimethylaminopropyl)carbodiimide hydrochloride (101 mg, 0.53 mmol) was added, and the mixture was stirred at room temperature overnight. After confirmation of the completion of the reaction by thin layer chromatography, methanol (6.0 mL) was added and the obtained mixture was concentrated under reduced pressure. To the concentrated residue was added methanol (6.0 mL) and the obtained slurry was stirred for 15 min, and filtered. The obtained solid was dried by heating under reduced pressure to give compound 3 [TOB-suc-mo(Tr)C$^{bz}$] (218 mg, 95%).

$^1$H-NMR (400 MHz, CDCl$_3$): δ 0.88 (9H, t, J=6.8 Hz), 1.22-1.85 (98H, m), 2.54-2.68 (4H, m), 3.12-3.18 (1H, m), 3.58-3.65 (1H, m), 3.88-3.98 (6H, m), 4.07-4.15 (2H, m), 4.35-4.43 (1H, m), 5.00 (2H, s), 6.25-6.29 (1H, m), 6.53 (2H, s), 7.15-7.88 (22H, m), 8.50-8.56 (1H, m)

m/z 1569.14[M+H]$^+$

The scheme of Examples 3-12 is shown below.

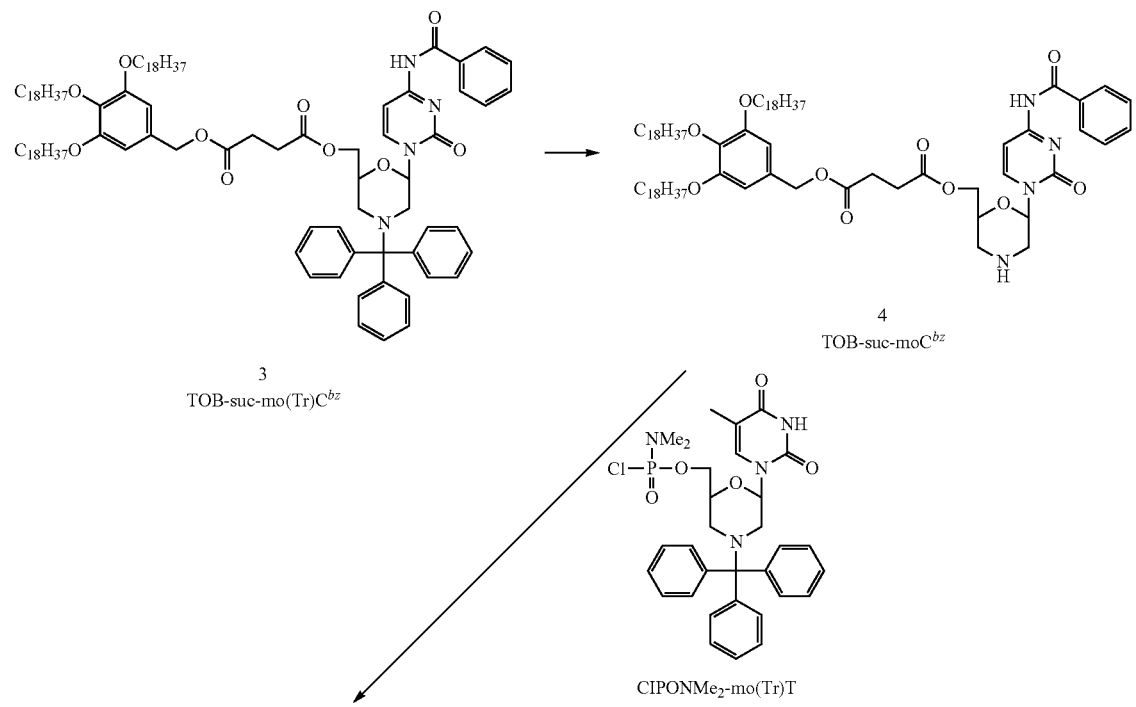

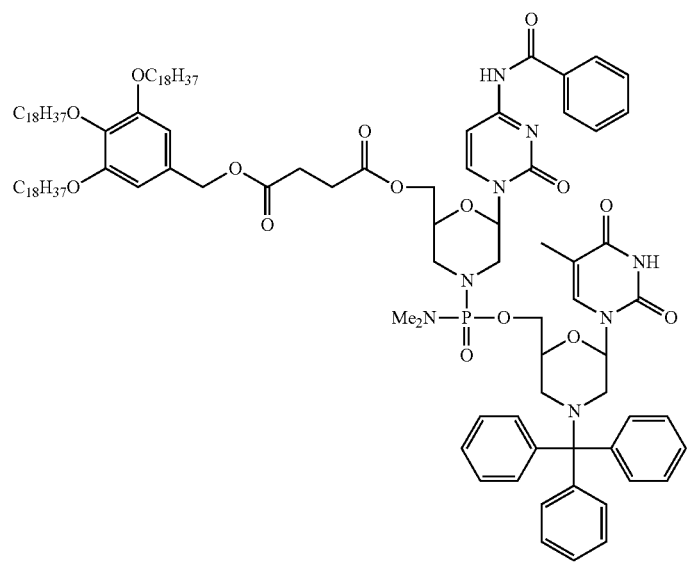
5
TOB-suc-PMO[C^{bz}T]-Tr
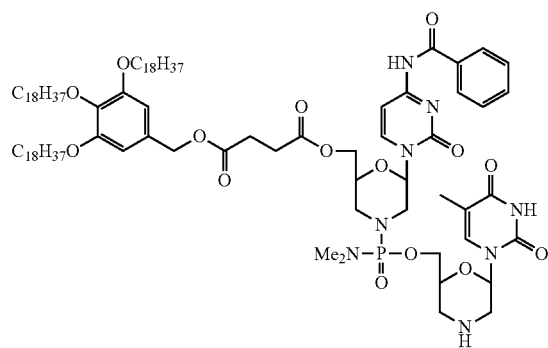
6
TOB-suc-PMO[C^{bz}T]
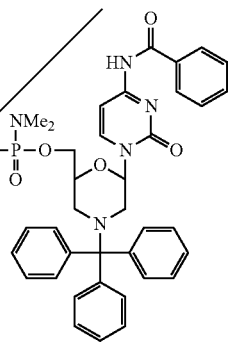
ClPONMe_2-mo(Tr)C^{bz}

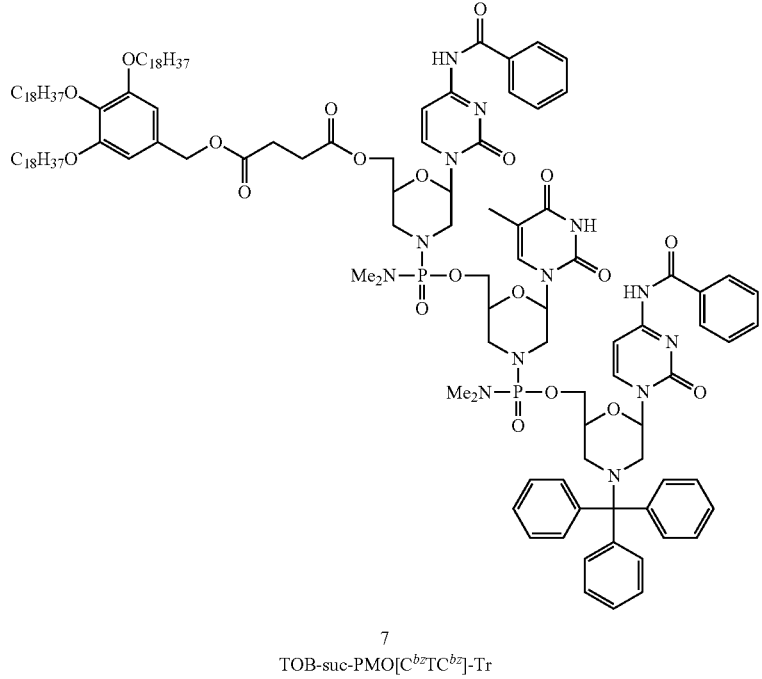

7
TOB-suc-PMO[C$^{bz}$TC$^{bz}$]-Tr

Example 3

Synthesis of Compound 4 [TOB-suc-moC$^{bz}$] (Method Using CYTFA (Salt of Cyanopyridine and Trifluoroacetic Acid) as Detritylation Agent)

Under an argon atmosphere, dichloromethane solution (1.5 mL) containing 2% CYTFA, 1% ethanol, 10% CF$_3$CH$_2$OH was added to compound 3 [TOB-suc-mo(Tr)C$^{bz}$] (62.7 mg, 0.04 mmol), and the mixture was stirred at room temperature for 30 min. After confirmation of the completion of the reaction by thin layer chromatography, dichloromethane solution (2.3 mL) containing 5% N,N-diisopropylethylamine and 25% 2-propanol was added, and the mixture was stirred at room temperature for 30 min. Then, methanol (1.5 mL) was added, and the solution was concentrated under reduced pressure. Methanol (1.5 mL) was added again to the concentrated residue, and the mixture was stirred at room temperature for 15 min. The obtained slurry was filtered, and the solid was washed with methanol (1.5 mL). The solid was dried by heating in vacuo to give detritylated compound 4 [TOB-suc-moC$^{bz}$] (52.0 mg, 98.0%).

$^1$H-NMR (400 MHz, CDCl$_3$): δ 0.88 (9H, t, J=6.9 Hz), 1.22-1.85 (96H, m), 2.45-2.53 (1H, m), 2.62-2.74 (5H, m), 2.94-3.00 (1H, m), 3.38-3.46 (1H, m), 3.89-4.00 (7H, m), 4.13-4.24 (2H, m), 4.98-5.07 (2H, m), 5.75-5.82 (1H, m), 6.54 (2H, s), 7.45-7.65 (4H, m), 7.83-8.00 (3H, m), 8.62 (1H, brs)

Example 4

Synthesis of Compound 4 [TOB-suc-moC$^{bz}$] (Method Using Cyanoacetic Acid as Detritylation Agent)

Under an argon atmosphere, dichloromethane solution (0.75 ml) containing 10% cyanoacetic acid and 20% acetonitrile was added to compound 3 [TOB-suc-mo(Tr)C$^{bz}$] (62.7 mg, 0.04 mmol), and the mixture was stirred at room temperature for 30 min. After confirmation of the completion of the reaction by thin layer chromatography, dichloromethane solution (4.5 mL) containing 5% N,N-diisopropylethylamine, and 25% 2-propanol was added, and the mixture was stirred at room temperature for 30 min. Then, methanol (1.5 mL) was added, and the solution was concentrated under reduced pressure. Methanol (1.5 mL) was added again to the concentrated residue and the mixture was stirred at room temperature for 15 min. The obtained slurry was filtered, and the solid was washed with methanol (1.5 mL). The solid was dried by heating in vacuo to give detritylated compound 4 [TOB-suc-moC$^{bz}$] (50.0 mg, 94.3%).

Example 5

Synthesis of Compound 5 [TOB-suc-PMO[C$^{bz}$-T]-Tr] (Method Using 3 Equivalents of T Monomer)

Under an argon atmosphere, to compound 4 [TOB-suc-moC$^{bz}$] (48.8 mg, 0.036 mmol) were added a solution (0.4 mL) of ClPONMe$_2$-mo(Tr)T (61 mg, 0.11 mmol) in tetrahydrofuran and 1,3-dimethyl-2-imidazolidinone solution (0.4 mL) containing 25% N,N-diisopropylethylamine, and the mixture was stirred at room temperature for 1.5 hr. After confirmation of the completion of the reaction by thin layer chromatography, methanol (1.5 mL) was added to the reaction mixture, and the solution was concentrated under reduced pressure. To the concentrated residue was added methanol (1.5 mL), and the mixture was stirred at room temperature for 15 min. The obtained slurry was filtered, and the solid was washed with methanol (1.5 mL). The solid was dried by heating in vacuo to give compound 5 [TOB-suc-PMO[C$^{bz}$-T]-Tr] (66.0 mg, 98.0%).

Example 6

Synthesis of Compound 5 [TOB-suc-PMO[$C^{bz}$-T]-Tr] (Method Using T Monomer Decreased to 1.1 Equivalents)

Under an argon atmosphere, to compound 4 [TOB-suc-moC$^{bz}$] (54.2 mg, 0.04 mmol) were added a solution (0.4 mL) of ClPONMe$_2$-mo(Tr)T (27 mg, 0.044 mmol) in tetrahydrofuran and 1,3-dimethyl-2-imidazolidinone solution (0.4 mL) containing 25% N,N-diisopropylethylamine, and the mixture was stirred at room temperature for 1.5 hr. After confirmation of the completion of the reaction by thin layer chromatography, methanol (1.5 mL) was added to the reaction mixture, and the solution was concentrated under reduced pressure. To the concentrated residue was added methanol (1.5 mL) and the mixture was stirred at room temperature for 15 min. The obtained slurry was filtered, and the solid was washed with methanol (1.5 mL). The solid was dried by heating in vacuo to give compound 5 [TOB-suc-PMO[$C^{bz}$-T]-Tr] (70.8 mg, 93.2%).

Example 7

Synthesis of Compound 5 [TOB-suc-PMO[$C^{bz}$-T]-Tr] (One-Pot Method from Compound 3)

Under an argon atmosphere, to compound 3 [TOB-suc-MO (Tr)$C^{bz}$] (62.7 mg, 0.04 mmol) was added dichloromethane solution (1.8 mL) containing 2% CYTFA, 1% ethanol, 10% CF$_3$CH$_2$OH, and the mixture was stirred at room temperature for 30 min. After confirmation of the completion of the reaction by thin layer chromatography, 5% N,N-diisopropylethylamine, and dichloromethane solution (2.7 mL) containing 25% 2-propanol were added, and the mixture was stirred at room temperature for 30 min. Then, to the reaction mixture were added a solution (0.4 mL) of ClPONMe$_2$-mo(Tr)T (73.1 mg, 0.12 mmol) in tetrahydrofuran and 1,3-dimethyl-2-imidazolidinone solution (0.5 mL) containing 25% N,N-diisopropylethylamine, and the mixture was stirred at room temperature for 30 min, and further at 38° C. for 1 hr. Methanol (1.5 mL) was added to the reaction mixture, and the solution was concentrated under reduced pressure. To the concentrated residue was added methanol (1.5 mL), and the mixture was stirred at room temperature for 15 min. The obtained slurry was filtered, and the solid was washed with methanol (1.5 mL). The solid was dried by heating in vacuo to give compound 5 [TOB-suc-PMO[$C^{bz}$-T]-Tr] (75.0 mg, 98.8%).

Example 8

Synthesis of Compound 6 [TOB-suc-PMO[$C^{bz}$-T]] (Method Using CYTFA as Detritylation Agent)

Under an argon atmosphere, to compound 5 [TOB-suc-PMO[$C^{bz}$-T]-Tr] (37.4 mg, 0.02 mmol) was added dichloromethane solution (0.75 ml) containing 2% CYTFA, 1% ethanol, 10% CF$_3$CH$_2$OH, and the mixture was stirred at room temperature for 30 min. After confirmation of the completion of the reaction by thin layer chromatography, dichloromethane solution (1.0 mL) containing 5% N,N-diisopropylethylamine, 25% 2-propanol was added, and the mixture was stirred at room temperature for 30 min. Then, methanol (1.5 mL) was added, and the solution was concentrated under reduced pressure. Methanol (1.5 mL) was added again to the concentrated residue and the mixture was stirred at room temperature for 15 min. The obtained slurry was filtered, and the solid was washed with methanol (1.5 mL). The solid was dried by heating in vacuo to give detritylated compound 6 [TOB-suc-PMO[$C^{bz}$-T]] (30.0 mg, 92.1%).

Example 9

Synthesis of Compound 6 [TOB-suc-PMO[$C^{bz}$-T] ] (Method Using Cyanoacetic Acid as Detritylation Agent)

Under an argon atmosphere, dichloromethane solution (0.38 ml) containing 10% cyanoacetic acid and 20% acetonitrile was added to compound 5 [TOB-suc-PMO[$C^{bz}$-T]-Tr] (37.4 mg, 0.02 mmol), and the mixture was stirred at room temperature for 30 min. After confirmation of the completion of the reaction by thin layer chromatography, dichloromethane solution (2.3 mL) containing 5% N,N-diisopropylethylamine and 25% 2-propanol was added, and the mixture was stirred at room temperature for 30 min. Then, methanol (1.5 mL) was added, and the solution was concentrated under reduced pressure. Methanol (1.5 mL) was added again to the concentrated residue, and the mixture was stirred at room temperature for 15 min. The obtained slurry was filtered, and the solid was washed with methanol (1.5 mL). The solid was dried by heating in vacuo to give detritylated compound 6 [TOB-suc-PMO[$C^{bz}$-T]] (31.0 mg, 95.2%).

Example 10

Synthesis of Compound 7 [TOB-suc-PMO[$C^{bz}$-T-$C^{bz}$]-Tr] (Method Using 3 Equivalents of C Monomer)

Under an argon atmosphere, to compound 6 [TOB-suc-PMO[$C^{bz}$-T]] (25.8 mg, 0.016 mmol) were added a solution (0.2 mL) of ClPONMe$_2$-mo(Tr)$C^{bz}$ (32.7 mg, 0.05 mmol) in tetrahydrofuran and 1,3-dimethyl-2-imidazolidinone solution (0.2 mL) containing 25% N,N-diisopropylethylamine, and the mixture was stirred at room temperature for 1.5 hr. After confirmation of the completion of the reaction by thin layer chromatography, methanol (1.5 mL) was added to the reaction mixture, and the solution was concentrated under reduced pressure. To the concentrated residue was added methanol (1.5 mL), and the mixture was stirred at room temperature for 15 min. The obtained slurry was filtered, and the solid was washed with methanol (1.5 mL). The solid was dried by heating in vacuo to give compound 7 [TOB-suc-PMO[$C^{bz}$-T-$C^{bz}$]-Tr] (32.9 mg, 90.9%).

Example 11

Synthesis of Compound 7 [TOB-suc-PMO-[$C^{bz}$-T-$C^{bz}$]-Tr] (Method Using C Monomer Decreased to 1.5 Equivalents)

Under an argon atmosphere, to compound 6 [TOB-suc-PMO[$C^{bz}$-T]] (99.4 mg, 0.06 mmol) were added a solution (0.6 mL) of ClPONMe$_2$-mo(Tr)$C^{bz}$ (62.8 mg, 0.09 mmol) in tetrahydrofuran and 1,3-dimethyl-2-imidazolidinone solution (0.75 mL) containing 25% N,N-diisopropylethylamine, and the mixture was stirred at room temperature for 5 hr. After confirmation of the completion of the reaction by thin layer chromatography, methanol (2.7 mL) was added to the reaction mixture, and the solution was concentrated under reduced pressure. To the concentrated residue was added methanol (2.7 mL) and the mixture was stirred at room temperature for 15 min. The obtained slurry was filtered, and the solid was washed with methanol (2.7 mL) and dried by heating in vacuo to give compound 7 [TOB-suc-PMO[$C^{bz}$-T-$C^{bz}$]-Tr] (131 mg, 94.4%).

Example 12

Synthesis of Compound 7 [TOB-suc-PMO[$C^{bz}$-T-$C^{bz}$]-Tr] (One-Pot Method from compound 5)

Under an argon atmosphere, to compound 5 [TOB-suc-PMO[$C^{bz}$-T]-Tr] (75.9 mg, 0.04 mmol) was added dichloromethane solution (1.5 mL) containing 2% CYTFA, 1% ethanol, 10% $CF_3CH_2OH$, and the mixture was stirred at room temperature for 30 min. After confirmation of the completion of the reaction by thin layer chromatography, dichloromethane solution (2.3 mL) containing 5% N,N-diisopropylethylamine and 25% 2-propanol was added, and the mixture was stirred at room temperature for 30 min. Then, to the reaction mixture were added a solution (0.4 mL) of $ClPONMe_2$-mo(Tr)$C^{bz}$ (83.8 mg, 0.12 mmol) in tetrahydrofuran and 1,3-dimethyl-2-imidazolidinone solution (0.5 mL) containing 25% N,N-diisopropylethylamine, and the mixture was stirred at room temperature for 30 min, and further stirred at 38° C. for 45 min. Methanol (1.5 mL) was added to the reaction mixture, and the solution was concentrated under reduced pressure. To the concentrated residue was added methanol (1.5 mL), and the mixture was stirred at room temperature for 15 min. The obtained slurry was filtered, and the solid was washed with methanol (1.5 mL) and dried by heating in vacuo to give compound 7 [TOB-suc-PMO[$C^{bz}$-T-$C^{bz}$]-Tr] (90.8 mg, 97.9%).

The scheme of Example 13 is shown below.

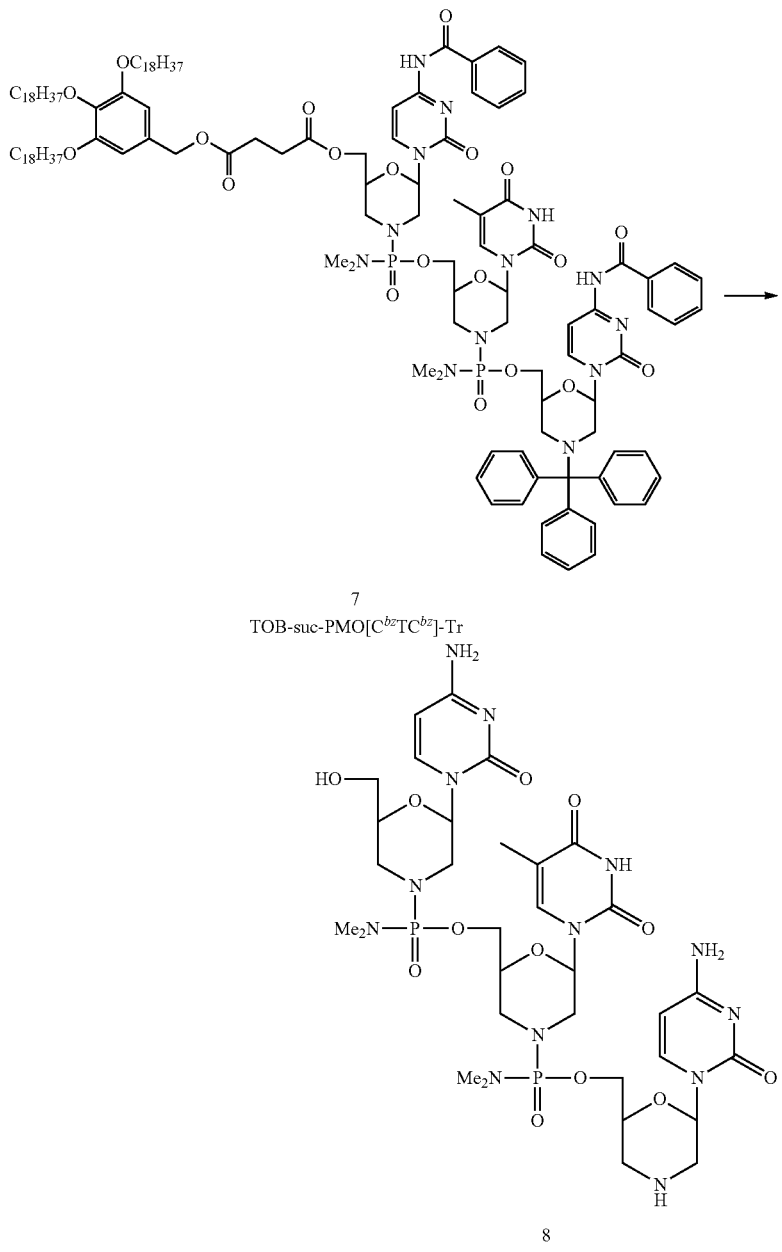

Example 13

Synthesis of Compound 8 [PMO[CTC]]

To compound 7 [TOB-suc-PMO[$C^{bz}$-T-$C^{bz}$]-Tr] (162 mg, 0.07 mmol) was added a mixture of 28% aqueous ammonia (3.5 mL) and ethanol (14.0 mL), and the mixture was sealed in an autoclave and stirred with heating at 55° C. overnight. The mixture was cooled to room temperature, and the completion of the reaction was confirmed by thin layer chromatography. The content was transferred into methanol while washing with methanol and dichloromethane. The mixture was concentrated under reduced pressure, methanol (14.0 mL) was added to the obtained concentrated residue, and the mixture was slurry washed for 30 min. The solid was filtered off and the filtrate was concentrated. The obtained solid was dissolved in 0.2 mol/l $KH_2PO_4$ aqueous solution (pH 2.0), and the mixture was stirred for 15 min. The disappearance of the starting material was confirmed by thin layer chromatography, and the mixture was adjusted to pH13-pH14 with 2.0 mol/l aqueous sodium hydroxide solution, and filtered through a membrane filter. As a result of HPLC analysis, the filtrate was identical to the object analysis reference standard.

Reversed-phase HPLC analysis (Column=InertSustain C18, 5 µm, 4.6×150 mm; Solvent A=50 mM TEAA (pH 7.0), Solvent B=$CH_3CN$; Gradient=0% to 40% B (20 min); Flow Rate=0.75 ml/min;

Temp=60° C.): RT 11.6 min, 11.7 min, 11.8 min, 12.0 min (4 isomer mixture)

The scheme of Examples 14-16 is shown below.

and 12. The weight and weight yield of the resultant product isolated in each stage are shown in the following Table.

TABLE 1

| chain length | amount obtained | weight yield |
| --- | --- | --- |
| 2mer | 96 mg | 97% |
| 3mer | 104 mg | 95% |
| 4mer | 120 mg | 100% |
| 5mer | 134 mg | 104% |
| 6mer | 138 mg | 92% |
| 7mer | 151 mg | 104% |
| 8mer | 139 mg | 89% |
| 9mer | 110 mg | 84% |
| 10mer | 101 mg | 97% |
| 11mer | 70 mg | 67% |
| 12mer | 74 mg | 94% |

Example 15

Synthesis of Compound 9 [TOB-suc-PMO[$C^{bz}$-$C^{bz}$-T-$C^{bz}$-$C^{bz}$-$G^{pac}$-$G^{pac}$-T-T-$C^{bz}$-T-$G^{pac}$]-Tr] (2 Time Isolation/1 Cycle, Method Using Cyanoacetic Acid as Detritylation Agent)

Deprotection of trityl group from compound 3 [TOB-suc-mo(Tr)$C^{bz}$] (94.1 mg, 0.06 mmol) was performed according to the methods described in Examples 4 and 9 and coupling of the corresponding monomer was sequentially performed according to the methods described in Examples 5 and 10. The weight and weight yield of the resultant product isolated in each stage are shown in the following Table.

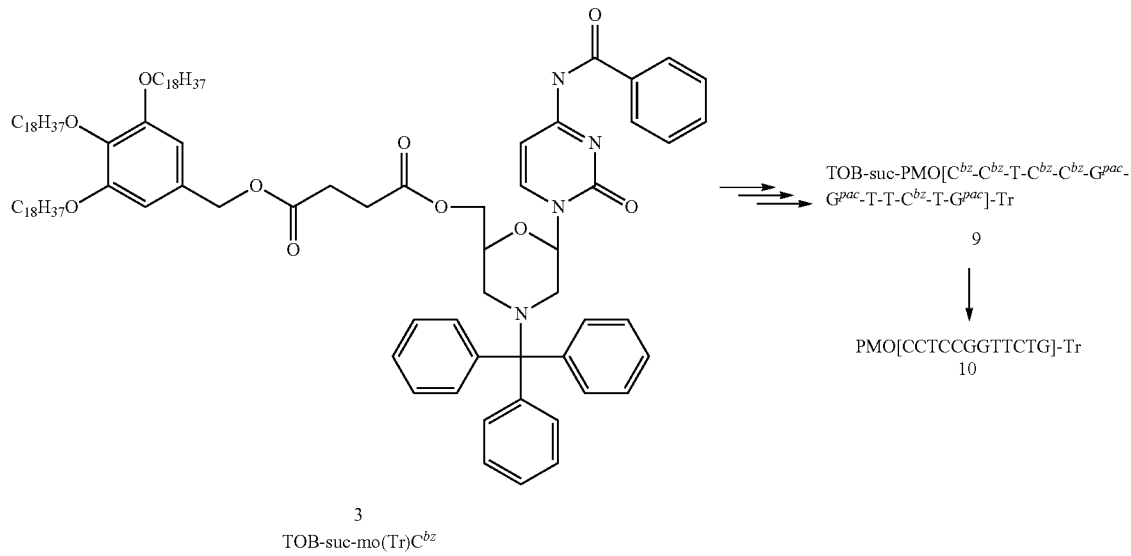

3
TOB-suc-mo(Tr)$C^{bz}$

TOB-suc-PMO[$C^{bz}$-$C^{bz}$-T-$C^{bz}$-$C^{bz}$-$G^{pac}$-$G^{pac}$-T-T-$C^{bz}$-T-$G^{pac}$]-Tr

9

↓

PMO[CCTCCGGTTCTG]-Tr

10

Example 14

Synthesis of Compound 9 [TOB-suc-PMO[$C^{bz}$-$C^{bz}$-T-$C^{bz}$-$C^{bz}$-$G^{pac}$-$G^{pac}$-T-T-$C^{bz}$-T-$G^{pac}$]-Tr] (One Time Isolation/1 Cycle Method)

Deprotection of trityl group and coupling of the corresponding monomer were sequentially performed in one pot from compound 3 [TOB-suc-mo(Tr)$C^{bz}$] (78.4 mg, 0.05 mmol) according to the methods described in Examples 7

TABLE 2

| chain length | amount obtained | weight yield |
| --- | --- | --- |
| 2mer | 112 mg | 94% |
| 3mer | 169 mg | 94% |
| 4mer | 183 mg | 94% |
| 5mer | 206 mg | 98% |
| 6mer | 216 mg | 93% |
| 7mer | 231 mg | 95% |
| 8mer | 236 mg | 96% |
| 9mer | 245 mg | 97% |

TABLE 2-continued

| chain length | amount obtained | weight yield |
| --- | --- | --- |
| 10mer | 232 mg | 88% |
| 11mer | 222 mg | 93% |
| 12mer | 218 mg | 90% |

Example 16

Synthesis of Compound 10
[PMO[CCTCCGGTTCTG]-Tr]

To compound 9 [TOB-suc-PMO[$C^{bz}$-$C^{bz}$-T-$C^{bz}$-$C^{bz}$-$G^{pac}$-$G^{pac}$-T-T-$C^{bz}$-T-$G^{pac}$]-Tr] (6.0 mg, 1.0 μmol) synthesized in Example 15 was added 28% aqueous ammonia/ethanol=1/3(v/v) (0.2 mL), and the mixture was sealed in an autoclave, and stirred with heating at 55° C. overnight. The mixture was allowed to cool to room temperature, and filtered while washing with methanol to remove the solid. The filtrate was concentrated to give a crude product (3.3 mg, 80%) of compound 10 [PMO[CCTCCGGTTCTG]-Tr].

reversed-phase HPLC analysis (Column=InertSustain C18, 5 μm, 4.6×150 mm; Solvent A=50 mM TEAA (pH 7.0), Solvent B=$CH_3CN$; Gradient=10% to 70% B (20 min); Flow Rate=0.75 ml/min; Temp=60° C.): RT 13.1 min The scheme of Examples 17 and 18 is shown below.

Example 17

Synthesis of Compound 11 [TOB-suc-PMO[$C^{bz}$-$C^{bz}$-T-$C^{bz}$-$C^{bz}$-$G^{pac}$-$G^{pac}$-T-T-$C^{bz}$-T-$G^{pac}$-$A^{bz}$-$A^{bz}$-$G^{pac}$-$G^{pac}$-T-$G^{pac}$-T-T-$C^{bz}$]-Tr]

Deprotection of trityl group from compound 3 [TOB-suc-mo(Tr)$C^{bz}$] (78.4 mg, 0.05 mmol) was performed according to the methods described in Examples 3 and 8, and coupling of the corresponding monomer was sequentially performed according to the methods described in Examples 5 and 10. The weight and weight yield of the resultant product isolated in each stage are shown in the following Table.

TABLE 3

| chain length | amount obtained | weight yield |
| --- | --- | --- |
| 2mer | 92 mg | 92% |
| 3mer | 89 mg | 86% |
| 4mer | 98 mg | 95% |
| 5mer | 103 mg | 91% |
| 6mer | 111 mg | 95% |
| 7mer | 123 mg | 98% |
| 8mer | 112 mg | 85% |
| 9mer | 103 mg | 87% |
| 10mer | 95 mg | 86% |
| 11mer | 93 mg | 94% |
| 12mer | 92 mg | 92% |

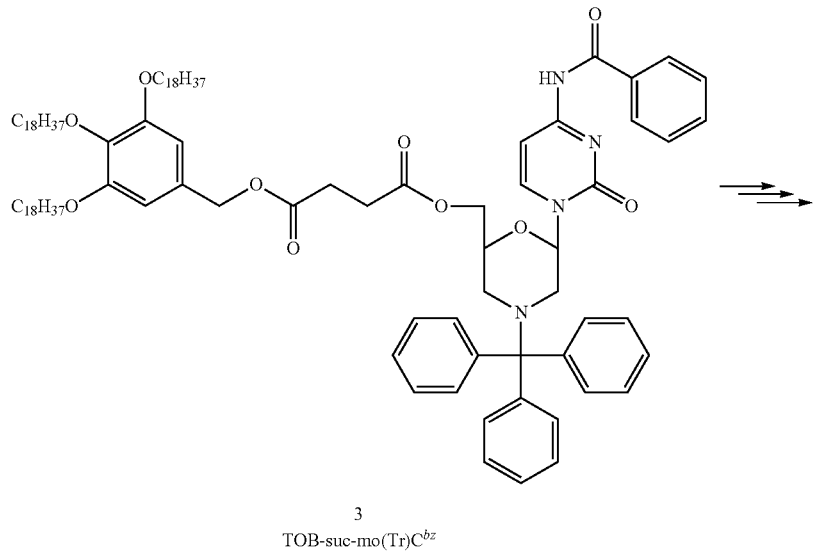

3
TOB-suc-mo(Tr)$C^{bz}$

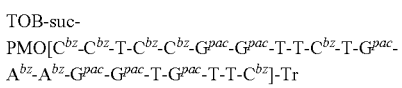

11

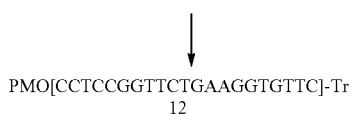

12

TABLE 3-continued

| chain length | amount obtained | weight yield |
| --- | --- | --- |
| 13mer | 87 mg | 90% |
| 14mer | 84 mg | 90% |
| 15mer | 82 mg | 92% |
| 16mer | 79 mg | 91% |

TABLE 3-continued

| chain length | amount obtained | weight yield |
| --- | --- | --- |
| 17mer | 71 mg | 86% |
| 18mer | 65 mg | 86% |
| 19mer | 49 mg | 74% |
| 20mer | 37 mg | 75% |
| 21mer | 25 mg | 66% |

Example 18

Synthesis of Compound 12 [PMO[CCTCCGGTTCTGAAGGTGTTC]-Tr]

Compound 11 [TOB-suc-PMO[$C^{bz}$-$C^{bz}$-T-$C^{bz}$-$C^{bz}$-$G^{pac}$-T-T-$C^{bz}$-T-$G^{Pac}$-$A^{bz}$-$A^{bz}$-$G^{pac}$-$G^{pac}$-T-$G^{pac}$-T-T-$C^{bz}$]-Tr] (6 mg, 0.61 mmol) was dissolved in 28% aqueous ammonia/ethanol=1/3(v/v) (200 μl), and the mixture was sealed in an autoclave and stirred at 55° C. overnight. The mixture was allowed to cool to room temperature, and filtered while washing with methanol to remove the solid. The filtrate was concentrated to give a crude product (3.1 mg, 71%) of compound 12 [PMO[CCTCCGGTTCTGAAGGTGTTC]-Tr].

Reversed-phase HPLC analysis (Column=Inert Sustain C18, 5 μm, 4.6×150 mm; Solvent A=50 mM TEAA (pH 7.0), Solvent B=$CH_3CN$; Gradient=10% to 70% B (20 min); Flow Rate=0.75 ml/min; Temp=60° C.): RT 12.4 min Anion exchange HPLC analysis (Column=DNAPacPA-100, 4.0×250 mm; Solvent A=10 mM NaOH aqueous solution, B=1M NaCl, 10 mM NaOH aqueous solution; Gradient=20% to 100% B (30 min); Flow Rate=1.0 mL/min; Temp=35° C.): RT 10.8 min m/z 7167.50 $[M+H]^+$ The scheme of Examples 19 and 20 is shown below.

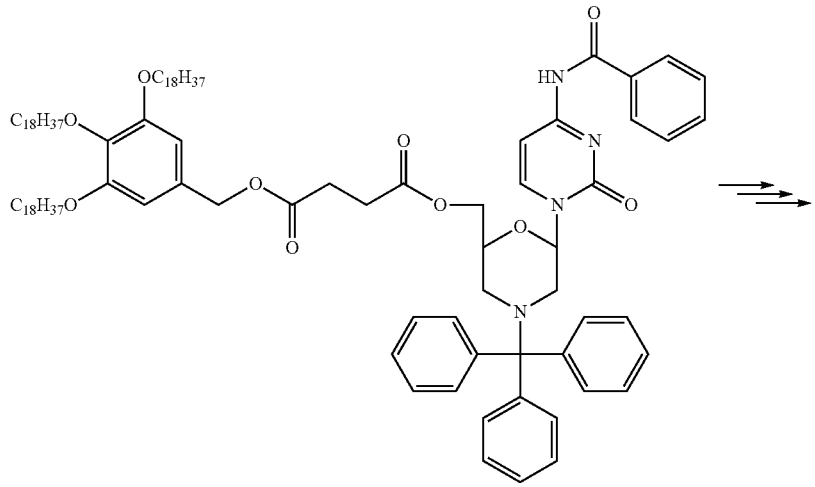

3
TOB-suc-mo(Tr)$C^{bz}$

TOB-suc-PMO[$C^{bz}$-$C^{bz}$-T-$C^{bz}$-$C^{bz}$-$G^{ce/pac}$-$G^{ce/pac}$-T]-Tr
13

PMO[CCTCCGGT]-Tr
14

Example 19

Synthesis of Compound 13 [TOB-suc-PMO[$C^{bz}$-$C^{bz}$-T-$C^{bz}$-$C^{bz}$-$G^{ce/pac}$-$G^{ce/pac}$-T]-Tr]

Deprotection of trityl group from compound 3 [TOB-suc-mo(Tr)$C^{bz}$] (502 mg, 0.32 mmol) was performed according to the methods described in Examples 3 and 8, and coupling of the corresponding monomer was sequentially performed according to the methods described in Examples 5 and 10. As a monomer corresponding to guanosine, ClPONMe$_2$-mo(Tr)$G^{ce/pac}$ having a cyanoethyl group at the O6-position as a protecting group was used. The weight and weight yield of the resultant product isolated in each stage are shown in the following Table.

TABLE 4

| chain length | amount obtained | weight yield |
| --- | --- | --- |
| 2mer | 536 mg | 87% |
| 3mer | 576 mg | 94% |
| 4mer | 632 mg | 96% |
| 5mer | 694 mg | 97% |
| 6mer | 732 mg | 92% |
| 7mer | 682 mg | 92% |
| 8mer | 572 mg | 89% |

Example 20

Synthesis of Compound 14 [PMO[CCTCCGGT]-Tr]

Compound 13 [TOB-suc-PMO[$C^{bz}$-$C^{bz}$-T-$C^{bz}$-$C^{bz}$-$G^{ce/pac}$-$G^{ce/pac}$-T]-Tr] (19.3 mg, 4.2 µmol) synthesized in Example 19 was suspended in 28% aqueous ammonia/ethanol=1/3(v/v) (2.0 mL), and the suspension was sealed in an autoclave and stirred with heating overnight at 55° C. After allowing to cool to room temperature, the liquid was transferred using dichloromethane (1.5 mL) and methanol (1.5 mL) into an eggplant-shaped flask, and concentrated under reduced pressure. To the concentrated residue was added methanol (2.0 mL) and the precipitated solid was filtered through a membrane filter. The filtrate was concentrated to dryness to quantitatively give compound 14 [PMO[CCTCCGGT]-Tr].

m/z 929.2[M+3H]$^{3+}$, 1393.3[M+2H]$^{2+}$

The scheme of Examples 21 and 22 is shown below.

TOB-suc-PMO[$C^{bz}$-$C^{bz}$-T-$C^{bz}$-$C^{bz}$- 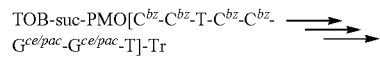
$G^{ce/pac}$-$G^{ce/pac}$-T]-Tr

13

TOB-suc
PMO[$C^{bz}$-$C^{bz}$-T-$C^{bz}$-$C^{bz}$-$G^{ce/pac}$-$G^{ce/pac}$-
T-T-$C^{bz}$-T-$G^{ce/pac}$-$A^{bz}$]-Tr

15

PMO[CCTCCGGTTCTGA]-Tr

16

Example 21

Synthesis of Compound 15 [TOB-suc-PMO[$C^{bz}$-$C^{bz}$-T-$C^{bz}$-$C^{bz}$-$G^{ce/pac}$-$G^{ce/pac}$-T-T-$C^{bz}$-T-$G^{ce/pac}$-$A^{bz}$]-Tr]

Using compound 13 [TOB-suc-PMO[$C^{bz}$-$C^{bz}$-T-$C^{bz}$-$C^{bz}$-$G^{ce/pac}$-$G^{ce/pac}$-T]-Tr] (487 mg, 0.11 mmol) synthesized in Example 19 and according to the method described in Example 12, deprotection of trityl group and coupling with the corresponding monomer were performed. As a monomer corresponding to guanosine, ClPONMe$_2$-mo(Tr)$G^{ce/pac}$ having a cyanoethyl group at the O6-position as a protecting group was used. The weight and weight yield of the resultant product isolated in each stage are shown in the following Table.

TABLE 5

| chain length | amount obtained | weight yield |
| --- | --- | --- |
| 9mer | 429 mg | 86% |
| 10mer | 400 mg | 93% |
| 11mer | 308 mg | 86% |
| 12mer | 267 mg | 86% |
| 13mer | 208 mg | 92% |

Example 22

Synthesis of Compound 16 [PMO[CCTCCGGTTCTGA]-Tr]

Compound 15 [TOB-suc-PMO[$C^{bz}$-$C^{bz}$-T-$C^{bz}$-$C^{bz}$-$G^{ce/pac}$-$G^{ce/pac}$-T-T-$C^{bz}$-T-$G^{ce/pac}$-$A^{bz}$]-Tr] (8.6 mg, 1.3 µmol) synthesized in Example 21 was suspended in 28% aqueous ammonia/ethanol=1/3(v/v) (1.0 mL), and the suspension was sealed in an autoclave and stirred with heating overnight at 55° C. After allowing to cool to room temperature, the liquid was transferred using dichloromethane (1.0 mL) and methanol (1.0 mL) into an eggplant-shaped flask, and concentrated under reduced pressure. To the concentrated residue was added methanol (1.0 mL) and the precipitated solid was filtered off through a membrane filter. The filtrate was concentrated to dryness to quantitatively give compound 16 [PMO[CCTCCGG]-Tr].

m/z 1114.8[M+4H]$^{4+}$, 1486.0[M+3H]$^{3+}$

The scheme of Examples 23 and 24 is shown below.

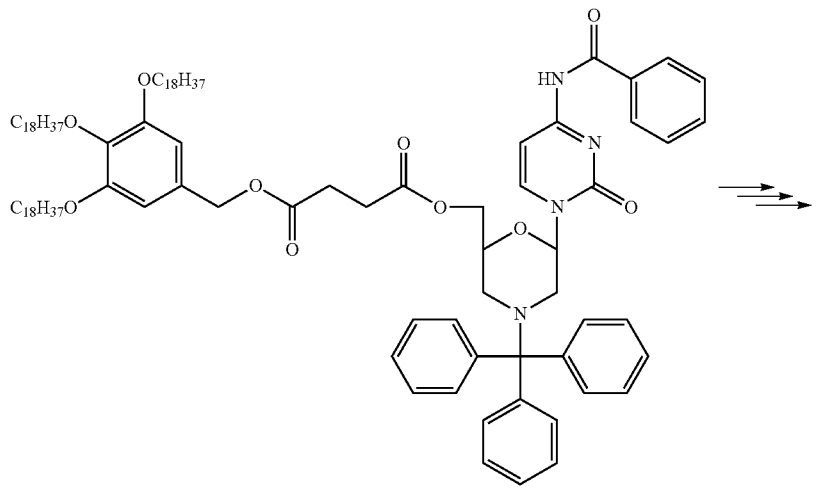

3
TOB-suc-mo(Tr)$C^{bz}$

-continued

TOB-suc-PMO[$C^{bz}$-$C^{bz}$-T-$C^{bz}$-$C^{bz}$-$G^{ce/pac}$-$G^{ce/pac}$]-Tr
17

↓

PMO[CCTCCGG]-Tr
18

Example 23

Synthesis of Compound 17 [TOB-suc-PMO[$C^{bz}$-$C^{bz}$-T-$C^{bz}$-$C^{bz}$-$G^{ce/pac}$-$G^{ce/pac}$]-Tr]

Under an argon atmosphere, to compound 3 [TOB-suc-mo(Tr)$C^{bz}$] (300 mg, 0.19 mmol) was added dichloromethane solution (8.0 ml) containing 2% CYTFA, 1% ethanol, 10% CF$_3$CH$_2$OH, and the mixture was stirred at room temperature for 90 min. After confirmation of the completion of the reaction by thin layer chromatography, dichloromethane solution (12.0 mL) containing 5% N,N-diisopropylethylamine and 25% 2-propanol was added, and the mixture was stirred at room temperature for 30 min. This solution was concentrated under reduced pressure. Acetonitrile (8.0 mL) was added and the mixture was stirred at room temperature for 15 min. The obtained slurry was filtered, and the solid was washed with acetonitrile (8.0 mL) and dried by heating in vacuo to give detritylated compound 4 [TOB-suc-mo$C^{bz}$] (254 mg, 100%).

Under an argon atmosphere, to compound 4 [TOB-suc-mo$C^{bz}$] (242 mg, 0.18 mmol) were added a solution of ClPONMe$_2$-mo(Tr)$C^{bz}$ (382 mg, 0.55 mmol) in tetrahydrofuran (1.8 mL) and 1,3-dimethyl-2-imidazolidinone solution (2.0 mL) containing 25% N,N-diisopropylethylamine, and the mixture was stirred at room temperature for 30 min. After confirmation of the completion of the reaction by thin layer chromatography, morpholine (48 μL, 0.55 mmol) was added to the reaction mixture, and the mixture was stirred for 10 min. Then, acetonitrile (7.3 mL) was added to the solution and the mixture was concentrated under reduced pressure. To the concentrated residue was added acetonitrile (7.3 mL) again, and the obtained slurry was stirred for 15 min. The slurry was filtered, and the obtained solid was washed with acetonitrile (7.3 mL) and dried by heating under reduced pressure to give TOB-suc-PMO[Cbz-Cbz]-Tr (355 mg, 98%).

Hereafter, detritylation and coupling with the corresponding monomer were sequentially performed to give the title compound 17 [TOB-suc-PMO[$C^{bz}$-$C^{bz}$-T-$C^{bz}$-$C^{bz}$-$G^{ce/pac}$-$G^{ce/pac}$]-Tr]. The weight and weight yield of the resultant product isolated in each stage are shown in the following Table.

TABLE 6

| chain length | amount obtained | weight yield |
|---|---|---|
| 2mer | 355 mg | 98% |
| 3mer | 399 mg | 110% |
| 4mer | 358 mg | 87% |
| 5mer | 372 mg | 100% |
| 6mer | 386 mg | 98% |
| 7mer | 306 mg | 77% |

Example 24

Synthesis of Compound 18 [PMO[CCTCCGG]-Tr]

The compound 17 [TOB-suc-PMO[$C^{bz}$-$C^{bz}$-T-$C^{bz}$-$C^{bz}$-$G^{ce/pac}$-$G^{ce/pac}$]-Tr] (4 mg, 0.94 μmol) synthesized in Example 23 was subjected to deprotection according to the method described in Example 22 and detachment from the carrier to give compound 18 [PMO[CCTCCGG]-Tr].

m/z 819.3[M+3H]$^{3+}$, 1228.4[M+2H]$^{2+}$

Example 25

[TOB-suc-PMO[$C^{bz}$-$C^{bz}$]] (One-Pot Elongation)

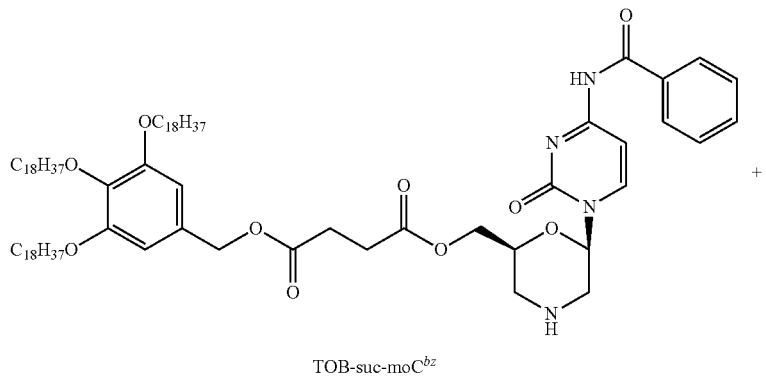

TOB-suc-mo$C^{bz}$

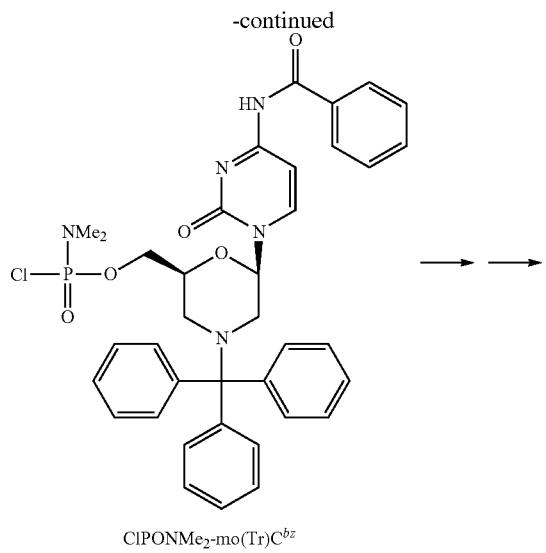

ClPONMe₂-mo(Tr)C^bz

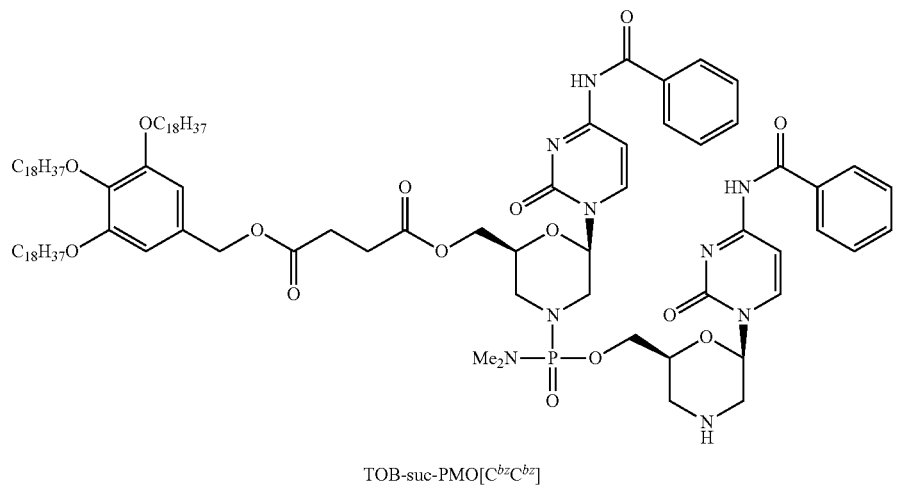

TOB-suc-PMO[C^bzC^bz]

TOB-suc-moC^bz (395 mg, 0.30 mmol) was dissolved in dichloromethane (4 mL), DIEA (1.8 eq, 0.54 mmoL, 50 µl), and ClPONMe₂-mo(Tr)C^bz (1.5 eq, 0.45 mmoL, 312 mg) were added in 3 portions at 30 min intervals in an ice bath, and the mixture was stirred at room temperature overnight. Then, DIEA (0.1 eq, 0.03 mmoL, 5 µl), ClPONMe₂-mo(Tr)C^bz (0.1 eq, 0.03 mmoL, 21 mg) were added 3 times each, and the mixture was further stirred overnight. After completion of the reaction, morpholine (1.28 eq, 0.37 mmoL, 34 µl) was added, and the mixture was stirred for 1.5 hr. The disappearance of remaining ClPONMe₂-mo(Tr)C^bz was confirmed, SOLUTION A (16.8 mL) of Reference Example 2 was slowly added dropwise over 10 min, and the mixture was stirred for 2 hr at room temperature. After completion of the detritylation reaction, a diluted solution of DIEA (142 µL, 1.0 eq vs TFA)/dichloromethane (1 mL) was slowly added in an ice bath, and MeCN (50 ml) was added to allow for precipitation. The precipitate in the suspension was filtered, and the filtrate was washed with MeCN to give [TOB-suc-PMO[C^bz-C^bz]] (wet. 526 mg).

TOF-MS+ (m/z) 1743.8

Example 26
Synthesis of [TOB-suc-PMO[C$^{bz}$-C$^{bz}$-T]] (Condensation 3 and One-Pot Elongation)
[TOB-suc-PMO[C$^{bz}$-C$^{bz}$]] as wet crystals (wet. 526 mg) was dissolved in dichloromethane (10 ml) in an ice bath, DIEA (0.54 mmol, 50 µl), and ClPONMe$_2$-mo(Tr)T (0.45 mmol, 272 mg) was added in 3 portions at 30 min intervals. The mixture was stirred at room temperature overnight.
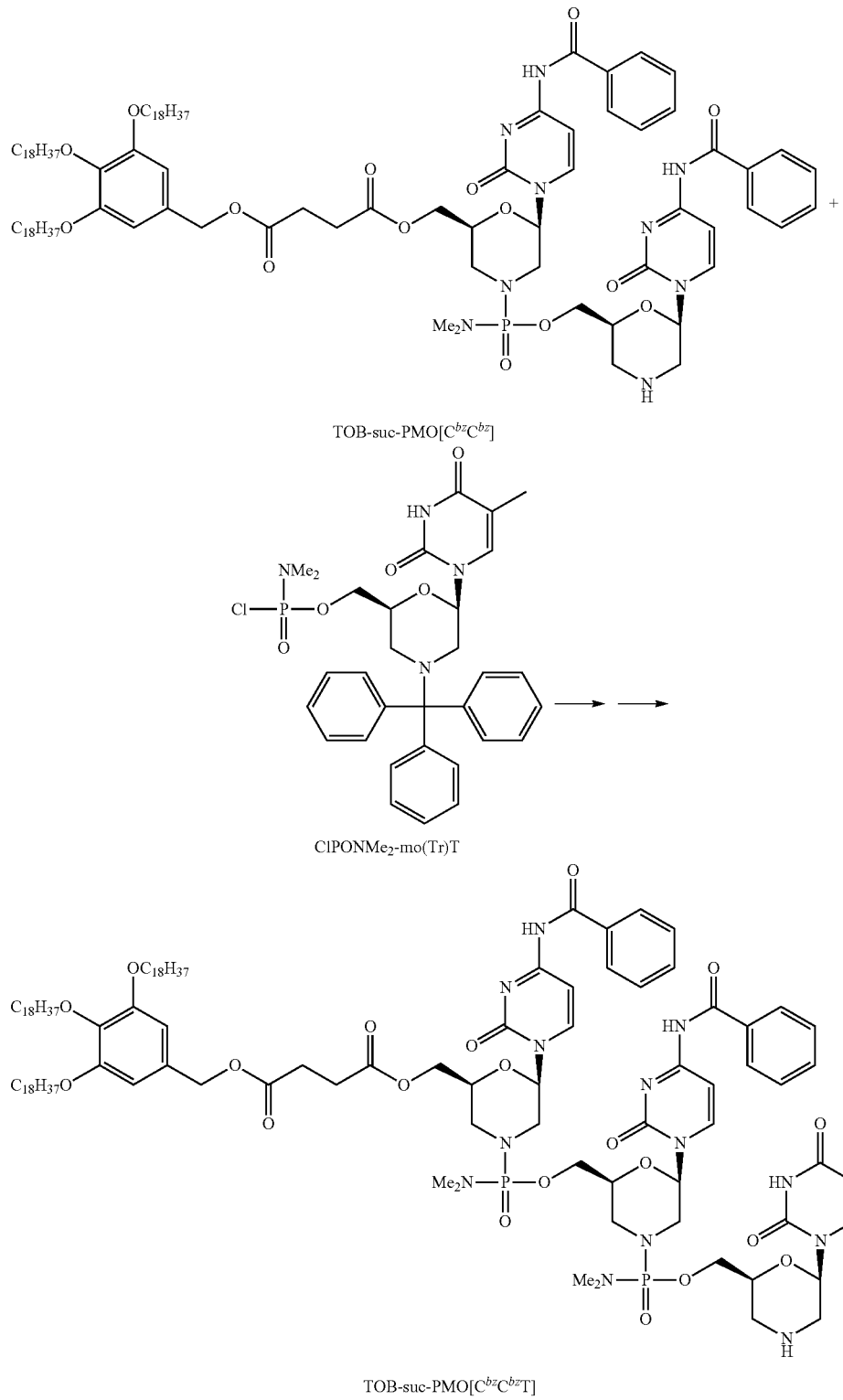

Then, DIEA (0.03 mmol, 3 μl), and ClPONMe$_2$-mo(Tr)T (0.03 mmol, 17 mg) were added twice, and the mixture was stirred at room temperature for 4 hr. After completion of the reaction, morpholine (0.5 eq, 0.14 mmoL, 21 μl) was added at ambient temperature, and the mixture was stirred for 3 hr. SOLUTION A (30 ml) of Reference Example 2 was slowly added dropwise over 15 min in an ice bath and, after the completion of the dropwise addition, the mixture was stirred at room temperature for 4 hr. After completion of the reaction, a diluted solution of DIEA (77 μl)/dichloromethane (1 ml) was slowly added in an ice bath and MeCN (50 ml) was added to give a white slurry. 25 ml of this liquid was evaporated under reduced pressure, MeCN (20 ml) was added, and the slurry was stirred for 15 min and filtered. The obtained crystals were wash again with MeCN (30 ml) and dried under reduced pressure to give [TOB-suc-PMO[C$^{bz}$-C$^{bz}$-T]] (yield 95%) (vs TOB-suc-moC$^{bz}$).

TOF-MS+ (m/z) 2073.4

Comparative Example 1

Evaluation of Influence of Quenching of Excess Monomer by Morpholine on Quality

The 2mer to 5mer intermediates obtained on the way of synthesis described in Example 14 were subjected to deprotection by the method described in Example 14 and detachment from the carrier, and impurity analysis was performed by mass spectrometry (LC-MS). Similarly, the 2mer to 7mer intermediates obtained on the way of synthesis described in Example 23 were also subjected to deprotection and detachment from the carrier, and impurity analysis was performed by mass spectrometry (LC-MS). The respective analysis results were compared. It was found that the method described in Example 23 wherein excess monomer was quenched by morpholine was free of byproduction of impurity in excess elongation such as n+1 mer and the like.

TABLE 7

| without morpholine quenching | | |
|---|---|---|
| chain length | object product | (n + x) |
| 2mer | CC | not detected |
| 3mer | CCT | CCT + C was observed |
| 4mer | CCTC | CCTC + C, CCTC + T were observed |
| 5mer | CCTCC | CCTCC + C, CCTCC + T were |
| with morpholine quenching | | |
| chain length | object product | (n + x) |
| 2mer | CC | not detected |
| 3mer | CCT | not dectected |

TABLE 7-continued

| 4mer | CCTC | trace amount of CCTC + C, CCTC + T were observed |
|---|---|---|
| 5mer | CCTCC | not detected |
| 6mer | CCTCCG | not detected |
| 7mer | CCTCCGG | not detected |

*Indication of terminal trityl group is omitted.

Example 27

Synthesis of DPM-suc-mo(Tr)C$^{bz}$

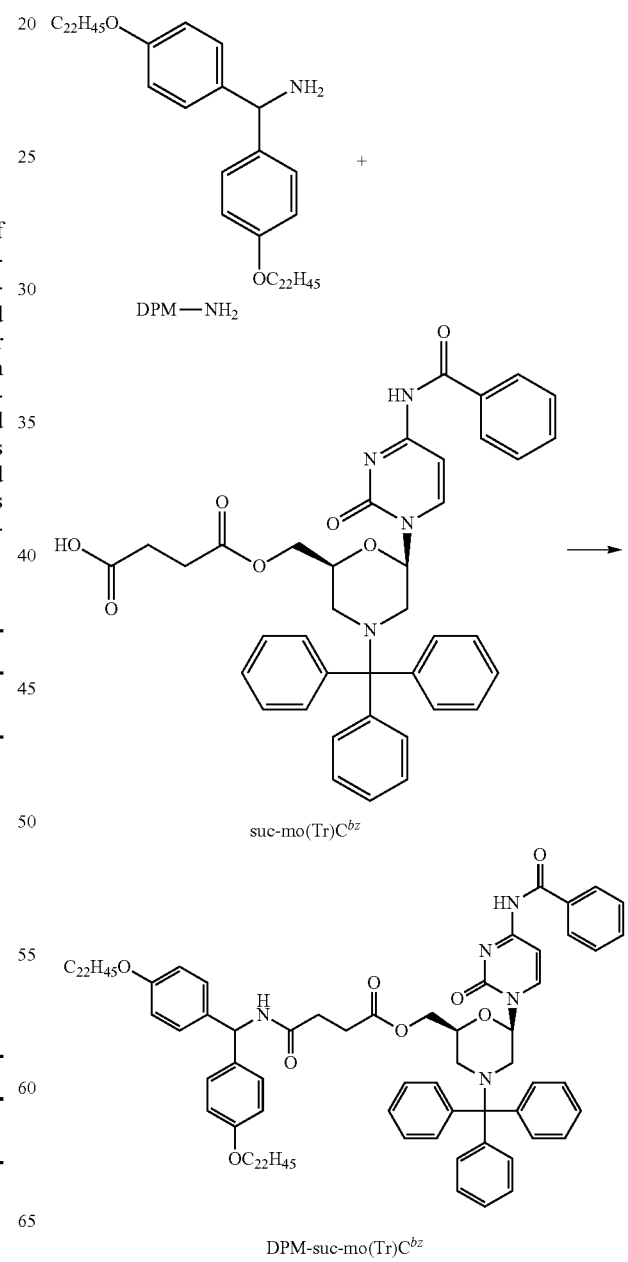

α,α-Di-4,4'-docosyloxyphenylmethylamine (1.0 g, 1.20 mmol) was dissolved in chloroform (20 mL), HOBt (162.3 mg, 1.20 mmol), suc-mo(Tr)$C^{bz}$ (969.8 mg, 1.44 mmol) and EDC.HCl (152.0 mg, 0.79 mmol) were added and the mixture was stirred at room temperature for 20 min. Then, to the reaction mixture was added again EDC.HCl (152.0 mg, 0.79 mmol), and the mixture was stirred at room temperature for 24 hr. After confirmation of the completion of the reaction by UHPLC, the solvent was evaporated under reduced pressure. To the obtained residue was added acetonitrile (10 mL), and the precipitates were collected by filtration. The obtained crystals were washed again with acetonitrile (10 mL) and dried under reduced pressure to give DPM-suc-mo(Tr)$C^{bz}$ (1.70 g, yield 96%).

TOF-MS+ (m/z) 1486.9

The scheme of Examples 28 and 29 is shown below.

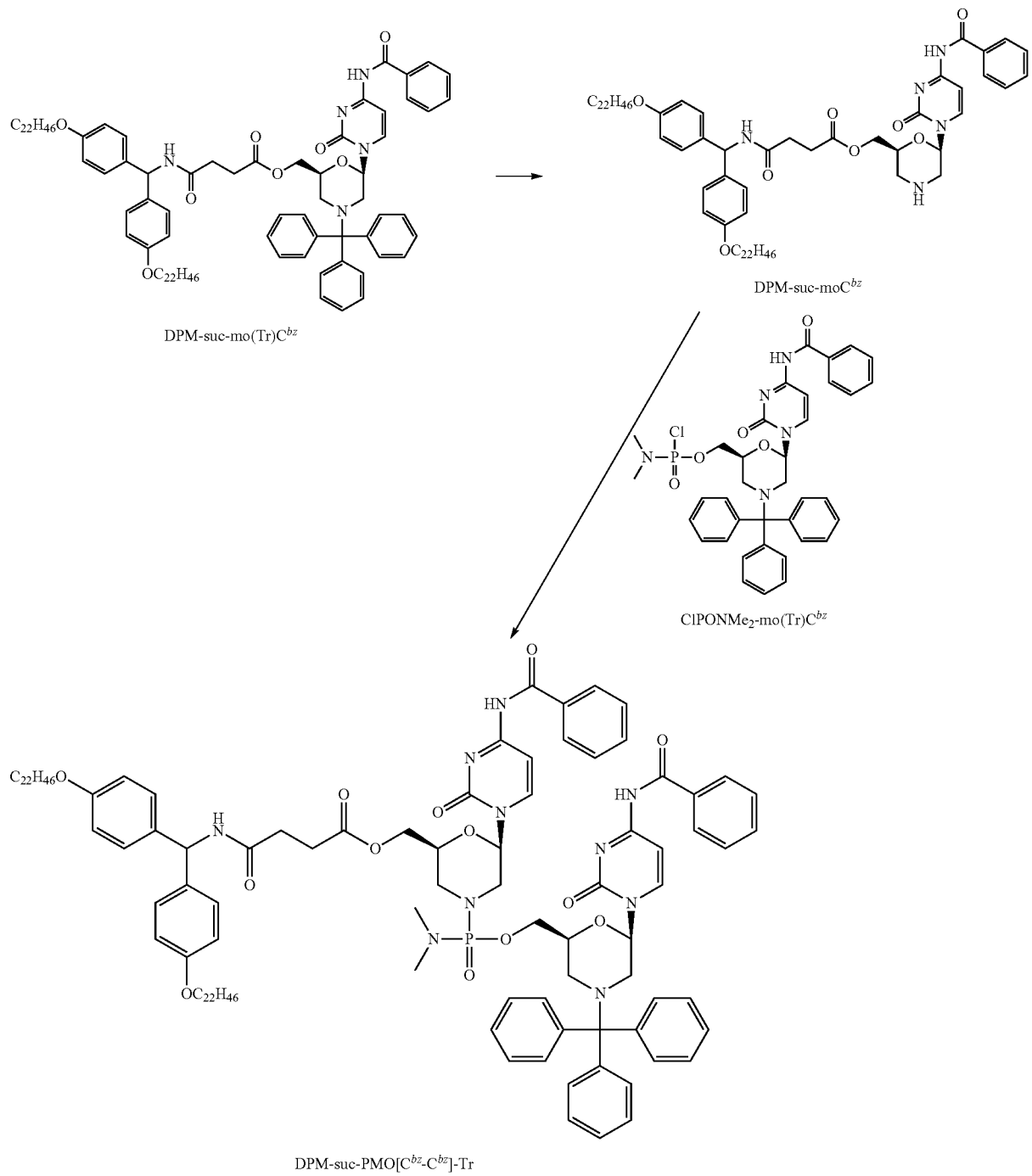

Example 28

Synthesis of DPM-suc-mo$C^{bz}$

DPM-suc-mo(Tr)$C^{bz}$ (1.69 g, 1.13 mmol) was dissolved in chloroform (16.9 mL), and ice-cooled. 2,2,2-Trifluoroethanol (4.3 mL) and ethanol (0.52 g, 11.3 mmol) were added, a solution of trifluoroacetic acid (1.03 g, 9.07 mmol) and triethylamine (0.57 g, 5.67 mmol) in chloroform (7.0 mL) was added dropwise, and the mixture was stirred at 15° C. for 1 hr. After confirmation of the completion of the reaction by UHPLC, the reaction mixture was ice-cooled and a solution of N,N-diisopropylethylamine (0.59 g, 4.54 mmol) in chloroform (6 mL) was added dropwise. To the reaction mixture was added acetonitrile (16.9 mL) and the solvent was evaporated under reduced pressure. To the obtained residue was added acetonitrile (16.9 mL), and the mixture was stirred at 0° C. for 30 min, and the precipitates were collected by filtration. The obtained crystals were washed again with acetonitrile (16.9 mL) to give DPM-suc-moC$^{bz}$. The crystals were directly used without drying as a starting material of the next reaction.

TOF-MS+ (m/z) 1244.9

Example 29

Synthesis of DPM-suc-PMO[C$^{bz}$-C$^{bz}$]-Tr

DPM-suc-moC$^{bz}$ wet crystals (3.33 g, corresponding to 1.13 mmol) were dissolved in chloroform (9.8 mL), and cyclohexane (4.2 mL) was added. N,N-diisopropylethylamine (0.26 g, 2.03 mmol) and ClPONMe$_2$-mo(Tr)C$^{bz}$ (1.18 g, 1.69 mmol) were added, and the mixture was stirred at 40° C. for 21 hr with heating. After confirmation of the completion of the reaction by UHPLC, the reaction mixture was cooled to room temperature, morpholine (0.20 g, 2.25 mmol) was added and the mixture was stirred for 1 hr. To the reaction mixture was added acetonitrile (14 mL), and the solvent was evaporated under reduced pressure. The obtained slurry was stirred at 0° C. and the precipitates were collected by filtration. The obtained crystals were washed again with acetonitrile (14 mL), and dried under reduced pressure to give DPM-suc-PMO[C$^{bz}$-C$^{bz}$]-Tr (1.96 g, yield 91%).

TOF-MS+ (m/z) 1906.3

Example 30

Synthesis of TOB-suc-PMO[C$^{bz}$-C$^{bz}$]-MMTr

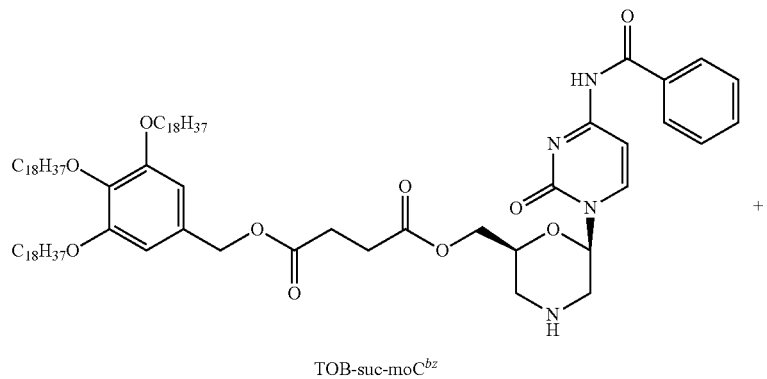

TOB-suc-moC$^{bz}$

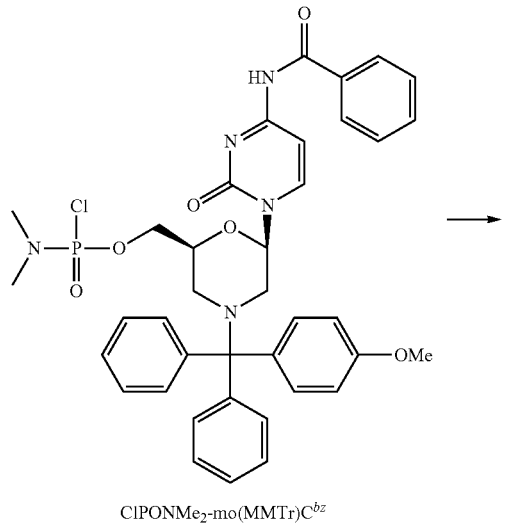

ClPONMe$_2$-mo(MMTr)C$^{bz}$

-continued

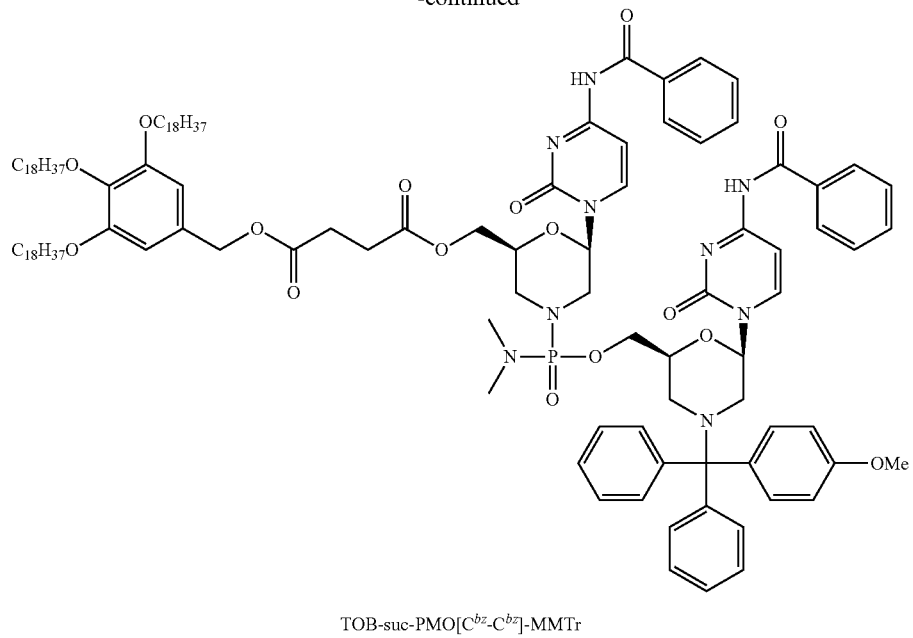

TOB-suc-PMO[C$^{bz}$-C$^{bz}$]-MMTr

TOB-suc-mo(Tr)C$^{bz}$(1.0 g, 0.64 mmol) was dissolved in chloroform (10 mL), and ice-cooled. 2,2,2-trifluoroethanol (2.8 mL) and ethanol (0.29 g, 6.4 mmol) were added, a solution of trifluoroacetic acid (0.29 g, 2.55 mmol) and triethylamine (0.14 g, 1.27 mmol) in chloroform (4.5 mL) was added dropwise, and the mixture was stirred at room temperature for 2 hr. After confirmation of the completion of the reaction by UHPLC, the reaction mixture was ice-cooled, and a solution of N,N-diisopropylethylamine (0.33 g, 2.55 mmol) in chloroform (3 mL) was added dropwise. To the reaction mixture was added acetonitrile (30 mL), and the solvent was evaporated under reduced pressure. To the obtained residue was added acetonitrile (20 mL), and the mixture was stirred at 0° C. for 30 min, and the precipitates were collected by filtration. The obtained crystals were washed again with acetonitrile (20 mL) to give TOB-suc-moC$^{bz}$. The crystals were directly used without drying as a starting material of the next reaction.

TOB-suc-moC$^{bz}$ wet crystals (1.39 g, corresponding to 0.64 mmol) were dissolved in chloroform (10 mL), N,N-diisopropylethylamine (0.15 g, 1.15 mmol) and ClPONMe$_2$-mo(MMTr)C$^{bz}$ (695 mg, 0.96 mmol) were added, and the mixture was stirred at room temperature for 17 hr. After confirmation of the completion of the reaction by UHPLC, to the obtained solution was added acetonitrile (20 mL), and the precipitates were collected by filtration. The obtained crystals were washed again with acetonitrile (20 mL) and dried under reduced pressure to give TOB-suc-PMO[C$^{bz}$-C$^{bz}$]-MMTr (1.19 g, yield 92%).

TOF-MS+ (m/z) 2017.3

Example 31

Synthesis of TOB-suc-PMO[C$^{bz}$-T] (Elongation-2)

TOB-suc-moC$^{bz}$ (4.3 g, 3.23 mmol) was dissolved in chloroform (33 mL), N,N-diisopropylethylamine (0.73 g, 5.81 mmol) and ClPONMe$_2$-mo(Tr)T (2.95 g, 4.85 mmol) were added, and the mixture was stirred at room temperature for 19 hr. After confirmation of the completion of the reaction by UHPLC, the reaction mixture was cooled to room temperature, morpholine (0.28 g, 3.23 mmol) was added and the mixture was stirred at room temperature for 1 hr. The reaction mixture was ice-cooled, 2,2,2-trifluoroethanol (13.1 mL) and ethanol (1.49 g, 32.3 mmol) were added, a solution of trifluoroacetic acid (2.95 g, 25.8 mmol) and triethylamine (1.21 g, 12.0 mmol) in chloroform (9.9 mL) was added dropwise, and the mixture was stirred at 15° C. for 1.5 hr. After confirmation of the completion of the reaction by UHPLC, the reaction mixture was ice-cooled, and a solution of N,N-diisopropylethylamine (3.26 g, 25.8 mmol) in chloroform (4.5 mL) was added dropwise. To the reaction mixture was added acetonitrile (86 mL), and the solvent was evaporated under reduced pressure. The obtained slurry was stirred at 0° C. for 30 min, and the precipitates were collected by filtration. The obtained crystals were washed again with acetonitrile (43 mL) to give TOB-suc-PMO[C$^{bz}$-T]. The crystals were directly used without drying as a starting material of the next reaction.

Example 32

Synthesis of TOB-suc-PMO[C$^{bz}$-T-C$^{bz}$] (Elongation-3)

TOB-suc-PMO[C$^{bz}$-T] wet crystals (5.7 g, corresponding to 3.20 mmol) were dissolved in chloroform (43 mL), N,N-diisopropylethylamine (0.73 g, 25.6 mmol) and ClPONMe$_2$-mo(Tr)C$^{bz}$ (3.35 g, 4.8 mmol) were added, and the mixture was stirred at room temperature for 16 hr. After confirmation of the completion of the reaction by UHPLC, the reaction mixture was cooled to room temperature, morpholine (0.28 g, 3.20 mmol) was added and the mixture was stirred at room temperature for 1 hr. The reaction mixture was ice-cooled, 2,2,2-trifluoroethanol (13.0 mL) and ethanol (1.48 g, 32.0 mmol) were added, a solution of trifluoroacetic acid (2.92 g, 25.6 mmol) and triethylamine (1.20 g, 11.8 mmol) in chloroform (9.8 mL) was added dropwise, and the mixture was stirred at 15° C. for 1.5 hr. After confirmation of the completion of the reaction by UHPLC, the reaction mixture was ice-cooled, and a solution of N,N-diisopropylethylamine (3.23 g, 25.6 mmol) in chloroform (4.5 mL) was added dropwise. To the reaction mixture was added acetonitrile (106 mL), and the solvent was evaporated under reduced pressure. The obtained slurry was stirred at 0° C. for 15 min, and the precipitates were collected by filtration. The obtained crystals were washed again with acetonitrile (53 mL) to give TOB-suc-PMO[$C^{bz}$-T-$C^{bz}$]. The crystals were directly used without drying as a starting material of the next reaction.

Example 33

Synthesis of TOB-suc-PMO[$C^{bz}$-T] (Lithium Chloride Addition System, Elongation-2)

TOB-suc-mo$C^{bz}$ wet crystals (4.9 g, corresponding to 3.08 mmol) were dissolved in chloroform (34.9 mL), lithium chloride (143 mg, 3.38 mmol), N,N-diisopropylethylamine (0.72 g, 5.54 mmol) and ClPONMe$_2$-mo(Tr)T (2.81 g, 4.61 mmol) were added, and the mixture was stirred at 40° C. for 16 hr. After confirmation of the completion of the reaction by UHPLC, the reaction mixture was cooled to room temperature, morpholine (0.32 g, 3.69 mmol) was added and the mixture was stirred at room temperature for 1 hr. The reaction mixture was ice-cooled, 2,2,2-trifluoroethanol (12.5 mL) and ethanol (1.41 g, 30.8 mmol) were added, and then, a solution of trifluoroacetic acid (1.75 g, 15.4 mmol) and triethylamine (0.49 g, 4.86 mmol) in chloroform (5.9 mL) was added dropwise, and the mixture was stirred at room temperature for 1 hr. After confirmation of the completion of the reaction by UHPLC, the reaction mixture was ice-cooled, and a solution of N,N-diisopropylethylamine (2.0 g, 15.4 mmol) in chloroform (2.7 mL) was added dropwise. To the reaction mixture was added acetonitrile (82 mL), and the solvent was evaporated under reduced pressure. The obtained slurry was stirred at 0° C. for 30 min, and the precipitates were collected by filtration. The obtained crystals were washed again with acetonitrile (41 mL) to give TOB-suc-PMO[$C^{bz}$-T]. The crystals were directly used without drying as a starting material of the next reaction.

Example 34

Synthesis of TOB-suc-PMO[$C^{bz}$-T-$C^{bz}$] (Lithium Chloride Addition System, Elongation-3)

TOB-suc-PMO[$C^{bz}$-T] crystals (5.5 g, corresponding to 3.05 mmol) were dissolved in chloroform (44.6 mL), lithium chloride (142 mg, 3.36 mmol), N,N-diisopropylethylamine (0.71 g, 5.49 mmol) and ClPONMe$_2$-mo(Tr)$C^{bz}$ (3.19 g, 4.58 mmol) were added, and the mixture was stirred at 40° C. for 16 hr. After confirmation of the completion of the reaction by UHPLC, the reaction mixture was cooled to room temperature, morpholine (0.26 g, 3.05 mmol) was added and the mixture was stirred at room temperature for 1 hr. The reaction mixture was ice-cooled, 2,2,2-trifluoroethanol (12.4 mL) and ethanol (1.41 g, 30.5 mmol) were added, a solution of trifluoroacetic acid (1.74 g, 15.3 mmol) and triethylamine (0.52 g, 5.19 mmol) in chloroform (5.8 mL) was added dropwise, and the mixture was stirred at room temperature for 1 hr. After confirmation of the completion of the reaction by UHPLC, the reaction mixture was ice-cooled and a solution of N,N-diisopropylethylamine (1.97 g, 15.3 mmol) in chloroform (2.7 mL) was added dropwise. To the reaction mixture was added acetonitrile (100 mL), and the solvent was evaporated under reduced pressure. The obtained slurry was stirred at 0° C. for 15 min, and the precipitates were collected by filtration. The obtained crystals were washed again with acetonitrile (50 mL), and dried under reduced pressure to give TOB-suc-PMO[$C^{bz}$-T-$C^{bz}$] (6.74 g, yield 106%).

Example 35

Synthesis of TOB-suc-PMO[$C^{bz}$-T] (Lithium Chloride and Acetic Anhydride Addition System, Elongation-2)

TOB-suc-mo$C^{bz}$ (4.3 g, 3.23 mmol) was dissolved in chloroform (42.8 mL), lithium chloride (150 mg, 3.55 mmol), N,N-diisopropylethylamine (0.73 g, 5.81 mmol) and ClPONMe$_2$-mo(Tr)T (2.95 g, 4.85 mmol) were added, and the mixture was stirred at room temperature for 15 hr. After confirmation of the completion of the reaction by UHPLC, the reaction mixture was cooled to room temperature, acetic anhydride (0.03 mL, 0.32 mmol) and 2,6-lutidine (0.19 mL, 1.62 mmol) were added and the mixture was stirred at room temperature for 1 hr. To the reaction mixture was added morpholine (0.28 g, 3.23 mmol) and the mixture was stirred at room temperature for 1 hr. The reaction mixture was ice-cooled, indole (3.78 g, 32.3 mmol) was added, a solution of trifluoroacetic acid (2.86 g, 25.8 mmol) in chloroform (19.2 mL) was added dropwise, and the mixture was stirred at room temperature for 1.5 hr. After confirmation of the completion of the reaction by UHPLC, the reaction mixture was ice-cooled, and a solution of N,N-diisopropylethylamine (3.25 g, 25.8 mmol) in chloroform (4.5 mL) was added dropwise. To the reaction mixture was added acetonitrile (86 mL) and the solvent was evaporated under reduced pressure. The obtained slurry was stirred at 0° C. for 15 min, and the precipitates were collected by filtration. The obtained crystals were washed again with acetonitrile (43 mL) to give TOB-suc-PMO[$C^{bz}$-T]. The crystals were directly used without drying as a starting material of the next reaction.

Example 36

Synthesis of TOB-suc-PMO[$C^{bz}$-T-$C^{bz}$] (Lithium Chloride and Acetic Anhydride Addition System, Elongation-3)

TOB-suc-PMO[$C^{bz}$-T] wet crystals (6.5 g, corresponding to 3.23 mmol) were dissolved in chloroform (53.4 mL), lithium chloride (150 mg, 3.36 mmol), N,N-diisopropylethylamine (0.73 g, 5.81 mmol) and ClPONMe$_2$-mo(Tr)$C^{bz}$ (3.38 g, 4.85 mmol) were added, and the mixture was stirred at room temperature for 40 hr. After confirmation of the completion of the reaction by UHPLC, the reaction mixture was cooled to room temperature, acetic anhydride (0.03 mL, 0.32 mmol) and 2,6-lutidine (0.15 mL, 1.29 mmol) were added and the mixture was stirred at room temperature for 1 hr. To the reaction mixture was added morpholine (0.28 g, 3.23 mmol) and the mixture was stirred at room temperature for 1 hr. The reaction mixture was ice-cooled, indole (3.78 g, 32.3 mmol) was added, a solution of trifluoroacetic acid (2.86 g, 25.8 mmol) in chloroform (19.2 mL) was added dropwise, and the mixture was stirred at room temperature for 1.5 hr. After confirmation of the completion of the reaction by UHPLC, the reaction mixture was ice-cooled and a solution of N,N-diisopropylethylamine (3.25 g, 25.8 mmol) in chloroform (4.5 mL) was added dropwise. To the reaction mixture was added acetonitrile (107 mL), and the solvent was evaporated under reduced pressure. The obtained slurry was stirred at 0° C. for 15 min, and the precipitates were collected by filtration. The obtained crystals were washed again with acetonitrile (53 mL), and dried under reduced pressure to give TOB-suc-PMO[$C^{bz}$-T-$C^{bz}$]. The crystals were directly used without drying as a starting material of the next reaction.

Example 37

Synthesis of TOB-suc-PMO[$C^{bz}$-$C^{bz}$] (Elongation-2)

TOB-suc-mo$C^{bz}$ wet crystals (16.1 g, corresponding to 3.2 mmol) were dissolved in chloroform (42 mL), N,N-diisopropylethylamine (0.74 g, 5.76 mmol) and ClPONMe$_2$-mo(Tr)$C^{bz}$ (3.35 g, 4.80 mmol) were added, and the mixture was stirred at room temperature for 15 hr. After confirmation of the completion of the reaction by UHPLC, the reaction mixture was cooled to room temperature, morpholine (0.28 g, 3.2 mmol) was added and the mixture was stirred at room temperature for 1 hr. The reaction mixture was ice-cooled, 2,2,2-trifluoroethanol (14.1 mL) and ethanol (1.5 g, 32.0 mmol) were added, a solution of trifluoroacetic acid (2.92 g, 25.6 mmol) and triethylamine (1.13 g, 11.2 mmol) in chloroform (40 mL) was added dropwise, and the mixture was stirred at 15° C. for 30 min. To the reaction mixture was added 2,2,2-trifluoroethanol (3.5 mL), and the mixture was further stirred at 15° C. for 1 hr. After confirmation of the completion of the reaction by UHPLC, the reaction mixture was ice-cooled and a solution of N,N-diisopropylethylamine (3.31 g, 25.6 mmol) in chloroform (30 mL) was added dropwise. To the reaction mixture was added acetonitrile (75 mL), and the solvent was evaporated under reduced pressure. To the obtained residue was added acetonitrile (25 mL), and the solvent was evaporated under reduced pressure. Acetonitrile (100 mL) was added. The obtained slurry was stirred at 0° C. for 30 min, and the precipitates were collected by filtration. The obtained crystals were washed again with acetonitrile (100 mL), and dried under reduced pressure to give TOB-suc-PMO[$C^{bz}$-$C^{bz}$] (5.4 g, yield 96.6% relative to TOB-suc-mo$C^{bz}$).

Example 38

Synthesis of TOB-suc-PMO[$C^{bz}$-$C^{bz}$-T] (Elongation-3)

TOB-suc-PMO[$C^{bz}$-$C^{bz}$] (5.4 g, 3.09 mmol) was dissolved in chloroform (54 mL), N,N-diisopropylethylamine (0.72 g, 5.56 mmol) and ClPONMe$_2$-mo(Tr)T (2.82 g, 4.64 mmol) were added, and the mixture was stirred at room temperature for 23 hr. After confirmation of the completion of the reaction by UHPLC, the reaction mixture was cooled to room temperature, morpholine (0.27 g, 3.09 mmol) was added and the mixture was stirred at room temperature for 1 hr. The reaction mixture was ice-cooled, 2,2,2-trifluoroethanol (17 mL) and ethanol (1.42 g, 30.9 mmol) were added, a solution of trifluoroacetic acid (2.82 g, 24.7 mmol) and triethylamine (1.16 g, 11.4 mmol) in chloroform (39 mL) was added dropwise, and the mixture was stirred at 15° C. for 1.5 hr. After confirmation of the completion of the reaction by UHPLC, the reaction mixture was ice-cooled, and a solution of N,N-diisopropylethylamine (3.19 g, 24.7 mmol) in chloroform (30 mL) was added dropwise. To the reaction mixture was added acetonitrile (160 mL), and the solvent was evaporated under reduced pressure. To the obtained residue was added acetonitrile (80 mL), and the solvent was evaporated under reduced pressure. Acetonitrile (100 mL) was added. The obtained slurry was stirred at 0° C. for 30 min, and the precipitates were collected by filtration. The obtained crystals were washed again with acetonitrile (100 mL) and dried under reduced pressure to give TOB-suc-PMO[$C^{bz}$-$C^{bz}$-T]. The crystals were directly used without drying as a starting material of the next reaction.

Example 39

Synthesis of TOB-suc-PMO[$C^{bz}$-$C^{bz}$-T-$C^{bz}$-$G^{ce/pac}$-$G^{ce/pac}$-T-T-$C^{bz}$-T-$G^{ce/pac}$-$A^{bz}$-$A^{bz}$-$G^{ce/pac}$-$G^{ce/pac}$-T-$G^{ce/pac}$-T-T-$C^{bz}$]-Tr (Results List)

TOB-suc-mo(Tr)$C^{bz}$ (5.0 g, 3.2 mmol) was sequentially subjected to coupling of the corresponding monomer and deprotection of trityl group in one pot according to the methods described in Examples 37 and 38. The step yield at each stage is shown in the following Table. The resultant products with a chain length without a numerical value were used for the next step without drying.

TABLE 8

| chain length | step yield |
|---|---|
| 1mer | 99% |
| 2mer | 97% |
| 3mer | — |
| 4mer | — |
| 5mer | 97% |
| 6mer | — |
| 7mer | — |
| 8mer | 92% |
| 9mer | — |
| 10mer | — |
| 11mer | 98% |
| 12mer | — |
| 13mer | — |
| 14mer | — |
| 15mer | 96% |
| 16mer | — |
| 17mer | — |
| 18mer | 97% |
| 19mer | — |
| 20mer | 98% |
| 21mer | 100% |

Example 40 Synthesis of TOB-suc-PMO[$C^{bz}$-$C^{bz}$-T-$C^{bz}$-$C^{bz}$-$G^{ce/pac}$-$G^{ce/pac}$-T-T-$C^{bz}$] (Lithium Chloride Addition System, Elongation-10)

TOB-suc-PMO[$C^{bz}$-$C^{bz}$-T-$C^{bz}$-$C^{bz}$-$G^{ce/pac}$-$G^{ce/pac}$-T-T] wet crystals (12.9 g, corresponding to 2.37 mmol) were dissolved in chloroform (100 mL), lithium chloride (150 mg, 3.56 mmol), N,N-diisopropylethylamine (0.53 g, 4.27 mmol) and ClPONMe$_2$-mo(Tr)$C^{bz}$ (2.48 g, 3.56 mmol) were added, and the mixture was stirred at room temperature for 33 hr. After confirmation of the completion of the reaction by UHPLC, the reaction mixture was cooled to room temperature, morpholine (0.78 g, 9.0 mmol) was added and the mixture was stirred at room temperature for 1 hr. The reaction mixture was ice-cooled, 2,2,2-trifluoroethanol (10.2 mL) and ethanol (1.1 g, 23.7 mmol) were added, and then, a solution of trifluoroacetic acid (1.89 g, 16.6 mmol) in chloroform (10 mL) was added dropwise, and the mixture was stirred at room temperature for 2 hr. After confirmation of the completion of the reaction by UHPLC, the reaction mixture was ice-cooled, and a solution of N,N-diisopropylethylamine (2.07 g, 16.0 mmol) in chloroform (10 mL) was added dropwise. To the reaction mixture was added acetonitrile (200 mL), and the solvent was evaporated under reduced pressure. To the obtained residue was added acetonitrile (100 mL). The obtained slurry was stirred at 0° C. for 30 min, and the precipitates were collected by filtration. The obtained crystals were washed again with acetonitrile (100 mL) to give TOB-suc-PMO[$C^{bz}$-$C^{bz}$-T-$C^{bz}$-$C^{bz}$-$G^{ce/pac}$-$G^{ce/pac}$-T-T-$C^{bz}$]. The crystals were directly used without drying as a starting material of the next reaction.

Example 41

Synthesis of TOB-suc-PMO[$C^{bz}$-$G^{bz}$-T-$G^{bz}$-$G^{bz}$-$G^{ce/pac}$-$G^{ce/pac}$-T-T-$C^{bz}$-T] (Lithium Chloride Addition System, Elongation-11)

TOB-suc-PMO[$C^{bz}$-$C^{bz}$-T-$C^{bz}$-$C^{bz}$-$G^{ce/pac}$-$G^{ce/pac}$-T-T-$C^{bz}$] wet crystals (12.6 g, 2.37 mmol) were dissolved in chloroform (110 mL), lithium chloride (150 mg, 3.56 mmol), N,N-diisopropylethylamine (0.53 g, 4.27 mmol) and ClPONMe$_2$-mo(Tr)T (2.17 g, 3.56 mmol) were added, and the mixture was stirred at room temperature for 19 hr. After confirmation of the completion of the reaction by UHPLC, the reaction mixture was cooled to room temperature, morpholine (0.78 g, 9.01 mmol) was added and the mixture was stirred at room temperature for 1 hr. The reaction mixture was ice-cooled, 2,2,2-trifluoroethanol (10.2 mL) and ethanol (1.09 g, 23.7 mmol) were added, a solution of trifluoroacetic acid (1.89 g, 16.6 mmol) in chloroform (10 mL) was added dropwise, and the mixture was stirred at room temperature for 2 hr. After confirmation of the completion of the reaction by UHPLC, the reaction mixture was ice-cooled, and a solution of N,N-diisopropylethylamine (2.07 g, 16.0 mmol) in chloroform (10 mL) was added dropwise. To the reaction mixture was added acetonitrile (150 mL), and the solvent was evaporated under reduced pressure. To the obtained residue was added acetonitrile (200 mL), and the solvent was evaporated under reduced pressure. Acetonitrile (50 mL) was added, and the obtained slurry was stirred at 0° C. for 30 min, and the precipitates were collected by filtration. The obtained crystals were washed again with acetonitrile (100 mL), and dried under reduced pressure to give TOB-suc-PMO[$C_{bz}$-$C^{bz}$-T-$C^{bz}$-$C^{bz}$-$G^{ce/pac}$-$G^{ce/pac}$-T-T-$C^{bz}$-T]. The crystals were directly used without drying as a starting material of the next reaction.

Example 42

Synthesis of TOB-suc-PMO[$C^{bz}$-$C^{bz}$-T-$C^{bz}$-$C^{bz}$-$G^{ce/pac}$-$G^{ce/pac}$-T-T-$C^{bz}$-T-$G^{ce/pac}$-$A^{bz}$-$A^{bz}$-$G^{ce/pac}$-$G^{ce/pac}$-T-$G^{ce/pac}$-T-T-$C^{bz}$]-Tr (Results List)

TOB-suc-mo(Tr)$C^{bz}$ (5.0 g, 3.2 mmol) was sequentially subjected to coupling of the corresponding monomer and deprotection of trityl group in one pot according to the methods described in Examples 37, 38, 40 and 41. The step yield at each stage is shown in the following Table. The resultant products with a chain length without a numerical value were used for the next step without drying.

TABLE 9

| chain length | step yield |
| --- | --- |
| 1mer | — |
| 2mer | — |
| 3mer | — |
| 4mer | — |
| 5mer | — |
| 6mer | 89% |
| 7mer | — |
| 8mer | 91% |
| 9mer | — |
| 10mer | — |
| 11mer | — |
| 12mer | 98% |
| 13mer | — |
| 14mer | 96% |
| 15mer | — |
| 16mer | — |
| 17mer | 80% |
| 18mer | — |
| 19mer | — |
| 20mer | — |
| 21mer | 69% |

The scheme of Examples 43, 44 and 45 is shown below.

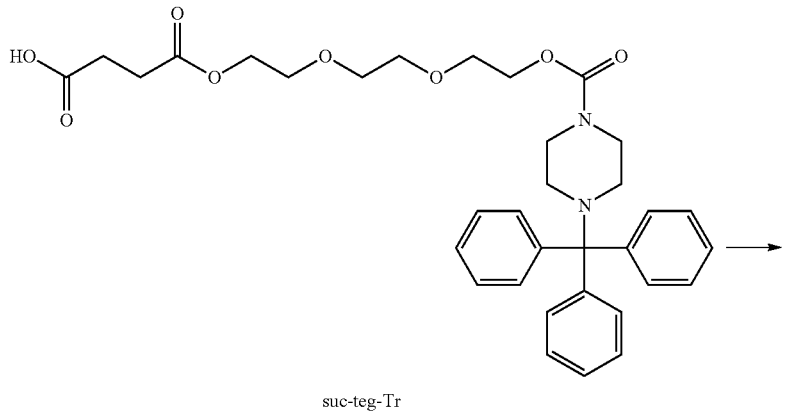

suc-teg-Tr

-continued
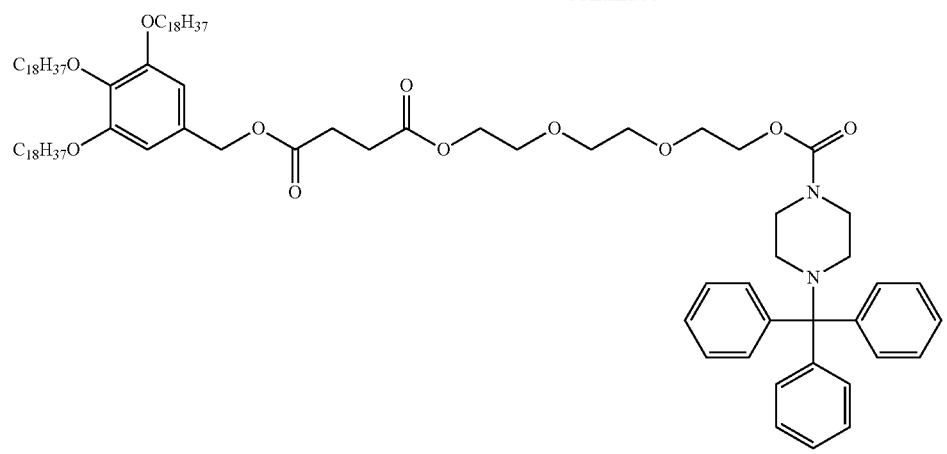
TOB-suc-teg-Tr
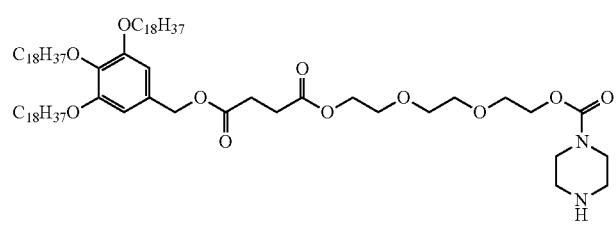
TOB-suc-teg-H
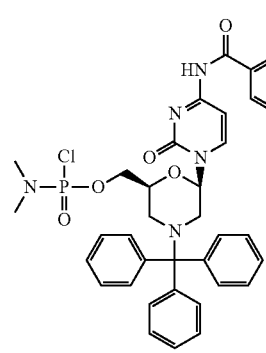
ClPONMe$_2$-mo(Tr)C$^{bz}$

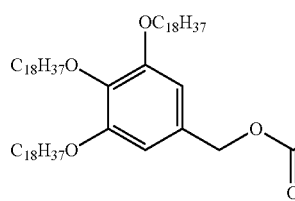
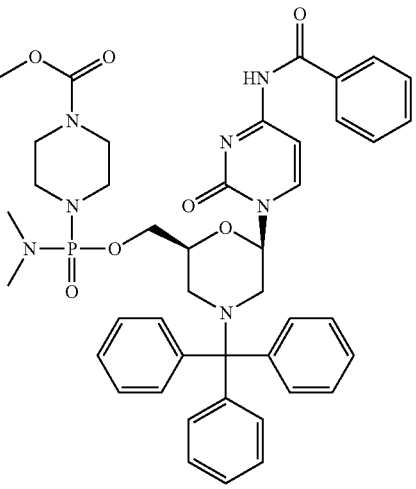

TOB-suc-teg-mo(Tr)C$^{bz}$

Example 43

Synthesis of TOB-suc-teg-Tr 3,4,5-tri(octadecyl)benzyl alcohol (91.4 mg, 0.1 mmol) was dissolved in chloroform (1.0 mL), suc-teg-Tr (72.6 mg, 0.12 mmol), EDC.HCl (23.0 mg, 0.12 mmol) and 4-dimethylaminopyridine (1.2 mg, 0.01 mmol) were added, and the mixture was stirred at room temperature for 65 hr. After confirmation of the completion of the reaction by UHPLC, acetonitrile (2 mL) was added, and the solvent was evaporated under reduced pressure. To the obtained residue was added acetonitrile (4 mL), and the precipitate was collected by filtration, and dried under reduced pressure to give TOB-suc-teg-Tr (140 mg, yield 93%).

TOF-MS+ (m/z) 1501.0

Example 44

Synthesis of TOB-suc-teg-H

TOB-suc-teg-Tr (139 mg, 0.09 mmol) was dissolved in chloroform (1.4 mL) and ice-cooled, 2,2,2-trifluoroethanol (0.4 mL) and ethanol (42.8 g, 0.93 mmol) were added, a solution of trifluoroacetic acid (82.7 mg, 0.75 mmol) and triethylamine (47.4 mg, 0.47 mmol) in chloroform (0.5 mL) was added dropwise, and the mixture was stirred at room temperature for 2 hr. After confirmation of the completion of the reaction by UHPLC, the reaction mixture was ice-cooled, and a solution of N,N-diisopropylethylamine (97 mg, 0.75 mmol) in chloroform (0.5 mL) was added dropwise. To the reaction mixture was added acetonitrile (5 mL), and the solvent was evaporated under reduced pressure. To the obtained residue was added acetonitrile (4 mL), and the mixture was stirred at 0° C. for 30 min. The precipitates were collected by filtration to give TOB-suc-teg-H. The crystals were directly used without drying as a starting material of the next reaction.

TOF-MS+ (m/z) 1257.9

Example 45

Synthesis of TOB-suc-teg-mo(Tr)C$^{bz}$

TOB-suc-teg-H wet crystals (168 mg, corresponding to 0.09 mmol) were dissolved in chloroform (1.2 mL), N,N-diisopropylethylamine (20.7 mg, 0.16 mmol) and ClPONMe$_2$-mo(Tr)C$^{bz}$ (92.8 mg, 0.13 mmol) were added, and the mixture was stirred with heating at room temperature for 13 hr. After confirmation of the completion of the reaction by UHPLC, the reaction mixture was cooled to room temperature, morpholine (11.3 mg, 0.09 mmol) was added and the mixture was stirred at room temperature for 1 hr. To the reaction mixture was added acetonitrile (2.4 mL), and the solvent was evaporated under reduced pressure. To the obtained residue was added acetonitrile (3 mL), and the mixture was stirred at 0° C. for 30 min. The precipitate was collected by filtration, and dried under reduced pressure to give TOB-suc-teg-mo(Tr)C$^{bz}$ (148 mg, yield 86%, relative to TOB-suc-teg-Tr).

TOF-MS+ (m/z) 1919.0

INDUSTRIAL APPLICABILITY

Using a morpholino nucleotide wherein 5'-hydroxy group or a hydroxy group present on the substituent of the 5'-hydroxy group is protected by a particular protecting group of the present invention, a method capable of efficiently producing the morpholino oligonucleotide in a high yield by a liquid phase synthesis can be provided.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A morpholino nucleotide represented by formula (I):

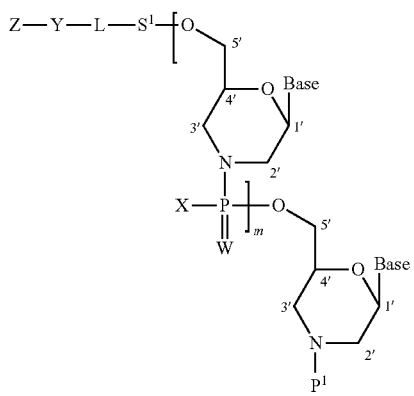

wherein
m is any integer of not less than 0;
each of m+1 Base is independently an optionally protected nucleic acid base;
$P^1$ is a hydrogen atom, or a temporary protecting group removable under acidic conditions;
each of m X is independently a $C_{1-6}$ alkoxy group, a di-$C_{1-6}$ alkylamino group, or a piperazino group wherein a nitrogen atom at the 4-position is protected by a protecting group and further optionally substituted;
each of m W is independently an oxygen atom or a sulfur atom;
$S^1$ is a single bond, or a group represented by *O—$S^2$**, wherein * indicates the bonding position to L, ** indicates the bonding position to a 5'-hydroxy group, and $S^2$ is a spacer having a main chain containing 1 to 20 atoms;
L is a single bond, or a group represented by the formula (a1):

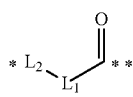

wherein
* indicates the bonding position to Y;
** indicates the bonding position to $S^1$;
$L_1$ is an optionally substituted divalent $C_{1-22}$ hydrocarbon group; and
$L_2$ is C(=O) or a group represented by *N($R^3$)—$R^1$—N($R^2$)C(=O), wherein  indicates the bonding position to $L^1$, * indicates the bonding position to Y, $R^1$ is an optionally substituted $C_{1-22}$ alkylene group, $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond;

Y is a single bond, an oxygen atom or NR, wherein R is a hydrogen atom, an alkyl group or an aralkyl group; and
Z is a group represented by formula (a2):

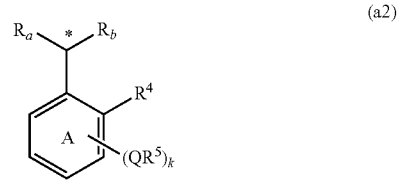

wherein
* indicates the bonding position to Y;
$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;
each of k Q is independently a single bond, or —O—, —S—, —OC(=O)—, —NHC(=O)— or —NH—;
each of k $R^5$ is independently an organic group containing an alkyl group having not less than 10 and not more than 300 carbon atoms and/or an alkenyl group containing not less than 10 and not more than 300 carbon atoms;
k is an integer of 1 to 4;
ring A optionally further has, in addition to k of $QR^5$, a substituent selected from the group consisting of a halogen atom, a $C_{1-6}$ alkyl group optionally substituted by one or more halogen atoms, and a $C_{1-6}$ alkoxy group optionally substituted by one or more halogen atoms;
$R_a$ is a hydrogen atom;
$R_b$ is a hydrogen atom, or a group represented by formula (a3):

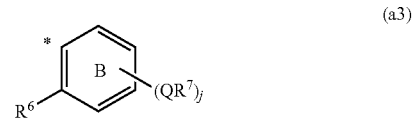

wherein
* indicates a bonding position;
j is an integer of 0 to 4;
each of j Q is as defined above;
each of j $R^7$ is independently an organic group having an alkyl group containing not less than 10 and not more than 300 carbon atoms and/or an alkenyl group containing not less than 10 and not more than 300 carbon atoms;
$R^6$ is a hydrogen atom, or optionally a single bond or —O— in combination with $R^4$ to form a fluorenyl group or a xanthenyl group together with ring A; and
ring B optionally further has, in addition to j of $QR^7$, a substituent selected from the group consisting of a halogen atom, a $C_{1-6}$ alkyl group optionally substituted by one or more halogen atoms, and a $C_{1-6}$ alkoxy group optionally substituted by one or more halogen atoms, or
$R_a$ and $R_b$ are joined to form an oxygen atom.
2. The morpholino nucleotide according to claim 1, wherein m is 0.

3. The morpholino nucleotide according to claim 1, wherein L is a succinyl group, and $R^5$ and/or $R^7$ are/is an alkyl group containing 10 to 40 carbon atoms.

4. The morpholino nucleotide according to claim 1, wherein L is a succinyl group, $R_a$ and $R_b$ are both hydrogen atoms, and $R^5$ is an alkyl group containing 10 to 40 carbon atoms.

5. The morpholino nucleotide according to claim 1, wherein L is a succinyl group, and $R^5$ and/or $R^7$ are/is an alkyl group containing 12 to 30 carbon atoms.

6. The morpholino nucleotide according to claim 1, wherein

L is a succinyl group, and

Z—Y— is a group selected from the group consisting of a 3,4,5-tri(octadecyloxy)benzyloxy group, a 3,5-di(docosyloxy)benzyloxy group, a 3,5-bis[3',4',5'-tri(octadecyloxy)benzyloxy]benzyloxy group, a 3,4,5-tris[3',4',5'-tri(octadecyloxy)benzyloxy]-benzyloxy group, a 3,4,5-tri(octadecyloxy)benzylamino group, a 2,4-di(docosyloxy)benzylamino group, a 3,5-di(docosyloxy)benzylamino group, a di(4-docosyloxyphenyl)methylamino group, a 4-methoxy-2-[3',4',5'-tri(octadecyloxy)benzyloxy]-benzylamino group, a 4-methoxy-2-[3',4',5'-tri(octadecyloxy)-cyclohexylmethyloxy]benzylamino group, a 2,4-di(dodecyloxy)benzylamino group, a phenyl(2,3,4-tri(octadecyloxy)phenyl)methylamino group, a di[4-(12-docosyloxydodecyloxy)phenyl]methylamino group, a 3,5-bis[3',4',5'-tri(octadecyloxy)benzyloxy]benzylamino group, and a 3,4,5-tris[3',4',5'-tri(octadecyloxy)benzyloxy]-benzylamino group.

7. The morpholino nucleotide according to claim 1, wherein Z—Y-L- is selected from the group consisting of a 2-{2,4-di(2',3'-dihydrophytyloxy)benzylaminocarbonyl}-ethylcarbonyl group;

a 3,5-di(2',3'-dihydrophytyloxy)benzylsuccinyl group;

a 4-(2',3'-dihydrophytyloxy)benzylsuccinyl group;

a 2-{1-[(2-chloro-5-(2',3'-dihydrophytyloxy)phenyl)]benzylaminocarbonyl}ethylcarbonyl group;

a 3,4,5-tri(2',3'-dihydrophytyloxy)benzylsuccinyl group;

a 2-{3,4,5-tri(2',3'-dihydrophytyloxy)-benzylaminocarbonyl}ethylcarbonyl group;

a 2-{4-(2',3'-dihydrophytyloxy)benzylaminocarbonyl}-ethylcarbonyl group;

a 2-{2-[3',4',5'-tri(2",3"-dihydrophytyloxy)benzyloxy]-4-methoxybenzylaminocarbonyl}ethylcarbonyl group;

a 2-{4-(2',3'-dihydrophytyloxy)-2-methoxybenzylaminocarbonyl}ethylcarbonyl group;

a 4-(2',3'-dihydrophytyloxy)-2-methylbenzylsuccinyl group;

a 2-{4-(2',3'-dihydrophytyloxy)-2-methylbenzylaminocarbonyl}ethylcarbonyl group;

a 4-[2,2,4,8,10,10-hexamethyl-5-dodecanoylamino]-benzylsuccinyl group;

a 2-{4-[2,2,4,8,10,10-hexamethyl-5-dodecanoylamino]-benzylaminocarbonyl}ethylcarbonyl group;

a 4-(3,7,11-trimethyldodecyloxy)benzylsuccinyl group;

a 2-{4-(3,7,11-trimethyldodecyloxy)benzylaminocarbonyl}-ethylcarbonyl group;

a 2-{3,5-di(2',3'-dihydrophytyloxy)benzylaminocarbonyl}-ethylcarbonyl group;

a 2-{1-[2,3,4-tri(2',3'-dihydrophytyloxy)phenyl]-benzylaminocarbonyl}ethylcarbonyl group;

a 2-{1-[4-(2',3'-dihydrophytyloxy)phenyl]-4'-(2',3'-dihydrophytyloxy)benzylaminocarbonyl}ethylcarbonyl group;

a 3,4,5-tris[3,4,5-tri(2',3'-dihydrophytyloxy)benzyl]-benzylsuccinyl group; and a 2-{3,4,5-tris[3,4,5-tri(2',3'-dihydrophytyloxy)benzyl]-benzylaminocarbonyl}ethylcarbonyl group.

8. The morpholino nucleotide according to claim 1, wherein $P^1$ is a trityl group, a monomethoxytrityl group, or a dimethoxytrityl group.

\* \* \* \* \*

UNITED STATES PATENT AND TRADEMARK OFFICE
CERTIFICATE OF CORRECTION

PATENT NO. : 9,790,497 B2
APPLICATION NO. : 14/946991
DATED : October 17, 2017
INVENTOR(S) : Takayoshi Torii et al.

Page 1 of 4

It is certified that error appears in the above-identified patent and that said Letters Patent is hereby corrected as shown below:

In the Specification

Column 2, Line 2, "1447" should read --1447.--

Column 18, Line 38, "C1-5" should read --$C_{1-6}$--

Column 29, Line 40, "di($C_{1-5}$" should read --di($C_{1-6}$--

Column 30, Line 34-37 (approx.), " 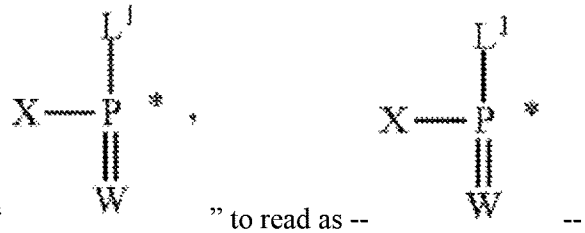 " to read as -- --

Column 33, Line 65, "mass." should read --mass%.--

Column 36, Line 53, "is," should read --is--

Column 40, Line 21, "ClPONMe$_2$-mo(Tr)C$^{bz}$" should read --C1PONMe$_2$-mo(Tr)C$^{bz}$--

Column 40, Line 41, "ClPONMe$_2$-mo(Tr)T" should read --C1PONMe$_2$-mo(Tr)T--

Column 40, Line 66, "ClPONMe$_2$-mo(Tr)A$^{bz}$" should read --C1PONMe$_2$-mo(Tr)A$^{bz}$--

Column 41, Line 17, "ClPONMe$_2$-mo(Tr)G$^{pac}$" should read --C1PONMe$_2$-mo(Tr)G$^{pac}$--

Column 41, Line 48, "ClPONMe$_2$-mo(Tr)G$^{ce/pac}$" should read --C1PONMe$_2$-mo(Tr)G$^{ce/pac}$--

Signed and Sealed this
Ninth Day of April, 2019

Andrei Iancu
*Director of the United States Patent and Trademark Office*

CERTIFICATE OF CORRECTION (continued)
U.S. Pat. No. 9,790,497 B2

Page 2 of 4

Column 48, Line 35, "ClPONMe₂-mo(Tr)T" should read --ClPONMe₂-mo(Tr)T--

Column 53, Line 29, "MO (Tr)C$^{bz}$]" should read --mo(Tr)C$^{bz}$]--

Column 65, Line 47, "TOB-suc-PMO[Cbz-Cbz]-Tr" should read --TOB-suc-PMO[C$^{bz}$-C$^{bz}$]-Tr--

Column 71, Line 58, "were" should read --were observed--

Column 71, Line 66, "dectected" should read --detected--

Column 73, Line 6, " 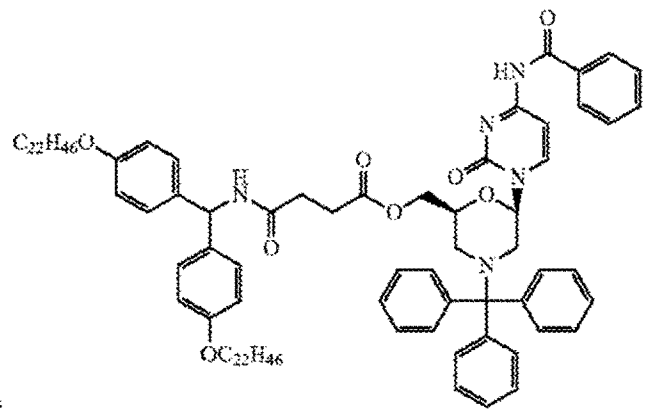 " should read as

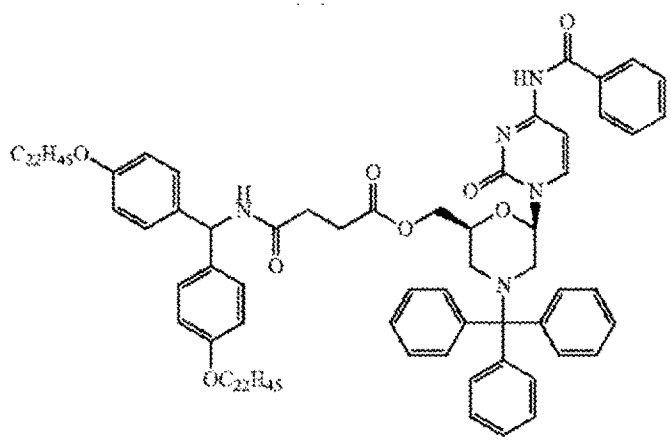

-- --

Column 74, Line 6, " 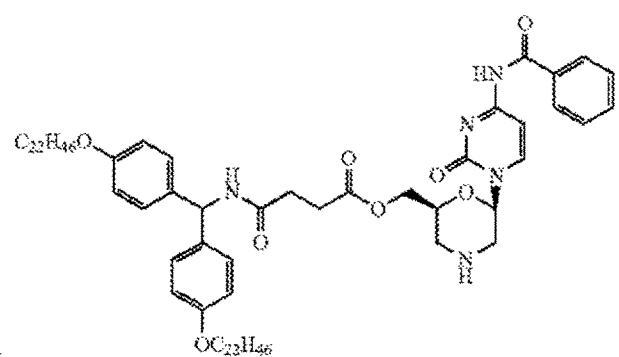 " should read as

CERTIFICATE OF CORRECTION (continued)
U.S. Pat. No. 9,790,497 B2

Page 3 of 4

Columns 73 and 74, Line 8, " 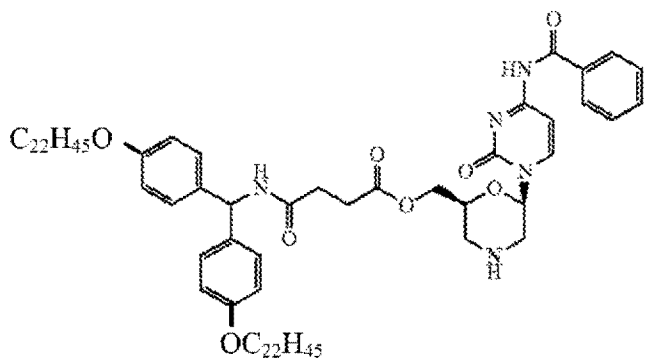 " should read -- 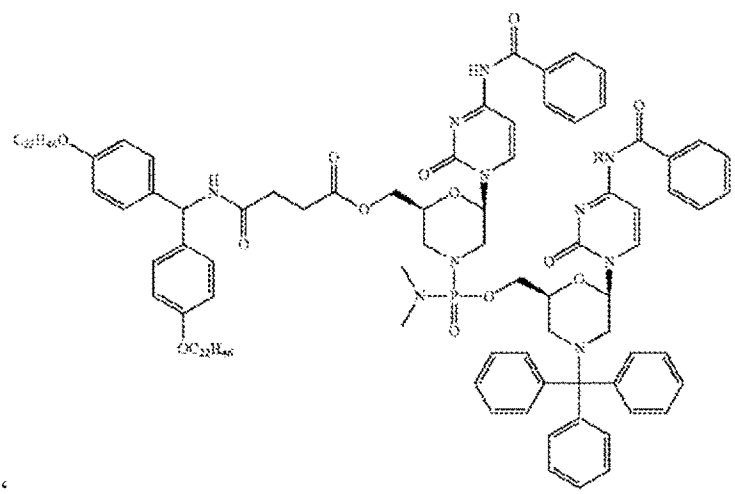 --

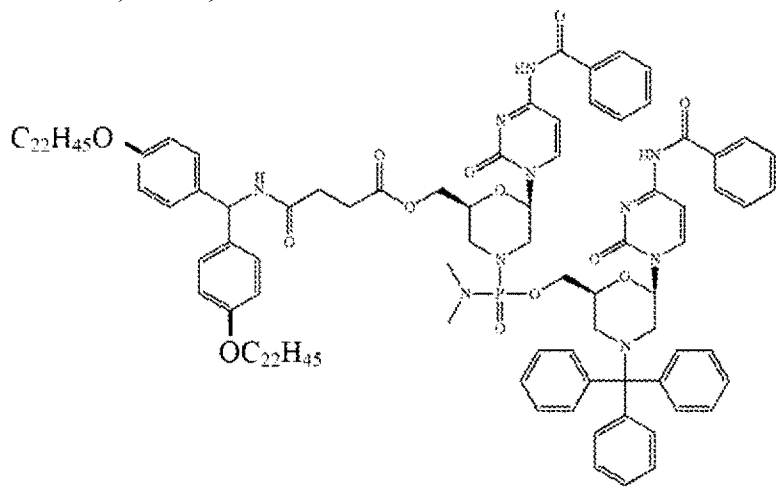

Column 82, Line 14, "TOB-suc-PMO[$C^{bz}$-$C^{bz}$-T-$C^{bz}$-$G^{ce/pac}$" should read --TOB-suc-PMO[$C^{bz}$-$C^{bz}$-T-$C^{bz}$-$C^{bz}$-$G^{ce/pac}$--

CERTIFICATE OF CORRECTION (continued)
U.S. Pat. No. 9,790,497 B2

Column 83, Line 18, "TOB-suc-PMO[$C^{bz}$-$G^{bz}$-T-$G^{bz}$-$G^{bz}$" should read --TOB-suc-PMO[$C^{bz}$-$C^{bz}$-T-$C^{bz}$-$C^{bz}$--

Column 84, Line 6, "[$C_{bz}$" should read --[$C^{bz}$--